(12) United States Patent
Craven et al.

(10) Patent No.: US 11,723,369 B2
(45) Date of Patent: *Aug. 15, 2023

(54) SYMBIONT FOR ENHANCEMENT OF PLANT PERFORMANCE

(71) Applicant: Noble Research Institute, LLC, Ardmore, OK (US)

(72) Inventors: Kelly Craven, Ardmore, OK (US); Prasun Ray, Ardmore, OK (US)

(73) Assignee: Noble Research Institute, LLC, Ardmore, OK (US)

( * ) Notice: Subject to any disclaimer, the term of this patent is extended or adjusted under 35 U.S.C. 154(b) by 441 days.

This patent is subject to a terminal disclaimer.

(21) Appl. No.: 16/894,573

(22) Filed: Jun. 5, 2020

(65) Prior Publication Data

US 2022/0046929 A1 Feb. 17, 2022

Related U.S. Application Data

(63) Continuation of application No. PCT/US2018/064136, filed on Dec. 5, 2018.

(60) Provisional application No. 62/595,019, filed on Dec. 5, 2017.

(51) Int. Cl.
| | | |
|---|---|---|
| *A01N 63/30* | (2020.01) | |
| *A01N 25/08* | (2006.01) | |
| *C12N 1/14* | (2006.01) | |
| *A01H 17/00* | (2006.01) | |
| *C12N 11/14* | (2006.01) | |

(52) U.S. Cl.
CPC ............ *A01N 63/30* (2020.01); *A01H 17/00* (2013.01); *A01N 25/08* (2013.01); *C12N 1/14* (2013.01); *C12N 11/14* (2013.01)

(58) Field of Classification Search
CPC ........ A01N 63/30; A01N 25/08; A01H 17/00; C12N 11/14; C12N 1/14
See application file for complete search history.

(56) References Cited

U.S. PATENT DOCUMENTS

| | | |
|---|---|---|
| 8,975,489 B2 | 3/2015 | Craven |
| 2002/0115084 A1 | 8/2002 | Barnett et al. |
| 2007/0016974 A1 | 1/2007 | Byrum et al. |
| 2012/0198590 A1 | 8/2012 | Miller et al. |
| 2015/0073048 A1 | 3/2015 | Gandhi et al. |
| 2015/0335029 A1 | 11/2015 | Mitter et al. |

FOREIGN PATENT DOCUMENTS

WO 2017210651 A1 12/2017

OTHER PUBLICATIONS

Abbasi PA, Lazarovits G. Seed Treatment with Phosphonate (AG3) Suppresses Pythium Damping-off of Cucumber Seedlings. Plant Dis. Apr. 2006;90(4):459-464. doi: 10.1094/PD-90-0459. PMID: 30786594.*
International Search Report dated Oct. 20, 2017 for International Patent Application No. PCT/US17/35844.
International Search Report dated Mar. 22, 2019 for International Patent Application No. PCT/US18/64136.
Extended European Search Report dated Feb. 6, 2020 for EP Application No. 17807634.5.
Weiss et al. Sebacinales—One Thousand And One Interactions With Land Plants' New Phytologist, Feb. 5, 2016, vol. 211, No. 1, pp. 20-40.
Oliviera et al. Uncultured Sebacinales Clone Hj78 18S Ribosomal RNA Gene, Partial Sequence; Internal Transcribed Spacer 1, 5.8S Ribosomal RNA Gene, and Internal Transcribed Spacer 2, Complete Sequence; and 28S Ribosomal RNA Gene, Partial Sequence. NCBI Genbank entry. Jul. 13, 2012 [retrieved on Feb. 14, 2019]. Retrieved from the Internet: <https://www.ncbi.nlm.nih.gov/nuccore/406352345/>; Genbank supplement p. 1.
Ray Prasun et al: "Sebacinavermifera: a unique root symbiont with vast agronomic potential", World Journal of Microbiology and Biotechnology; vol. 32, No. 1, Dec. 29, 2015, pp. 1-10.
Sita R. Ghimire et al: "The Mycorrhizal Fungus, Sebacina vermifera, Enhances Seed Germination and Biomass Production in Switchgrass (*Panicum virgatum* L)", Bioenergy Research, vol. 2, No. 1-2, Apr. 16, 2009, pp. 51-58.
Sita R. Ghimire et al: "Enhancement of Switchgrass (*Panicum virgatum* L.) Biomass Production under Drought Conditions by the Ectomycorrhizal Fungus Sebacina vermifera", Applied and Environmental Microbiology, vol. 77, No. 19, Aug. 12, 2011, pp. 7063-7067.
Ray Prasun et al: "A Novel Delivery System for the Root Symbiotic Fungus,Sebacina vermifera, and Consequent Biomass Enhancement of Low Lignin COMT Switchgrass Lines", Bioenergy Research, vol. 8, No. 3, Jun. 12, 2015, pp. 922-933.
Franz Oberwinkler et al: "Enigmatic Sebacinales", Mycological Progress, vol. 12, No. 1, Jan. 4, 2013, pp. 1-27.

* cited by examiner

*Primary Examiner* — Kade Ariani
(74) *Attorney, Agent, or Firm* — Barnes & Thornburg LLP; Matthew S. Gibson

(57) ABSTRACT

The present disclosure provides an endophyte, *Serendipita vermifera* ssp. *bescii* ("*S. bescii*"), uses thereof and methods incorporating the use thereof for enhancement of plant performance, particularly the use of *S. bescii* with phosphite as a phosphorous source. The present disclosure also provides methods for detecting the presence of and identifying *S. bescii*.

10 Claims, 45 Drawing Sheets

Specification includes a Sequence Listing.

FIG. 4

```
                    1         10        20        30        40        50        60
                    |         |         |         |         |         |         |
       Sbescii      GGTTCGATTAGTCTTTCGCCCCTATACCCAAATTTGACGATCGATTTGCACGTCAGAATC
    C2-TC-Orchid    GGTTCGATTAGTCTTTCGCCCCTATACCCAAATTTGACGATCGATTTGCACGTCAGAATC
          C2-TC     GGTTCGATTAGTCTTTCGCCCCTATACCCAAATTTGACGATCGATTTGCACGTCAGAATC
       C2-NFSgF     GGTTCGATTAGTCTTTCGCCCCTATACCCAAATTTGACGATCGATTTGCACGTCAGAATC Sbescii      GCTACGAGCCTCCACCAGAGTTTCCTCTGGCTTCACCCTATTCAGGCATAGTTCACCATC
    C2-TC-Orchid    GCTACGAGCCTCCACCAGAGTTTCCTCTGGCTTCACCCTATTCAGGCATAGTTCACCATC
          C2-TC     GCTACGAGCCTCCACCAGAGTTTCCTCTGGCTTCACCCTATTCAGGCATAGTTCACCATC
       C2-NFSgF     GCTACGAGCCTCCACCAGAGTTTCCTCTGGCTTCACCCTATTCAGGCATAGTTCACCATC Sbescii      TTTCGGGTCCCAACATATGCGCTCTGCCGCAGATGCGTCACAGAAGGTCTGCTCCGGGCG
    C2-TC-Orchid    TTTCGGGTCCCAACATATGCGCTCTGCCGCAGATGCGTCACAGAAGGTCTGCTCCGGGCG
          C2-TC     TTTCGGGTCCCAACATATGCGCTCTGCCGCAGATGCGTCACAGAAGGTCTGCTCCGGGCG
       C2-NFSgF     TTTCGGGTCCCAACGTATACGCTCTACCGCGGATGCGTCACAGAAGGTCTGCTCCGGGCG Sbescii      TTGGTGCACAAGTACATGATCCCAACCTTTCACTTTCATTTCGCGCTCGGGTTTGACACC
    C2-TC-Orchid    TTGGTGCACAAGTACATGATCCCAACCTTTCACTTTCATTTCGCGCTCGGGTTTGACACC
          C2-TC     TTGGTGCACAAGTACATGATCCCAACCTTTCACTTTCATTTCGCGCTCGGGTTTGACACC
       C2-NFSgF     TCGGTGCACAAGTACATGTTCCCGACCTTTCACTTTCATTACGCGTCCGGGTTTGACACC Sbescii      CAAACACTCGCGCACATGTTAGACTCCTTGGTCCGTGTTTCAAGACGGGTCGCTTAAGGC
    C2-TC-Orchid    CAAACACTCGCGCACATGTTAGACTCCTTGGTCCGTGTTTCAAGACGGGTCGCTTAAGGC
          C2-TC     CAAACACTCGCGCACATGTTAGACTCCTTGGTCCGTGTTTCAAGACGGGTCGCTTAAGGC
       C2-NFSgF     CAAACACTCGCGCACATGTTAGACTCCTTGGTCCGTGTTTCAAGACGGGTCGCTTAAAGC Sbescii      CATTATGCCAGCATCCTAAGCGCGTACCGAGGGCGCGAACCCCGGCCAAAAGGCGCGCTG
    C2-TC-Orchid    CATTATGCCAGCATCCTAAGCGCGTACCGAGGGCGCGAACCCCGGCCAAAAGGCGCGCTG
          C2-TC     CATTATGCCAGCATCCTAAGCGCGTACCGAGGGCGCGAACCCCGGCCAAAAGGCGCGCTG
       C2-NFSgF     CATTATGCCAGTGTCCTAAGCACGTACCGAGGGCGCGAACCCCGGCCAAAAGGCGTGCTG Sbescii      CGTTCCTCAGTCCCAACTGAAGTATACAACAAGGGGTTATAACACTGCCCGAAGGCAGCC
    C2-TC-Orchid    CGTTCCTCAGTCCCAACTGAAGTATACAACAAGGGGTTATAACACTGCCCGAAGGCAGCC
          C2-TC     CGTTCCTCAGTCCCAACTGAAGTATACAACAAGGGGTTATAACACTGCCCGAAGGCAGCC
       C2-NFSgF     CATTCCTCGATCCCAACTGAGACATACAACAAGGGGCTATAACACTGCCCGAAGACAGCC Sbescii      ACCTCCCCAAGCCTTTCTCCTCCAGTCGAAACTGACGCTGACCCATCCTACGGAAAGTA
    C2-TC-Orchid    ACCTCCCCAAGCCTTTCTCCTCCAGTCGAAACTGACGCTGACCCATCCTACGGAAAGTA
          C2-TC     ACCTCCCCAAGCCTTTCTCCTCCAGTCGAAACTGACGCTGACCCATCCTACGGAAAGTA
       C2-NFSgF     ACATTCCCCAAGCCTTTTTCCCTCAATCGAAATCGACACTGACCCGTCGGACAGGAAATA Sbescii      CACCAGGCAGAAGCCAGGCTGAGTTCCGCAAGATGCGACTGACCTCAAACGCTTCCCTTT
    C2-TC-Orchid    CACCAGGCAGAAGCCAGGCTGAGTTCCGCAAGATGCGACTGACCTCAAACGCTTCCCTTT
          C2-TC     CACCAGGCAGAAGCCAGGCTGAGTTCCGCAAGATGCGACTGACCTCAAACGCTTCCCTTT
       C2-NFSgF     CACCAAGCAGAAGCAAGGCTGAATCCCGCCAGACGTGACTGACTCCAAACGCTTCCCTTT Sbescii      CAACAATTTCACGTACTGTTTCACTCTCTTTCCAAAGTGCTTTTCATCTTTCCCTCACGG
    C2-TC-Orchid    CAACAATTTCACGTACTGTTTCACTCTCTTTCCAAAGTGCTTTTCATCTTTCCCTCACGG
          C2-TC     CAACAATTTCACGTACTGTTTCACTCTCTTTCCAAAGTGCTTTTCATCTTTCCCTCACGG
       C2-NFSgF     CAACAATTTCACGTACTGTTTCACTCTCTTTCCAAAGTGCTTTTCATCTTTCCCTCACGG Sbescii      TACTTGTTCGCTATCGGTCTCTCGCCAATATTTA
    C2-TC-Orchid    TACTTGTTCGCTATCGGTCTCTCGCCAATATTTA
          C2-TC     TACTTGTTCGCTATCGGTCTCTCGCCAATATTTA
       C2-NFSgF     TACTTGTTCGCTATCGGTCTCTCGCCAATATTTA
```

FIG. 8A
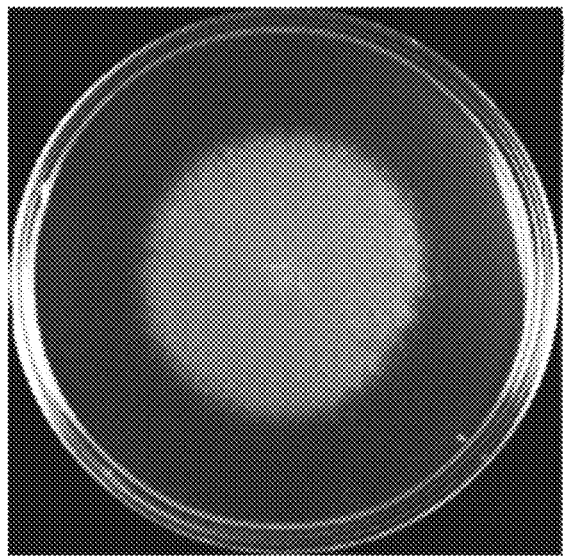 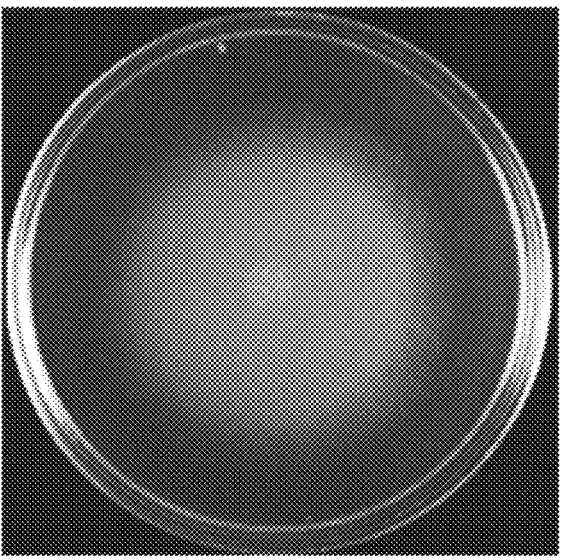

FIG. 8B
S vermifera
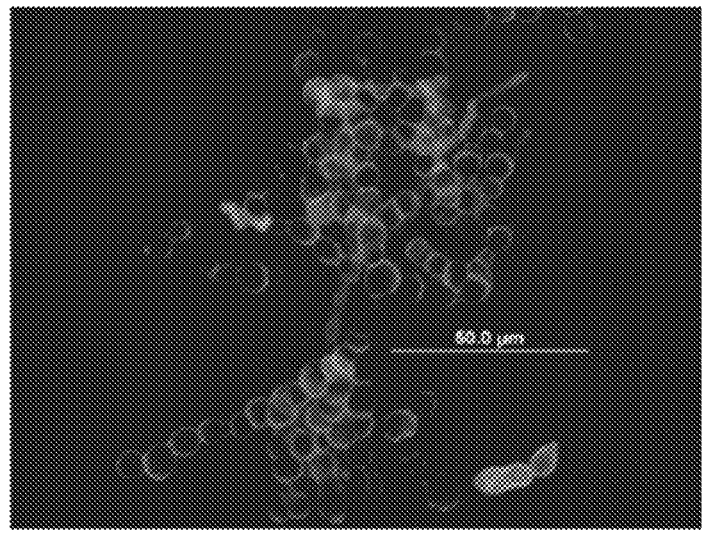
S bescii
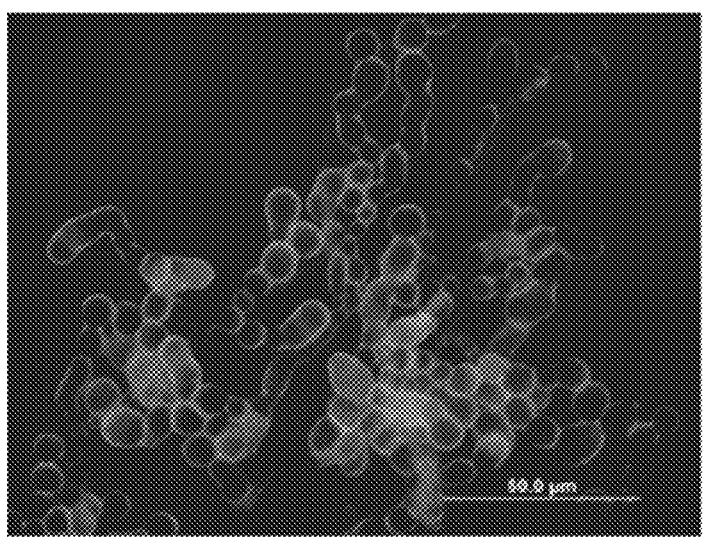

FIG. 8C
S vermifera
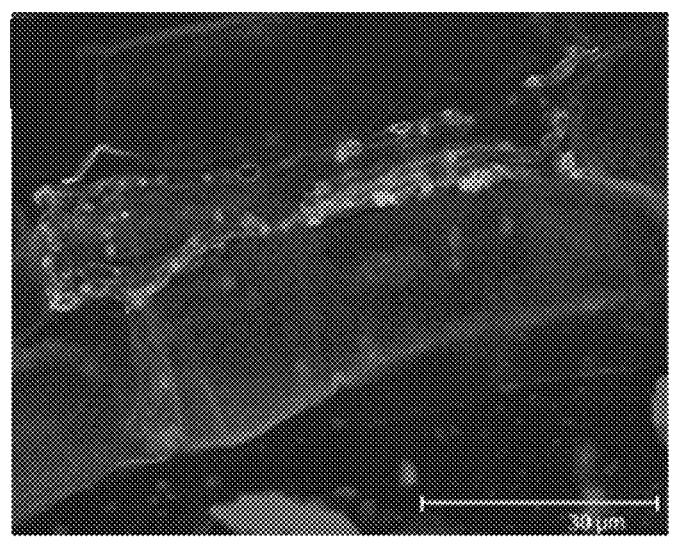
S bescii
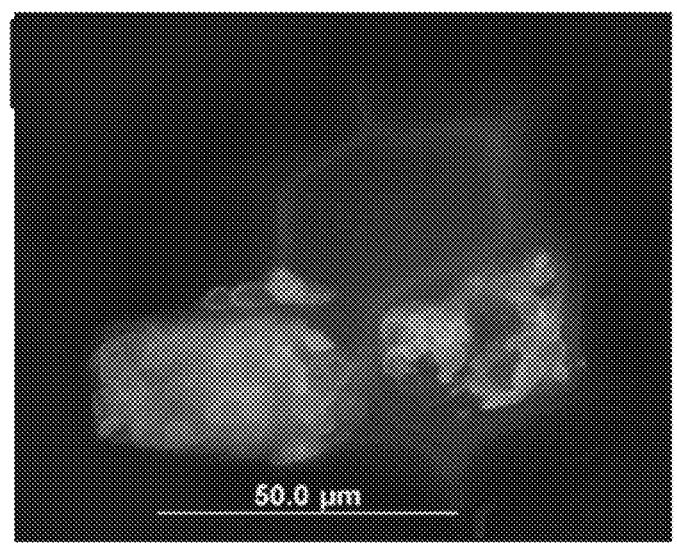

FIG. 21
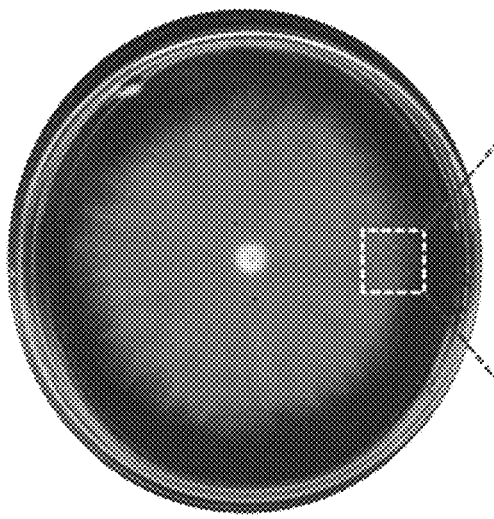
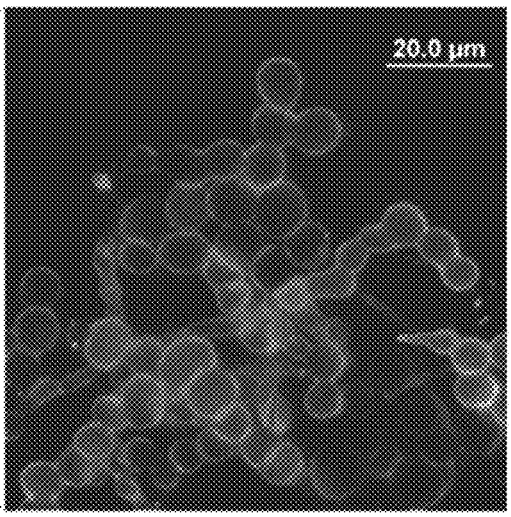
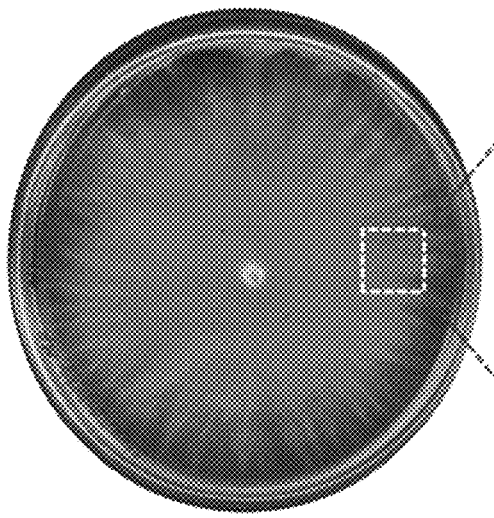
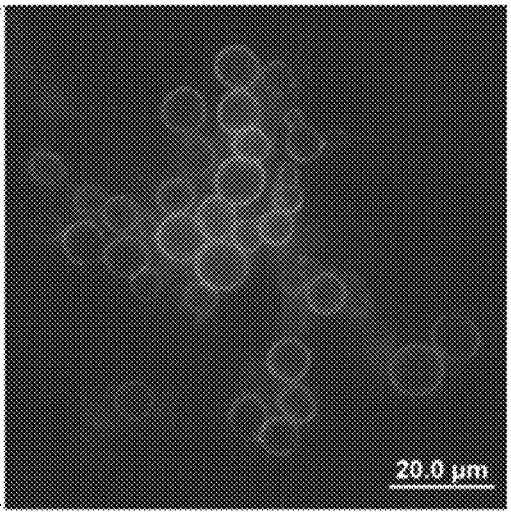

SEQUENCE LISTING

```
<160> NUMBER OF SEQ ID NOS: 22

<210> SEQ ID NO 1
<211> LENGTH: 698
<212> TYPE: DNA
<213> ORGANISM: Serendipita vermifera
<220> FEATURE:
<223> OTHER INFORMATION: ssp. bescii

<400> SEQUENCE: 1
cttggtcatt tagaggaagt aaaagtcgta acaaggtttc cgtaggtgaa cctgcggaag      60
gatcattaac gaatctaaag tcgatgcgtt gtgctggtgg caacacatgt gcacgcgtgt     120
cgcatacatc cacacacctg tgaaccytag actctgtggt cgatcgaacg cccggactcg     180
tccgtcgcrt gtggggactt trtgtcctcc gttcgcccag ggtaattttt acatacgccg     240
aatgtgatag aatgtatctg tgcataacgc gcaactaata caactttcaa caacggatct     300
cttggctctc gcatcgatga agaacgcagc gaaatgcgat aagtaatgtg aattgcagaa     360
ttcagtgaat catcgaatct tcgaacgcac cttgcgccct ttggtattcc gaagggcacg     420
cccgtttgag tgtcattgta atctcacctc cacggtttct tatcgtggtc gtggatctgg     480
acgtygtcgg cttgtcgacc cgtctgaaat gtatgagtgt accctgccgt gcagcgtatc     540
tggtgtgata agcatcttca ccggagtaat gcctcctttg gcgcgtctgt ggtgtgggct     600
ctgcgcttcg aaccgtcctc acaggacaat cttttgacrat ttgacctcag atcgggcggg     660
actacccgct gaacttaagc atatcaataa gcggagga                              698

<210> SEQ ID NO 2
<211> LENGTH: 61
<212> TYPE: DNA
<213> ORGANISM: Serendipita vermifera
<220> FEATURE:
<223> OTHER INFORMATION: ssp. bescii

<400> SEQUENCE: 2
ggtcgatcga acgcccggac tcgtccgtcg crtgtgggga ctttrtgtcc tccgttcgcc      60
c                                                                       61

<210> SEQ ID NO 3
<211> LENGTH: 19
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 3
gactcaacac gggaaactc                                                19

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gcccactaga aactctcacc                                               20

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
cttcttagag ggactgtcag ga                                            22

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
attcgcttta ccgcacaagg c                                             21

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tgagtgtcat tgtaatctca c                                             21

<210> SEQ ID NO 8
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ggtccgtgtt tcaagacgg                                                19

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 9
gagaccaaac tccggtgaaa                                                20

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
tgagcgtcat tgtaatctca c                                              21

<210> SEQ ID NO 11
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
actttgtgtc ctccgttcg                                                 19

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
tcctccgctt attgatatgc                                                20

<210> SEQ ID NO 13
<211> LENGTH: 634
<212> TYPE: DNA
<213> ORGANISM: Serendipita vermifera
<220> FEATURE:
<223> OTHER INFORMATION: ssp. bescii

<400> SEQUENCE: 13
ggttcgatta gtctttcgcc cctataccca aatttgacga tcgatttgca cgtcagaatc     60
gctacgagcc tccaccagag tttcctctgg cttcacccta ttcaggcata gttcaccatc    120
tttcgggtcc caacatatgc gctctgccgc agatgcgtca cagaaggtct gctccgggcg    180
ttggtgcaca agtacatgat cccaaccttt cactttcatt tcgcgctcgg gtttgacacc    240
caaacactcg cgcacatgtt agactccttg gtccgtgttt caagacgggt cgcttaaggc    300
cattatgcca gcatcctaag cgcgtaccga gggcgcgaac cccggccaaa aggcgcgctg    360
cgttcctcag tcccaactga agtatacaac aaggggttat aacactgccc gaaggcagcc    420
acctccccca agcctttctc ctccagtcga aactgacgct gacccatcct acggaaagta    480
caccaggcag aagccaggct gagttccgca agatgcgact gacctcaaac gcttcccttt    540
caacaatttc acgtactgtt tcactctctt tccaaagtgc ttttcatctt tccctcacgg    600
tacttgttcg ctatcggtct ctcgccaata ttta                                634

<210> SEQ ID NO 14

```
<211> LENGTH: 634
<212> TYPE: DNA
<213> ORGANISM: Serendipita sp.

<400> SEQUENCE: 14
ggttcgatta gtctttcgcc cctataccca aatttgacga tcgatttgca cgtcagaatc      60
gctacgagcc tccaccagag tttcctctgg cttcacccta ttcaggcata gttcaccatc     120
tttcgggtcc caacatatgc gctctgccgc agatgcgtca cagaaggtct gctccgggcg     180
ttggtgcaca agtacatgat cccaaccttt cactttcatt tcgcgctcgg gtttgacacc     240
caaacactcg cgcacatgtt agactccttg gtccgtgttt caagacgggt cgcttaaggc     300
cattatgcca gcatcctaag cgcgtaccga gggcgcgaac cccggccaaa aggcgcgctg     360
cgttcctcag tcccaactga agtatacaac aaggggttat aacactgccc gaaggcagcc     420
acctccccca agcctttctc ctccagtcga aactgacgct gacccatcct acggaaagta     480
caccaggcag aagccaggct gagttccgca agatgcgact gacctcaaac gcttcccttt     540
caacaatttc acgtactgtt tcactctctt tccaaagtgc ttttcatctt tccctcacgg     600
tacttgttcg ctatcggtct ctcgccaata ttta                                 634

<210> SEQ ID NO 15
<211> LENGTH: 634
<212> TYPE: DNA
<213> ORGANISM: Serendipita sp.

<400> SEQUENCE: 15
ggttcgatta gtctttcgcc cctataccca aatttgacga tcgatttgca cgtcagaatc      60
gctacgagcc tccaccagag tttcctctgg cttcacccta ttcaggcata gttcaccatc     120
tttcgggtcc caacatatgc gctctgccgc agatgcgtca cagaaggtct gctccgggcg     180
ttggtgcaca agtacatgat cccaaccttt cactttcatt tcgcgctcgg gtttgacacc     240
caaacactcg cgcacatgtt agactccttg gtccgtgttt caagacgggt cgcttaaggc     300
cattatgcca gcatcctaag cgcgtaccga gggcgcgaac cccggccaaa aggcgcgctg     360
cgttcctcag tcccaactga agtatacaac aaggggttat aacactgccc gaaggcagcc     420
acctccccca agcctttctc ctccagtcga aactgacgct gacccatcct acggaaagta     480
caccaggcag aagccaggct gagttccgca agatgcgact gacctcaaac gcttcccttt     540
caacaatttc acgtactgtt tcactctctt tccaaagtgc ttttcatctt tccctcacgg     600
tacttgttcg ctatcggtct ctcgccaata ttta                                 634

<210> SEQ ID NO 16
<211> LENGTH: 634
<212> TYPE: DNA
<213> ORGANISM: Serendipita sp.

<400> SEQUENCE: 16
ggttcgatta gtctttcgcc cctataccca aatttgacga tcgatttgca cgtcagaatc      60
gctacgagcc tccaccagag tttcctctgg cttcacccta ttcaggcata gttcaccatc     120
tttcgggtcc caacgtatac gctctaccgc ggatgcgtca cagaaggtct gctccgggcg     180
tcggtgcaca agtacatgtt cccgaccttt cactttcatt acgcgtccgg gtttgacacc     240
caaacactcg cgcacatgtt agactccttg gtccgtgttt caagacgggt cgcttaaagc     300
cattatgcca gtgtcctaag cacgtaccga gggcgcgaac cccggccaaa aggcgtgctg     360
cattcctcga tcccaactga gacatacaac aaggggctat aacactgccc gaagacagcc     420
```

```
acattcccca agccttttc cctcaatcga aatcgacact gacccgtcgg acaggaaata    480
caccaagcag aagcaaggct gaatcccgcc agacgtgact gactccaaac gcttcccttt    540
caacaatttc acgtactgtt tcactctctt tccaaagtgc ttttcatctt tccctcacgg    600
tacttgttcg ctatcggtct ctcgccaata ttta                                634

<210> SEQ ID NO 17
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
atcgaacgcc cggactcg                                                  18

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gctatcctga gggaaacttc                                                20

<210> SEQ ID NO 19
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
cttggtcatt tagaggaagt aa                                             22

<210> SEQ ID NO 20
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
tccgtaggtg aacctgcgg                                                 19

<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
atgactgtag gatctacctg acgg                                           24

<210> SEQ ID NO 22
<211> LENGTH: 17
<212> TYPE: DNA
<213> ORGANISM: Artificial Sequence
```

-continued

```
<220> FEATURE:
<223> OTHER INFORMATION: Description of Artificial Sequence: Synthetic
      primer

<400> SEQUENCE: 22
ccgcacaagg ctgataa                                                    17
```

SYMBIONT FOR ENHANCEMENT OF PLANT PERFORMANCE

CROSS-REFERENCE TO RELATED APPLICATIONS

The present application is a Continuation of International Application No. PCT/US18/64136, filed Dec. 5, 2018, which claims priority to U.S. Provisional Application No. 62/595,019, filed Dec. 5, 2017, the entirety of which is incorporated herein by reference.

STATEMENT OF GOVERNMENT INTEREST

This invention was made with Government support under DOE Prime Contract #DEAC05000R22725 awarded by the Department of Energy. The Government has certain rights in this invention.

SEQUENCE LISTING

The instant application contains a Sequence Listing which has been submitted electronically in ASCII format and is hereby incorporated by reference in its entirety. Said ASCII copy, created on Dec. 5, 2018, is named 17-21003-WO2_SL.txt and is 8,884 bytes in size.

BACKGROUND

Endophytes are typically fungal or bacterial organisms that live within or on plants. Fungal symbionts, such as mycorrhiza or certain clavicipitaceous foliar endophytes, survive within various host plant tissues, often colonizing the inter-cellular spaces of host's leaves, stems, flowers, or roots. These symbiotic endophyte-host relationships can provide fitness benefits to the host plant, such as enhancement of nutrient uptake or chemical defense from potential herbivores. Root-colonizing mycorrhizae often survive on photosynthetic carbohydrates from the plant, and in return, aid in the solubilization and uptake of water and minerals to the host, which can lead to the promotion of seed germination and plant growth. Additionally, the association of a fungal endophyte with a host plant often provides protection from pathogens or tolerance to a variety of biotic and abiotic stresses, such as insect infestation, grazing, water or nutrient deficiency, heat stress, salt of aluminum toxicity, and freezing temperatures. Host growth and fitness promotion and protection are thought to be achieved through multiple beneficial properties of the endophyte-host association. For instance, the endophytic organisms may produce growth-regulating substances to induce biomass production and alkaloids or other metabolites that have anti-insect and anti-herbivore properties. Additionally, fungal endophytes may directly suppress or compete with disease causing microbes, protecting the plant from potential pathogens.

Phosphorus (P) is an essential macronutrient required by all living organisms, participating in cell signaling and metabolism, and serving as a critical cellular building block. DNA, RNA, enzymes, phospholipids and phosphoproteins, sugar phosphates and energy-rich phosphorus compounds (e.g. ATP, NADP) which all require P. Elemental P can comprise up to 0.2% of a plant's dry weight. P is present in most biological systems as phosphate ($PO_4$; Pi), and the demand for P in agriculture is met primarily through mining inorganic rock phosphate. Unfortunately, rock phosphate is a non-renewable resource and reserves are dwindling in the face of growing industrial and agricultural needs, predicted to last 70-200 years at current consumption rates (approximately 15 MT P per year). Further, plants are relatively inefficient in their extraction of Pi from the soil, where it complexes with iron, calcium or other cations and becomes largely immobile. Soil microbes also rapidly absorb Pi to power their own metabolism(s) and to make microbial biomass, sequestering P in organic matter and away from the plant. These issues necessitate the application of excessive amounts of Pi to crop plants to get the desired growth impact. Much of what is not absorbed is lost to the global waterways where it causes eutrophication and massive algal blooms visible from space. The biological die-offs that follow affect entire trophic food chains and demonstrate the impact that misuse and overuse of rock phosphate have on planetary biodiversity.

Due to these limitations, efforts have been made to identify alternative P sources for agriculture. One of these, phosphite ($PO_3$; Phi), has multiple properties that make it potentially useful. As the formula suggests, Phi has one fewer oxygen atom than phosphate, a property that makes it less reactive with soil cations and enhances its solubility within the soil matrix. However, Phi is not naturally found in soil. Importantly, in aerobic environments Phi converts to Pi very slowly through natural oxidation, a process which may be accelerated somewhat in a living soil environment due to microbial activity. While this biological conversion is currently considered too slow and unregulated for Phi to compete with rock phosphate, more effectively managed these properties may not only make soil P more available to the plant, but deliver it in a slow-release form that can be more efficiently taken up. Indeed, plant Pi transporters have been shown to shuttle Phi as effectively as Pi, and the former is readily absorbed and translocated within the plant via the xylem and phloem.

Somewhat paradoxically, Phi itself can build up to toxic levels in plants, particularly when Pi is lacking or absent. These phytotoxic properties have even been capitalized on by marketing Phi as a weed herbicide (e.g. Phostrol from NuFarm America, USA). Even more studies have documented effective disease control against numerous plant pathogens through Phi application, particularly against oomycetes like *Pythium* and *Phytophthora*. Importantly, Phi is directly toxic to the oomycetes and can be active in the soil, or it can be translocated through the plant vasculature in sub-phytotoxic levels for demonstrable and robust protection of roots, and even leaves where it can prevent foliar infections. These protective properties of Phi have been utilized to develop multiple agrochemical products such as Aliette, marketed by Bayer Crop Science. Still further evidence exists that shows Phi's role as a general biostimulant in plants, although this benefit seems linked to sufficient soil Pi status. If Pi and Phi are present, the plant preferentially takes up Pi. If Pi is deficient, the phytotoxic effects of Phi are exacerbated, and instances where plant growth stimulation is observed may be due to disease control or microbial conversion of Phi to Pi. It seems likely that for effective utilization of the nutritive properties of Phi in most, if not all biological systems, it must ultimately be converted to Pi.

Endophytic relationships between non-pathogenic fungi and host plants are of agricultural interest, particularly in plants that serve as sources for food, feed, fiber and ornamentals for a global population. Whether monocots (e.g., corn, wheat, switchgrass, rice) or dicots (e.g., legumes, tomato, cotton), there is a need to improve one or more of the following: plant biomass and/or output yields, overall plant health and productivity, and promotion of host plant protection from and tolerance to biotic and abiotic stresses.

SUMMARY

The present disclosure provides a novel endophyte, *Serendipita vermifera* ssp. *bescii* ("*S. bescii*"), compositions and uses thereof and methods incorporating the use thereof for enhancement of plant performance.

The *S. bescii* endophyte of the present disclosure comprises a ribosomal DNA (rDNA) sequence comprising the nucleotide sequence of SEQ ID NO: 2. More specifically, the *S. bescii* endophyte of the present disclosure comprises a rDNA sequence comprising the nucleotide sequence of SEQ ID NO: 1 which contains the nucleotide sequence of SEQ ID NO: 2. These sequences are unique to *S. bescii*.

In some embodiments, a composition is provided which comprises a synthetic combination of the *S. bescii* endophyte and a source of phosphite.

In some embodiments, a coated plant seed is provided having a coating comprising a *S. bescii* endophyte and a source of phosphite.

In some embodiments, a synthetic combination of a seed, a *S. bescii* endophyte and a source of phosphite is provided.

In some embodiments, a combination is provided which includes a host plant containing a *S. bescii* endophyte and soil or a soil substitute comprising a source of phosphite.

In some embodiments, a method if provided for producing a coating plant seed by coating the plant seed with a composition comprising a *S. bescii* endophyte and a source of phosphite.

In some embodiments, methods for producing a *S. bescii*-containing plant are provided where a coated plant seed having a coating comprising a *S. bescii* endophyte in an amount effective to colonize at least a portion of the plant is planted and a fertilizer composition comprising a source of phosphite is added.

In some embodiments, methods for producing a *S. bescii*-containing plant are provided where a plant seed is planted in soil or a soil substitute and an inoculum comprising the *S. bescii* endophyte is applied as well as a fertilizer composition including a source of phosphite.

In some embodiments, methods are provided including the steps of applying an inoculum comprising the *S. bescii* endophyte to a host plant to yield an inoculated host plant and applying a fertilizer composition comprising a source of phosphite to the host plant.

In some embodiments, methods are provided for producing a *S. bescii*-containing plant where a first host plant is planted in soil or a soil substitute containing at least a portion of a second host plant that contained the *S. bescii* endophyte and applying a fertilizer composition comprising a source of phosphite to the first host plant.

In some embodiments, a host plant or seed produced by the methods of the present disclosure are provided.

In some embodiments, a kit is provided that includes a composition comprising the *S. bescii* endophyte and a fertilizer composition comprising a source of phosphite.

In some embodiments, a kit is provided comprising a plurality of coated plant seeds, each coated plant seed having a coating comprising the *S. bescii* endophyte, and a fertilizer composition comprising a source of phosphite.

In some embodiments, a method is provided for culturing *S. bescii* in a culture medium that comprises a source of phosphite.

Other objects, features and advantages of the present disclosure will become apparent from the following detailed description. It should be understood, however, that the detailed description and specific examples, while indicating specific embodiments of the invention, are given by way of illustration only, since various changes and modifications within the scope of the present disclosure will become apparent to those skilled in the art from this detailed description.

BRIEF DESCRIPTION OF THE DRAWINGS

The summary above, as well as the following detailed description of illustrative embodiments, is better understood when read in conjunction with the appended drawings. For the purpose of illustrating the present disclosure, exemplary constructions of the disclosure are shown in the drawings. However, the disclosure is not limited to specific methods and instrumentalities disclosed herein.

FIG. 4 depicts the pairwise multiple alignment of D1/D2 rDNA sequences between Serendipitoid sequences detected in switchgrass roots from field (NFSgF) (SEQ ID NO: 16), trap culture (TC) (SEQ ID NO: 15) and from a rhizobox (TC-Orchid) (SEQ ID NO: 14) with *S. bescii* axenic culture (SEQ ID NO: 13).

FIG. 8A shows micrographs colonies of the axenic cultures of *S. bescii* and *S. vermifera* (MAFF305830) on MMN agar. Scale bar=50.0 μm.

FIG. 8B shows fluorescent micrographs showing monilioid hyphae stained with WGA-AF® 488 of the axenic cultures of *S. bescii* and *S. vermifera* (MAFF305830) on MMN agar. Scale bar=50.0 μm.

FIG. 8C shows fluorescent micrographs showing the transverse section of colonized switchgrass root cells stained with WGA-AF® 488 and propidium iodide, colonized with *S. bescii* or *S. vermifera* (MAFF305830). Scale bar=50.0 μm (*S. bescii*); Scale bar=30.0 μm (*S. vermifera*).

FIG. 21 shows photographs of colonies of *S. bescii* grown on agar with phosphite or phosphate after 14 days with fluorescent micrographs of *S. bescii* for each. Scale bar=20.0 µm.

DESCRIPTION

Figure 1:
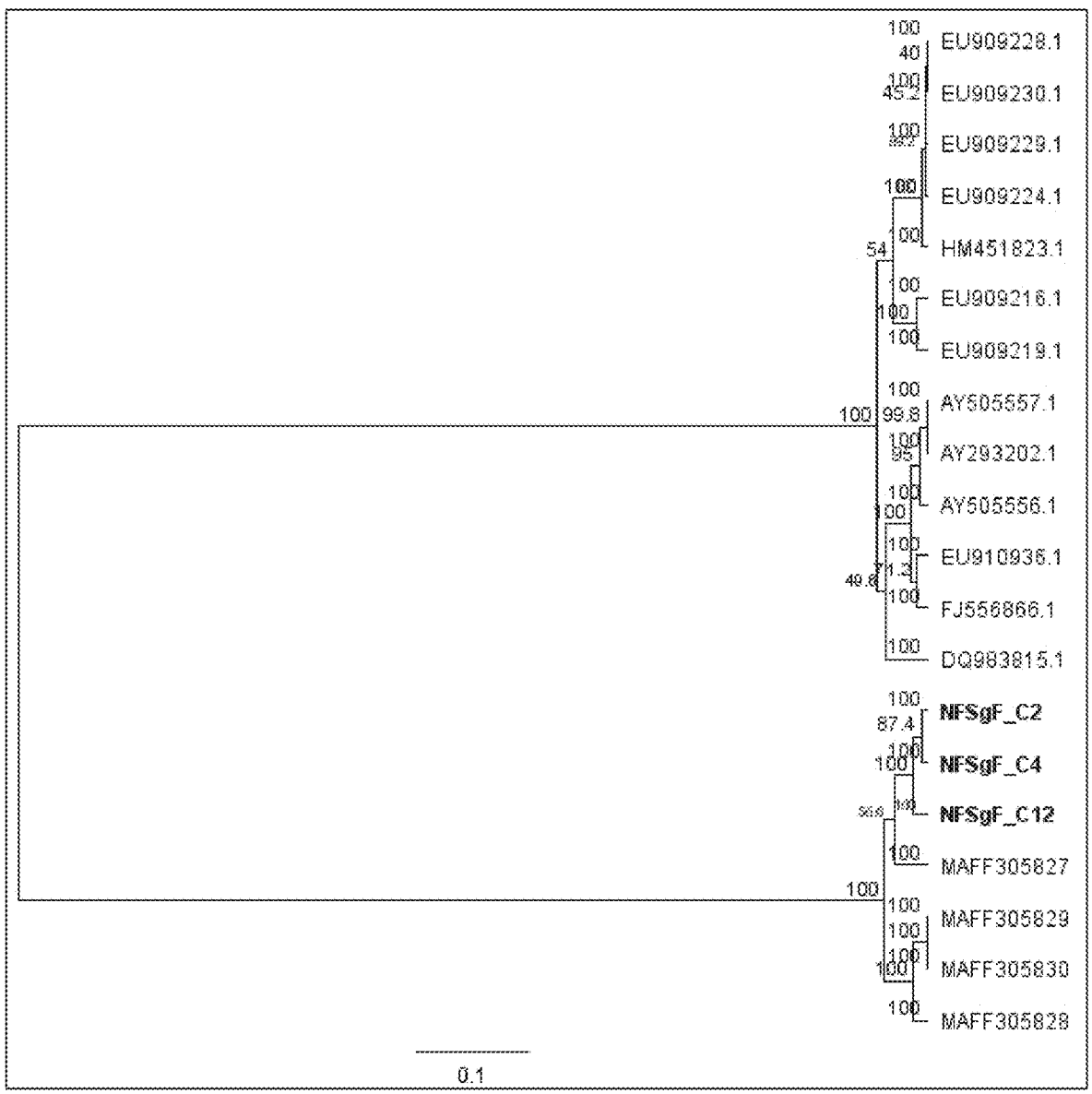
FIG. 1 depicts the phylogenetic relationship between three Serendipitoid sequences detected in switchgrass roots with serendipitoid sequences from GenBank and reference strains of *Serendipita vermifiera* (*S. vermifera*) isolated from Australian orchid reconstructed by the UPGMA method for 20 partial 18S/5.8S/partial LSU rDNA sequences (alignment length 750 bp). Numbers are UPGMA bootstrap values based on 500 replicates. The bar indicates substitutions per site.

The present disclosure describes particular embodiments and with reference to certain drawings, but the subject matter is not limited thereto. The drawings described are only schematic and are non-limiting. In the drawings, the size of some of the elements may be exaggerated or distorted and not drawn on scale for illustrative purposes. Where the elements of the disclosure are designated as "a" or "an" in first appearance and designated as "the" or "said" for second or subsequent appearances unless something else is specifically stated.

The present disclosure will provide description to the accompanying drawings, in which some, but not all embodiments of the subject matter of the disclosure are shown. Indeed, the subject matter may be embodied in many different forms and should not be construed as limited to the embodiments set forth herein, rather, these embodiments are provided so that this disclosure satisfies all the legal requirements.

Definitions

Certain terminology is used in the following description for convenience only and is not limiting. Certain words used herein designate directions in the drawings to which reference is made. Unless specifically set forth herein, the terms "a," "an" and "the" are not limited to one element, but instead should be read consistent with the meaning of "one or more," "at least one," and "one or more than one." As used herein "another" means at least a second or more. The terminology includes the words noted above, derivatives thereof and words of similar import.

The use of the term "or" in the claims is used to mean "and/or" unless explicitly indicated to refer to alternatives only or the alternatives are mutually exclusive.

Use of the term "about", when used with a numerical value, is intended to include +/−10%. For example, if a number of amino acids is identified as about 200, this would include 180 to 220 (plus or minus 10%).

Unless otherwise defined, all technical and scientific terms used herein have the same meaning as commonly understood by one of ordinary skill in the art.

As used herein, the term "biomass" means the total mass or weight, at a given time, of a plant or population plants, usually given as weight per unit area. The term may also refer to all of the plants or species in the community ("community biomass").

As used herein, the term "culture filtrate" means broth or media obtained from cultures inoculated with a strain of fungi and allowed to grow. The media is typically filtered to remove any suspended cells leaving the nutrients, hormones or other chemicals.

As used herein, the term "endophyte" refers to an organism capable of living in or on a plant or plant cell. An endophyte may refer to a fungal organism that may confer an increase in yield, biomass, resistance or fitness in its host plant. Fungal endophytes may occupy the intra-cellular, inter-cellular or extra-cellular spaces of plant tissue, including the leaves, stems, flowers, or roots.

As used herein, the term "host plant" means a plant which an endophytic fungi can colonize.

As used herein, the term "increased yield" refers to an increase in seed or fruit weight, seed or fruit size, output per plant, output per unit area (e.g., seeds, fruit, or weight of seeds or fruit per acre), bushels per acre, tons per acre, kilo per hectare. Additionally, the term may refer to an increase in plant height, number of internodes, grain side, amount of tillers, efficiency of nodulation and nitrogen fixation, efficiency of nutrient assimilation, resistance to biotic and abiotic stress, carbon assimilation, plant architecture, resistance to lodging, percent seed germination, seedling vigor, and juvenile traits. Other yield traits that can affect yield include, efficiency of germination (including germination in stressed conditions), growth rate (including growth rate in stressed conditions), composition of seed (e.g., starch, oil, protein) and characteristics of seed fill. Yield may be increased by at least 5%, 10%, 15%, 20%, 30%, 50%, 75%, 100% or more as compared to control plants under the same conditions.

As used herein, the term "phenotype" refers to detectable characteristics of a cell or organism, which characteristics are a manifestation of gene expression.

As used herein, the term "regeneration" refers to the process of growing a plant from a plant cell (e.g., plant protoplast, callus or explant).

As used herein, the term "synthetic combination" refers to a combination (also termed a "symbiotum") of a host plant and an endophyte which arises as the result of human intervention and which does not include a combination that occurred naturally. The combination may be achieved, by way of example but not limitation, by artificial inoculation, application or other infection of a host plant, whether a monocot or dicot plant, or host plant tissues with an endophyte. As used herein, the term "synthetic combination" as it pertains to the combination of phosphite and endophyte refers to a combination of phosphite or a material comprising phosphite and an endophyte wherein such combination arises as the result of human intervention and which does not include a combination that occurred naturally.

As used herein, the term "isolated endophyte of strain NFPB0129" or "*Serendipita bescii*" refers to a strain of the type deposited with the American Type Culture Collection (ATCC) under designation number PTA-124559. Samples of the *S. bescii* endophyte have been deposited by The Noble Research Institute with the ATCC at 10801 University Blvd., Manassas, Va. 20110 United States of America on Nov. 10, 2017 in conformance with the Budapest Treaty on the International Recognition of the Deposit of Microorganisms for the Purposes of Patent Procedure and assigned ATCC Designation (Accession number) PTA-124559 and Strain NFPB0129.

The present disclosure generally relates to a novel endophyte, *S. bescii*, uses thereof and methods incorporating the use thereof for enhancement of plant performance. The present disclosure also provides methods for detecting the presence of and identifying *S. bescii*.

The basidiomycetous species *Serendipita vermifera* is characterized primarily as an asexually reproducing mycorrhize isolated from orchids, for instance Australian orchids. Phylogenetic analysis has placed these endophytes within the order Serendipitaceae, based upon a maximum likelihood of phylogenetic analysis of nuclear rDNA encoding the ribosomal large subunit.

*S. vermifera* stains have also been isolated from orchid host plants and are known to one of skill in the art. The *S. bescii* endophyte of the present disclosure is a novel strain of *S. vermifera*. The *S. bescii* endophyte comprises an ITS sequence of SEQ ID NO: 1 which includes an indel domain of SEQ ID NO: 2, both of which are unique to the *S. bescii* endophyte. Throughout this disclosure, the *S. bescii* endophyte can be referred to as *Serendipita vermifera* ssp. *bescii*, *Serendipita bescii*, *Sebacina vermifera* ssp. *bescii*, *Sebacina bescii* and *S. bescii*. It should be understood that all of these terms are equivalent and refer to the same endophyte.

*S. bescii* colonizes the roots of plants and forms hyphal networks on and inside the root cells and inter-cellular spaces. These hyphae extend into the nearby rhizosphere and may form chlamydospores (survival structures) and may persist in soil upon decay of roots or root hairs. *S. bescii* strains can, therefore, be isolated from soil or host plants which are colonized with the fungal endophyte using isolation methods known in the art.

It has been found that colonization of a host plant by *S. bescii* can result in plant growth, such as an increase in biomass of 10% or more. Yield increases were also observed across multiple plant species, including switchgrass (*Panicum virgatum*), winter wheat (*Triticum aestivum*) and alfalfa (*Medicago sativa*). Each of these plants have the potential for a substantial economic impact in cultivation and production. Thus, *S. bescii* colonization of such plants has the potential to increase the overall productivity and commercial value of host plants, which produces a substantial and unexpected benefit. For example, switchgrass has been identified as a candidate for the production of ethanol or advanced biofuels. As the future need for renewable fuel alternatives increases, so does the need for more products crops and methods to increase the yield of candidate monocots, such as grasses. It has also been found that *S. bescii* can act as a soil conditioner by metabolizing organic matter in soil. Without being bound to theory, it is believed that the capacity of *S. bescii* to metabolize organic matter is responsible, at least in part, for its improved effects on host plants. Without being bound to theory, it is believed that the *S. bescii* genome includes a full complement of genes encoding cellulolytic enzymes and also includes urea transporters which may be responsible for these effects.

Surprisingly, it has been found that *S. bescii* is viable when grown on Phi and can convert Phi to Pi. By combining colonization of plants with *S. bescii* and fertilizing with phosphite, it has unexpectedly been found that the effective conversion of Phi to Pi in a targeted manner may be achieved to prevent buildup of Phi to a phytotoxic level in crop plants. Such an approach could endow the disease-suppressive benefits of Phi early (after "fertilizer" spread but prior to absorption), and the later nutritional benefits associated with its conversion to Pi in a more efficient, time-release manner targeted to the crop plant. If competing weedy species lack the beneficial microbe and are thus susceptible to Phi toxicity, reduced plant competition and weed suppression would be yet another benefit.

Without being bound to theory, by providing the *S. bescii* endophyte that can cover the root system and convert the Phi to Pi before entry or during initial entry into the roots, *S. bescii* could be ideally situated at the root surface, interfacing and mediating flux between rhizosphere soil, where fertilizer application would likely be made, and the root interior. The broad host range of *S. bescii* further maximizes its utility.

Pairing *S. bescii* with a second microbe, such as a soil endosymbiont bacterium that can actively convert Phi to Pi may present another solution.

In addition to the increased yields observed, the endophytic *S. bescii*/host plant combination has the potential to increase other attributes including, but not limited to, seed germination, plant fitness, and stress tolerance. These benefits can also contribute to increased biomass and/or seed (or fruit) production.

In some embodiments, a host plant infected with *S. bescii* displays increased biomass, vigor, stress tolerance, and/or productivity relative to a host plant of the same genotype that lacks the endophyte, when grown under substantially similar conditions. In some embodiments, the host plant can be an ornamental or used for food, feed or fiber and can be artificially inoculated with *S. bescii*. The combination of the host plant and *S. bescii* can provide protection to the host plant, in some instances a crop plant, from biotic stresses such as insect infestation, nematode infestation and/or herbivore grazing and/or abiotic stresses such as water deficiency, nutrient deficiency, heat stress, salt toxicity, aluminum toxicity, heavy metal toxicity and freezing temperatures. In some embodiments, the combination of the host plant and *S. bescii* can be more tolerant of stresses compared to a host plant of the same genotype lacking the *S. bescii* endophyte. Such stresses can include, by way of example but not limitation, biotic stress, pest stress, or insect stress. Examples of biotic stress include, but are not limited to, stress caused by a mammalian or insect herbivore or microbial pathogen (e.g., nematode, fungus, bacteria or virus).

In an embodiment, a method is provided for preparing an inoculum which includes providing particles of a carrier material, adding a fungal culture broth to the particles of the carrier material; and adding a *S. bescii* fungal mycelium derived from liquid broth culture to the fungal culture broth and particles of the carrier material followed by incubating the mixture of the *S. bescii* fungal mycelium derived from liquid broth culture, fungal culture broth and particles of the carrier material for a period of time. The mixture can then be dried. In some embodiments, the steps of adding a fungal culture broth to the particles of the carrier material and adding the *S. bescii* fungal mycelium derived from liquid broth culture to the fungal culture broth can be combined as a single step by providing a *S. bescii* culture in fungal culture broth to the particles of the carrier material. In some embodiments, the mixture can be shaken while incubating the mixture. The shaking can be performed at regular intervals during the period of time, such as, by way of example but not limitation, weekly. The period of time for incubation can be any period of time sufficient for growth of the *S. bescii* endophyte and/or to impregnate or coat the particles of carrier with the *S. bescii* endophyte. By way of example but not limitation, the period of time can be 6 weeks or 8 weeks. In some embodiments, prior to adding the particles of the carrier material, the carrier material can be sieved. By way of example but not limitation, sieving can be performed using a mesh size of 10 (2 mm). In certain aspects, the fungal culture broth and/or the particles of carrier material are sterile before adding the fungal mycelium derived from liquid broth culture. The drying step can be performed by any method, preferably a sterile method to prevent contamination of the carrier particles. In an embodiment, the drying can be air drying. The drying time can be any time sufficient to result in dry particles of carrier. In an embodiment, the drying can be overnight. In some embodiments, a composition comprises a fungal endophyte and a bentonite clay. In some aspects, the fungal endophyte is *S. bescii*.

In some embodiments, a method is providing for inoculating a host plant with an inoculum comprising a *S. bescii* endophyte by contacting the host plant with the inoculum under conditions sufficient to promote colonization of the roots of the host plant by the *S. bescii* endophyte. This method can result in colonization of the host plant by the *S. bescii* endophyte. Methods for inoculating can include, by way of example but not limitation, inoculation, infection, grafting and combinations thereof. The inoculum can be any composition which can provide the *S. bescii* endophyte to the host plant. By way of example, but not limitation, the inoculum can include a carrier material impregnated or coated with the *S. bescii* endophyte. In some embodiments, the inoculum can include portions of a plant infected with the *S. bescii* endophyte. In an embodiment, the portions of the plant infected with the *S. bescii* endophyte can be root cuttings. In an embodiment, the inoculum is a culture of *S. bescii*. In some embodiments, the inoculum comprises bentonite clay impregnated or coated with the *S. bescii* endophyte. In some embodiments, the inoculum is provided in an effective amount to result in colonization of the host plant by the *S. bescii* endophyte. In certain aspects, the host plant is a monocot. In some aspects, the host plant is a dicot. In certain aspects, the host plan can be a seed. In some embodiments, the inoculating is performed by contacting the inoculum with a portion of the host plant. In some aspects, the portion of the host plant is the roots of the host plant. In some embodiments, the inoculum can be sprayed onto living soil before planting the host plant or seed in the living soil. In some embodiments, the inoculating is performed by adding the inoculum to living soil in contact with the seed of a host plant. In some embodiments, the inoculating is performed by adding the inoculum to living soil in contact with the roots of the host plant. In an embodiment, the inoculum is added to living soil prior to planting a seed in the soil.

The inoculation of the host plant can be performed at any time during the plant life cycle. In some embodiments, the inoculum is added to living soil before planting the host plant. In some embodiments, the inoculum is added to the host plant simultaneously with planting the plant in living soil. For example, in an embodiment, seeds can be mixed with the inoculum, such as bentonite clay particles impregnated with the *S. bescii* endophyte and planted in living soil. In some embodiments, this can be accomplished by a spray application or aggregating the seeds with the inoculum. In some embodiments, the *S. bescii* endophyte can be coated on a carrier. In some embodiments, the inoculum is added to the host plant in living soil after germination of the host plant. For example, in an embodiment, alfalfa can be supplemented with phosphorous after germination, at which time the inoculum can be added to colonize the alfalfa host plant. It should also be understood, that inoculation of a host plant or seed can be performed in artificial media such that the host plant becomes colonized by the *S. bescii* endophyte. Such a plant can be subsequently planted in living soil. In an embodiment, a composition comprising bentonite clay and *S. bescii* can be placed in soil followed by planting a seed under conditions sufficient to promote colonization of the roots of the host plant.

In some embodiments, the carrier forms a seed coat on a seed. In an embodiment, a synthetic combination of a *S. bescii* endophyte and a host plant, comprises the *S. bescii* endophyte in a seed coat which coats the seed.

In some embodiments, the synthetic combination of the *S. bescii* endophyte with a host plant can positively influence the agronomic qualities of the host plant. Such agronomic qualities can include, but are not limited to, increased root and/or shoot biomass, increased tillering, increased root mass, increased flowering, increased seed yield, and enhanced resistance to biotic and/or abiotic stresses. In some embodiments, the agronomic qualities are increased compared to plants of the same genotype grown under the same conditions but lacking the *S. bescii* endophyte. The combination of *S. bescii* and a host plant can protect the host plant from biotic and/or abiotic stresses which can include, by way of example but not limitation, drought (water deficit), cold, heat stress, nutrient deficiency, salt toxicity, aluminum toxicity, heavy metal toxicity, grazing by herbivores, insect infestation, nematode infection and fungal infection. The combination can also improve a host plant's ability to resist, tolerate and/or overcome pathogens. For example, the enhanced resistance which is provided by the endophyte can protect the host plant from subsequent infection by other fungal diseases, such as root rot, powdery mildew, *Fusarium* blight, *Pythium* blight, leaf spot, rust and snow mold. This resistance can allow for improved biomass or seed yield relative to plants not colonized by the *S. bescii* endophyte.

In some embodiments, a method is provided for identifying a microorganism as *S. bescii* in a sample. The method includes the steps of performing a polymerase chain reaction (PCR) on the sample using primers suitable to amplify an internal transcribed spacer (ITS) region of Serendipitaceae including a 3' portion of the 18S sequence or portion thereof, sequencing the product, if any, obtained, and comparing the sequence obtained with SEQ ID NO: 1 and/or SEQ ID NO: 2 to determine whether the microorganism is *S. bescii* based on homology between the sequence of the product of the PCR and SEQ ID NO: 1 and/or SEQ ID NO: 2. In an embodiment, the primers have the nucleotide sequences of SEQ ID NO: 19 (ITS1F) and SEQ ID NO: 12 (ITS4), respectively. In some embodiments, the PCR is a nested PCR.

In some embodiments, a method for identifying a microorganism as *S. bescii* in a sample can include the steps of performing a PCR on the sample using primers specific for *S. bescii* and determining if the sample contains *S. bescii* if a PCR product is obtained. In an embodiment, the *S. bescii* specific primers have nucleotide sequences of SEQ ID NO: 11 and SEQ ID NO: 12, respectively.

In some embodiments, a method is provided for identifying a microorganism as *S. bescii* in a sample comprising performing a PCR on the sample with primers suitable to amplify the ITS region of the ribosomal DNA of Serendipitaceae. It will be appreciated by one of ordinary skill in the art that different combinations of primers can amplify any region of DNA comprising the ITS region and 3' portion of the 18S sequence of the ribosomal DNA or a portion thereof. It will also be appreciated that the PCR product using different combinations of primers can include all or a portion of SEQ ID NO: 1 and SEQ ID NO: 2 or a corresponding portion thereof which can be analyzed to identify *S. bescii* in a sample by comparison to SEQ ID NO: 1 and/or SEQ ID NO: 2.

It should be understood that any method for detecting the presence of specific nucleic acid and/or amino acid sequences associated with the presence of *S. bescii* can be used to determine whether an endophyte is *S. bescii* and/or whether a sample contains *S. bescii*. Such methods can include isolation of total DNA from tissues of a potential plant-endophyte combination, followed by PCR, or alternatively, Southern blotting, western blotting or other methods known in the art. In addition, biochemical methods such as ELISA, HPLC, TLC and/or fungal metabolite assays can be utilized. Methods of identification can also include microscopic analysis, such as root staining, or culturing methods, such as grow out tests or other methods known in the art. In some embodiments, the roots of a potential host plant-endophyte combination can be stained with fungal specific stains, such as WGA-AF® 488 and microscopically assayed to determine fungal root associates.

In some embodiments, a composition is provided which comprises a synthetic combination of the *S. bescii* endophyte and a source of phosphite. In certain aspects, the composition further comprises a carrier material. Such compositions can be used as plant fertilizers, non-toxic pesticides or seed coatings. Methods for coating seeds are well known to those of skill in the art. In some embodiments, where the composition is used as a seed coating for a plant seed, the *S. bescii* endophyte is present in an amount effective to colonize a plant grown from the plant seed.

In some embodiments, a coated plant seed is provided having a coating which comprises a *S. bescii* endophyte and a source of phosphite. In certain aspects, the coating can further comprise a carrier material. In some embodiments, the *S. bescii* endophyte is present in said coating in an amount effective to colonize a plant grown from the plant seed.

In some embodiments, a synthetic combination of a seed, a *S. bescii* endophyte and a source of phosphite is provided.

In some embodiments, a combination is provided which includes a host plant containing a *S. bescii* endophyte and soil or a soil substitute comprising a source of phosphite. In some embodiments, the host plant is not switchgrass. In certain aspects, the host plant containing the *S. bescii* can endophyte can have the ability to convert phosphate.

In some embodiments, a method is provided for producing a coated plant seed which includes a step of coating a plant seed with a composition comprising a *S. bescii* endophyte and a source of phosphite. In certain aspects, the coating of the plant seed with the *S. bescii* endophyte and the source of phosphite can be performed in separate steps. For example, the coating with phosphite may applied separately from the coating with the *S. bescii* endophyte while still yielding a coated plant seed where the coating of the plant seed comprises both the *S. bescii* endophyte and the source of phosphite. In certain aspects, the coating is performed by contacting the plant seed with the composition. Methods for producing coated seeds are well known to those of skill in the art. By way of example, but not limitation, methods for coating seeds can include spray drying, dip coating, soaking and dusting. In some embodiments, the composition can be a suspension of mycelia of *S. bescii* in a diluent. Any suitable diluent can be used, such as, by way of example but not limitation, a xantham gum solution such as a 0.2% xanthan gum solution. Other diluents that can be used, by way of example but not limitation, include polyvinylpyrrolidone 40K, canola oil, starch such as from waxy maize, methylcellulose slurry, and combinations thereof. In some embodiments, seeds produced by such methods are provided. Methods for coating with such materials are well known. Exemplary methods are disclosed by Swaminathan, J. et al., J. Applied Microbiology 120(2):425-431 (2015). In some embodiments, *S. bescii*-containing host plants from such coated plant seeds are provided.

In some embodiments, methods for producing a *S. bescii*-containing plant are provided. Inoculation methods using fungal endophytes are well known in the art. A *S. bescii*-containing plant can be produced by inoculating the plant at any stage, including, by way of example but not limitation, as a seed, seedling or mature plant. Inoculation can be performed by any suitable method, including, by way of example but not limitation, broadcast spraying, liquid or dry application in-furrow, dusting said soil or soil substitute with said inoculum, direct incorporation into the soil or soil substitute, and application of granules of the inoculum. Where a fertilizer composition or inoculum is applied, it can be applied to a plant or to the surrounding soil or soil substitute.

In some embodiments, a method is provided which includes planting a coated plant seed having a coating comprising a *S. bescii* endophyte in an amount effective to colonize at least a portion of the plant grown from said seed in soil or a soil substitute and applying a fertilizer composition comprising a source of phosphite to the soil or soil substitute. The fertilizer composition can be applied before planting the coated plant seed, at the same time as planting the coated plant seed or at a time after planting the coated plant seed. The fertilizer composition can also be re-applied. In some embodiments, the fertilizer composition can further comprise the *S. bescii* endophyte. In some embodiments, the fertilizer composition can be a part of the coating of the coated plant seed. In some embodiments, the method can further include allowing the coated plant seed to grow into a plant under conditions sufficient for colonization of at least a portion of the plant by the *S. bescii* endophyte. In some embodiments, the portion of the plant is the root tissue. In some embodiments, the portion of the plant is the shoot tissue. In some embodiments, seeds from such plants are also provided.

In some embodiments, a method is provided which includes planting a plant seed in soil or a soil substitute. The method further includes applying an inoculum comprising the *S. bescii* endophyte in an amount sufficient to colonize a plant grown from the plant seed to the soil or soil substitute and applying a fertilizer composition which includes a source of phosphite to the soil or soil substitute. In some embodiments, the inoculum is applied before the seed is planted. In some embodiments, the inoculum is applied at the time the seed is planted. In some embodiments, the inoculum is applied at a time after the seed is planted. The fertilizer composition can be applied at any time before, during or after planting and can be re-applied. In some embodiments, the fertilizer composition can further comprise the *S. bescii* endophyte.

In some embodiments, a method is provided which includes applying an inoculum comprising the *S. bescii* endophyte to a host plant to yield an inoculated host plant and applying a fertilizer composition comprising a source of phosphite to the host plant. In some embodiments, the application of the inoculum can be via dip coating the plant prior to planting in soil or a soil substitute. In some embodiments, the application of the inoculum can occur while the plant is present in soil or soil substitute and by any suitable method in accordance with the present disclosure. In some embodiments, the inoculum is applied in an amount effective to colonize at least a portion of the host plant. In some embodiments, the inoculum is applied under conditions sufficient to promote colonization of the at least a portion of the host plant. In some embodiments, the portion of the host plant is the root tissue. In some embodiments, the portion of the host plant is the shoot tissue.

In some embodiments, a method for producing a *S. bescii*-containing plant can include planting a first host plant in soil or a soil substitute comprising at least a portion of a second host plant which contained the *S. bescii* endophyte and applying a fertilizer composition comprising a source of phosphite.

The present disclosure also provides for a host plant containing the *S. bescii* endophyte from any of the foregoing methods that yield an inoculated host plant. The present disclosure also provides for seeds obtained from said host plants.

In some embodiments, a kit is provided that includes a composition comprising the *S. bescii* endophyte and a fertilizer composition comprising a source of phosphite. In some embodiments, a kit is provided comprising a plurality of coated plant seeds, each coated plant seed having a coating comprising the *S. bescii* endophyte, and a fertilizer composition comprising a source of phosphite. In some embodiments, the composition comprising the *S. bescii* endophyte can further comprise a carrier. In some embodiments, the coating on each coated plant seed can further comprise a carrier.

A method for culturing *S. bescii* is also provided that includes culturing the *S. bescii* endophyte in a culture medium comprising a source of phosphite. In some embodiments, the culture medium is a liquid. In some embodiments, the culture medium is solid.

In any of the foregoing embodiments, unless otherwise specified, the *S. bescii* endophyte can be present in a composition or inoculum in any suitable form. Such forms can include, by way of example but not limitation, mycelia, mechanically fractured hyphae, root cuttings from a *S. bescii*-containing plant, and a *S. bescii* culture. In certain aspects, the *S. bescii* can be present in the inoculum associated with a carrier, such as by way of example but not limitation, bentonite clay particles harboring *S. bescii*. Application of inoculum can be either to a plant directly or to the surrounding soil or soil substitute. In some embodiments, the inoculum can be applied to the plant prior to planting in soil or a soil substitute. In any of the foregoing embodiments, the inoculum can be in any form, including by way of example but not limitation, a liquid, solid, powder, dust, dispersion, granules or suspension. Such forms can be used in various application methods to the extent that they are compatible. For example, liquid inoculum can be broadcast sprayed.

It should be understood that the carrier material of any of the foregoing embodiments can include any material which can be impregnated or coated with the *S. bescii* endophyte and which does not prevent growth of the *S. bescii* endophyte. In some embodiments, the carrier material is a porous material. In some aspects, the carrier material is an inorganic matrix material. In some aspects, the carrier material is charcoal. In certain aspects, the inorganic matrix material is bentonite clay. Carrier materials are well known and can include, by way of example but not limitation, organic carriers such as charcoal and inorganic matrix materials such as bentonite clay. In some embodiments, the carrier is impregnated or coated with *S. bescii* endophyte.

In any of the foregoing embodiments, the source of phosphite can be any source of phosphite but does not include phosphate or compounds containing phosphate. By way of example, but not limitation, the source of phosphite can be a phosphite compound or a phosphonate compound.

In any of the foregoing embodiments, a plant seed can be a plant seed of a monocot or dicot. In any of the foregoing embodiments, a host plant can be a monocot or dicot. By way of example but not limitation, such monocots include wheat (*Triticum aestivum*), durum wheat (*Triticum turgidum* ssp. *durum*), tall wheatgrass (*Thinopyrum ponticum*), western wheatgrass (*Pascopyrum smithii*), maize (*Zea mays*), rice (*Oryza sativa*), sorghum (*Sorghum bicolor*), onion (*Allium cepa*), asparagus (*Asparagus officinalis*), miller (*Gramene* spp.), meadow fescue (*Festuca pratensis*), tall fescue (*Festuca arundinacea*), cereal rye (*Secale cereal*) Russian wild rye (*Psathyrostachys juncea*), oats (*Avena sativa*), bermudagrass (*Cynodon dactylon*), Kentucky bluegrass (*Poa pratensis*), big bluestem (*Andropogon gerardii*), little bluestem (*Schizachyrium scoparium*), blue grama (*Bouteloua gracilis*), black grama (*Bouteloua eriopoda*), side-oat grama (*Bouteloua curipendula*), johnsongrass (*Sorghum halepense*), buffalograss (*Buchloe dactyloides*), and creeping bentgrass (*Agrostis stolonfera*). In some aspects, the host plant is defined as a monocot. In certain aspects, the host plant is a monocot that produces food. In certain aspects, the host plant is a monocot that produces feed or grazing material for livestock. In one embodiment, the host plant is a grass host plant such as switchgrass (*Panicum virgatum*). In some embodiments, the host plant is not switchgrass. By way of example but not limitation, such dicots include alfalfa (*Medicago sativa*), rose (*Rosa* spp.), tomato (*Solanum lycopersicum*), blueberry (*Vaccinium* spp.), cotton (*Gossypium hirsutum*), pepper (*Capsicum* spp.), common bean (*Phaseolus vulgaris*), lentil (*Lens culinaris*), peas (*Pisum sativum*), eggplant (*Solanum melongena*), watermelon (*Citrullus lanatus*), coffee (*Coffea* spp.), apples (*Malus domestica*), plums (*Prunus domestica*), sweet cherry (*Prunus avium*), squash (*Cucurbita pepo* L.), broccoli (*Brassica oleracea*), turnips (*Brassica rapa*), geraniums (*Geranium* spp.), strawberry (*Fragaria×ananassa*), soybean (*Glycine max*), and pecan (*Carya illinoinensis*). In an embodiment, the host plant is pecan. In some embodiments, the pecan is chosen from the Kanza, Peruque and Giles cultivars. In an embodiment, the host plant is defined as a dicot. In some embodiments, the host plant is an ornamental. In some embodiments, the host plant is a dicot crop that produces human good. In certain aspects, the host plant is a dicot crop that produces feed or grazing material for livestock. In an embodiment, the host plant is alfalfa (*Medicago sativa*).

In any of the foregoing embodiments, a host plant colonized by or containing the *S. bescii* endophyte can have the ability to convert phosphite to phosphate. Without being bound to theory, it is believed that the *S. bescii* endophyte can convert phosphite to phosphate while in or on the plant and in the surrounding soil or soil substitute. In some embodiments, a host plant of the same species that is not colonized by or contains the *S. bescii* endophyte does not have the ability to convert phosphite to phosphate. In some embodiments, the host plant colonized by or containing the *S. bescii* endophyte can have an increased ability to convert phosphite to phosphate relative to a host plant of the same species that is not colonized by and does not contain the *S. bescii* endophyte.

In any of the foregoing embodiments, it should be understood that colonization of a plant by *S. bescii* can include colonization of any portion of the plant. In certain aspects, the *S. bescii* endophyte colonizes only a portion, such as a specific tissue of the plant. By way of example, but not limitation, the roots of a plant can be colonized by the endophyte while other tissues are not colonized.

In any of the foregoing embodiments, a host plant colonized by or containing the *S. bescii* endophyte can exhibit increased uptake of phosphite relative to a host plant of the same species that is not colonized by and does not contain the *S. bescii* endophyte. In some embodiments, the increased uptake can be measured in the shoot tissue of the host plant. In some embodiments, the increased uptake can be measured in the root tissue of the host plant. In any of the foregoing embodiments, a host plant colonized by or containing the *S. bescii* endophyte can exhibit increased conversion of phosphite to phosphate relative to a host plant of the same species that is not colonized by and does not contain the *S. bescii* endophyte.

In any of the foregoing embodiments, a fertilizer composition and inoculum or composition comprising the *S. bescii* endophyte can be combined in a single composition and applied concomitantly. For example, without limiting the present disclosure, in kits of the present disclosure, the fertilizer composition and the composition comprising the *S. bescii* endophyte can be combined in a single formulation.

In any of the foregoing embodiments, a fertilizer composition can be substantially free of phosphate. In some embodiments, a fertilizer composition does not contain phosphate. In any of the foregoing embodiments, the plant is not switchgrass.

In any of the foregoing embodiments where a coated plant seed is provided or produced, the coating can further comprise a material selected from xanthan gum, polyvinylpyrrolidone 40K, canola oil, starch, methylcellulose slurry and combinations thereof.

It should be understood that, in some embodiments, the *S. bescii* endophyte of the present disclosure comprises the nucleotide sequence of SEQ ID NO: 1, which also includes the nucleotide sequence of SEQ ID NO: 2. In some embodiments, the *S. bescii* endophyte comprises the nucleotide sequence of SEQ ID NO: 2. However, this disclosure is intended to include the *S. bescii* endophyte as modified, where modification(s) to the sequence of SEQ ID NO: 1 or SEQ ID NO: 2 are made artificially. Thus, *S. bescii* strains derived from a *S. bescii* endophyte having the nucleotide sequence of SEQ ID NO: 2 or SEQ ID NO: 1 are within the contemplated scope of the present disclosure. In some embodiments, a *S. bescii*-derived endophyte can comprise a nucleotide sequence with 50, 60, 70, 80, 85, 90, 95, 96, 97, 98, or 99% homology to the nucleotide sequence of SEQ ID NO: 1. In some embodiments, a *S. bescii*-derived endophyte can comprise a nucleotide sequence with 50, 60, 70, 80, 85, 90, 95, 96, 97, 98, or 99% homology to the nucleotide sequence of SEQ ID NO: 2. It should be further understood that the present disclosure and embodiments disclosed herein encompass the use of any *S. bescii* endophyte and any mutant thereof that functions in substantially the same way.

It should be understood that the foregoing description provides embodiments of the present invention which can be varied and combined without departing from the spirit of this disclosure. To the extent that the different aspects disclosed can be combined, such combination are disclosed herein.

The following examples are included to demonstrate preferred embodiments of the present disclosure. Those of skill in the art should, in light of the present disclosure, appreciate that many changes can be made in the specific embodiments which are disclosed and still obtain a like or similar result without departing from the concept, spirit and scope of the present disclosure.

EXAMPLES

Example 1: Isolation and Characterization of *Serendipita bescii* from Switchgrass Root Samples 63 root samples were collected from switchgrass plants collected from Noble Research Institute's switchgrass field located in Ardmore, Okla., United States (coordinates 34.193389, −97.086004). The switchgrass plants were originally collected from the Tallgrass Prairie Preserve (TGPP) located in Northern Oklahoma and planted in the Noble Foundation Research Institute's switchgrass plot in Oklahoma. The switchgrass plant denoted as C2 (also known as 7W in the Noble Research Institute's switchgrass field), from which *S. bescii* was isolated as described below, was originally located at coordinates 36.8102, 97.527 and the switchgrass plant denoted as C4 (also known as 31E in the Noble Research Institute's switchgrass field) was originally located at coordinates 36.76877, 96.39035. The root samples were thoroughly washed in running water to remove adhered soil particles. Root samples from each plant were treated individually. Cleaned root samples were cut into 1 cm pieces, homogenized and divided into two samples. The first sample was subjected to DNA extraction while the second sample was blot dried and maintained at 4° C. for downstream processing.

The first sample for each root sample was ground in liquid nitrogen in a TissueLyser II (Retsch, Germany). gDNA was extracted from the lyophilized tissue using a QIAGEN MagAttract 96 DNA Plant Core Kit according to the manufacturer's instructions and quantified using a Nanodrop ND-1000 (Wilmington, Del., United States). The 3' region of the 18S (SSU), ITS1 and ITS2, the 5.8S ribosomal subunit and the 25-28S (LSU) of Serendipitaceae were amplified by direct PCR using the primers NS23 (SEQ ID NO: 3) and NLSeb2R (SEQ ID NO: 4). Each 25 µl PCR reaction included 12.5 µl GO TAQ GREEN MASTER MIX®, 1.25 µl of each primer (0.5 µM) and 10 ng of total genomic DNA. Negative controls containing all reagents except the genomic DNA template were used in all PCR arrays.

Thermocycling was performed using initial heating at 94° C. for 2 minutes, followed by 30 cycles of denaturation at 94° C. for 45 seconds, annealing at 60° C. for 45 seconds and extension at 72° C. for 2.5 minutes. The final extension was performed at 72° C. for 10 minutes. The presence and yield of PCR products were monitored by agarose gel electrophoresis followed by visualization with ethidium bromide staining and UV illumination.

Using direct PCR, it was possible to amplify a ~2.2 kb fragment. PCR of the root samples yielded 36 out of 63 samples with a ~2.2 kb fragment with 27 samples yielding no PCR product. The PCR product was subsequently gel purified using the QIAguick Gel Extraction Kit® and submitted for sequencing using the same set of primers at Noble Research Institute's genomics Core Facility. DNA sequences were manually inspected, edited using geneious version 6.1.2 (Biomatters Auckland, New Zealand). The sequences were then subjected to BLASTn searches against the NCBI nonredundant database (GenBank) for sequence identities with known Serendipita sequences. Out of the 36 samples, three sequences were identified as closely related to Serendipitaceae sequences from GenBank. The phylogenetic affinities of these three sequences, designated NFSgF_C2, NFSgF_C4 and NFSgF_C12, with known serendipitoid sequences from GenBank and reference strains from S. vermifera isolated from Australian orchid were determined by the UPGMA method as shown in FIG. 1.

To purify and eventually increase the percent colonization or relative abundance of Serendipita biomass in planta, the trap culture method was used in the switchgrass (Panicum virgatum_L) cultivar Alamo as a host. Surface sterilized root materials, known to have been infected with Serendipita on the basis of the foregoing sequence analysis were finely chopped and mixed with steile Metromix-350 medium (Scotts-Sierra Horticultural Products, Marysville, Ohio, United States). D25L single cell root trainers (5 cm diameter and 25 cm height, Stuewe & Sons, Inc., Oregon, United States) were filled with this mixture. Each root trainer was potted with a single in vitro germinated sterile seedling of switchgrass cultivar Alamo. The plants were maintained in a greenhouse for 4-5 months.

Figure 2:
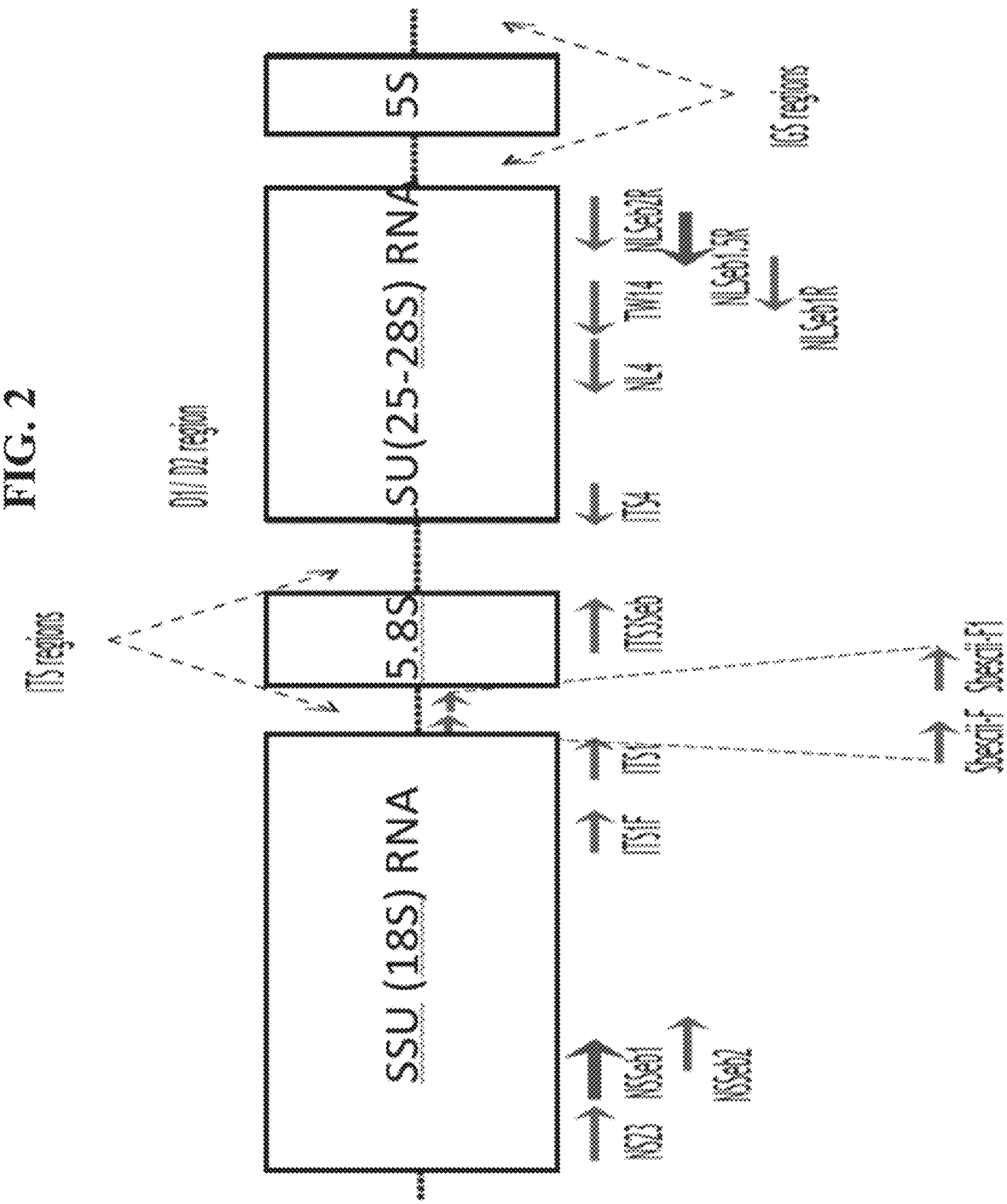
FIG. 2 depicts a map of ribosomal DNA of Serendipitaceae with exemplary primers for amplifying portions thereof by PCR. Exemplary forward primers include NS23 (SEQ ID NO: 3), NSSeb1 (SEQ ID NO: 5), NSSeb2 (SEQ ID NO: 21), ITS1F (SEQ ID NO: 19), ITS1 (SEQ ID NO: 20), Sbescii-F (SEQ ID NO: 17), Sbescii-F1 (SEQ ID NO: 11) and ITS3Seb (SEQ ID NO: 7). Exemplary reverse primers include ITS4 (SEQ ID NO: 12), NL4 (SEQ ID NO: 8), TW14 (SEQ ID NO: 18), NLSeb2R (SEQ ID NO: 4), NLSeb1.5R (SEQ ID NO: 6), and NLSeb1R (SEQ ID NO: 22). Sbescii-F1 (SEQ ID NO: 11) and Sbescii-F (SEQ ID NO: 17) are specific to *S. bescii*.

After 4-5 months of greenhouse culture, colonization of Serendipitaceae was confirmed by nested PCR using sets of Serendipita specific primers. A map of the genetic sequence of the ribosomal DNA of Serendipita is shown in FIG. 2 aligned with primers that can be used to amplify portions of the ribosomal DNA. gDNA was isolated and quantified by the same method used for the original root samples. The 3' region of the 18S (SSU), ITS1 and ITS2, the 5.8S ribosomal subunit and the 25-28S (LSU) of Serendipitaceae were amplified by direct PCR using the primers NSSeb1 (SEQ ID NO: 5) and NLSeb1.5R (SEQ ID NO: 6). Each 25 µl PCR reaction included 12.5 µl GO TAQ GREEN MASTER MIX®, 1.25 µl of each primer (0.5 µM) and 10 ng of total genomic DNA. A ~2.2 kb fragment was obtained from the direct PCR reaction. This fragment was diluted 1:200 and used as a template for a first nested PCR (nPCR-I) using the primers ITS3Seb (SEQ ID NO: 7) and NL4 (SEQ ID NO: 8) and a second nested PCR (nPCR-II) using S. vermifera (MAFF305830) specific primers ITS3Seb-MS (SEQ ID NO: 10) and ITS3Seb-R (SEQ ID NO: 9) covering the 3' region of the 5.8S, the highly variable ITS2 region and the 5' region of the 25-28S (LSU) of Serendipitaceae rDNA.

Thermocycling for direct PCR was performed using initial heating at 95° C. for 3 minutes, followed by 35 cycles of denaturation at 95° C. for 30 seconds, annealing at 59° C. for 30 seconds and extension at 72° C. for 2 minutes. The final extension was performed at 72° C. for 10 minutes. For nPCR-I, thermocycling consisted of initial heating at 95° C. for 3 minutes, followed by 20 cycles of denaturation at 95° C. for 30 seconds, annealing at 60° C. for 30 seconds and extension at 72° C. for 1 minute. The final extension was performed at 72° C. for 10 minutes. For nPCR-II, thermocycling consisted of initial heating at 95° C. for 3 minutes, followed by 20 cycles of denaturation at 95° C. for 30 seconds, annealing at 62° C. for 30 seconds and extension at 72° C. for 30 seconds. The final extension was performed at 72° C. for 10 minutes. For all PCR reactions, negative controls containing all reagents except the DNA template and positive control containing S. vermifera (MAFF305830) gDNA were used. PCR products were direct sequenced and blasted against the GenBank database for Serendipita vermifera. nPCR-I yielded a ~1 kb fragment which indicated Serendipita colonization and nPCR-II did not yield any further bands which confirmed that the strains were distinct from S. vermifera (MAFF305830).

Figure 3:
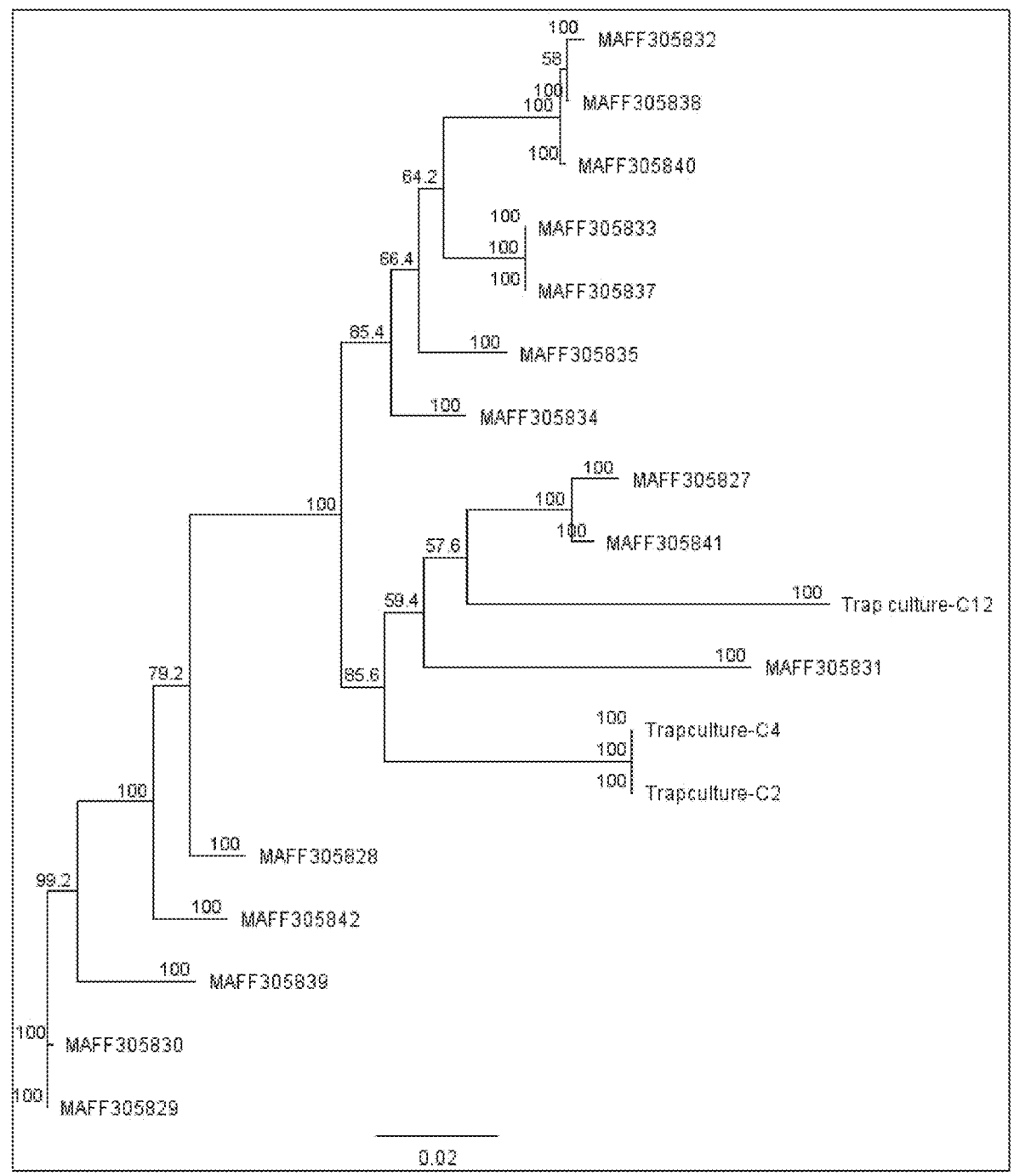
FIG. 3 depicts the phylogenetic relationship between three Serendipitoid sequences detected in switchgrass roots from trap culture with serendipitoid sequences from GenBank and reference strains of *S. vermifera* isolated from Australian orchid reconstructed by the UPGMA method for 20 partial 18S/5.8S/partial LSU rDNA sequences (alignment length 750 bp). Numbers are UPGMA bootstrap values based on 500 replicates. The bar indicates substitutions per site.

The results demonstrated that the sequences are derived from Serendipita vermifera. The sequences were curated for chimeric sequences and multiple sequence alignment and phylogenetic distance was estimated with reference strains of Serendipita vermifera (Australian orchid). The phylogenetic affinities of the three sequences, designated Trapculture-C2 (from the sample yielding NFSgF_C2), Trapculture-C4 (from the sample yielding NFSgF_C4) and Trap culture-C12 (from the sample yielding NFSgF_C12), with known serendipitoid sequences from GenBank and reference strains from S. vermifera isolated from Australian orchid were determined by the UPGMA method as shown in FIG. 3.

Root samples were collected from trap culture from the sample yielding Trapculture-C2 and cleaned by washing with running water. The samples were surface sterilized with 70% ethanol for 5 minutes followed by 2% sodium hypochlorite for 1 minute and washing with sterile water. Samples were then plated onto Modified Melin Norkan's agar, pH 8 (MMN agar plates) amended with Ampicillin (1000 mg $L^{-1}$), Chloramphenicol (50 mg $L^{-1}$) and Streptomycin (50 mg $L^{-1}$), Benomyl (4 mg $L^{-1}$) and Dichloran (8 mg $L^{-1}$). Plates were incubated in the dark at 24° C. and examined regularly for emerging fungal colonies. Emerging fungal colonies were passed through several rounds of subculture until pure axenic cultures were obtained which were then maintained on MMN agar plates for DNA extraction. A single axenic culture was obtained from Trapculture-C2 which was used for further analysis.

Figure 5:
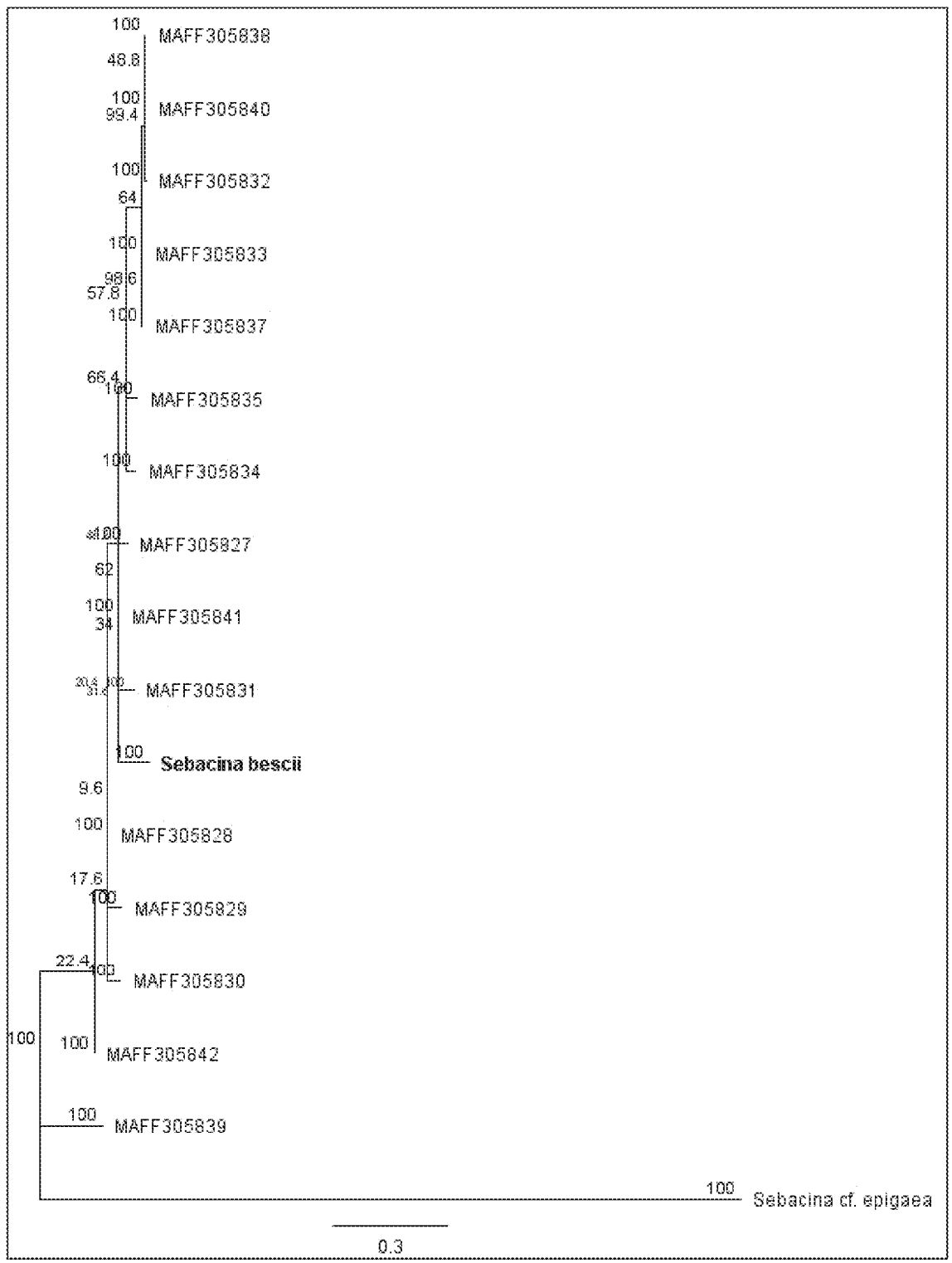
FIG. 5 depicts the phylogenetic relationship between reference strains of *S. vermifera* isolated from Australian Orchid with the new strain of *Serendipita* (*S. bescii*) isolated from switchgrass reconstructed by the UPGMA method for 17 partial 18S/5.8S/partial LSU rDNA sequences (alignment length 630 bp). Numbers are UPGMA bootstrap values based on 500 replicates. The bar indicates substitutions per site.
Figure 6:
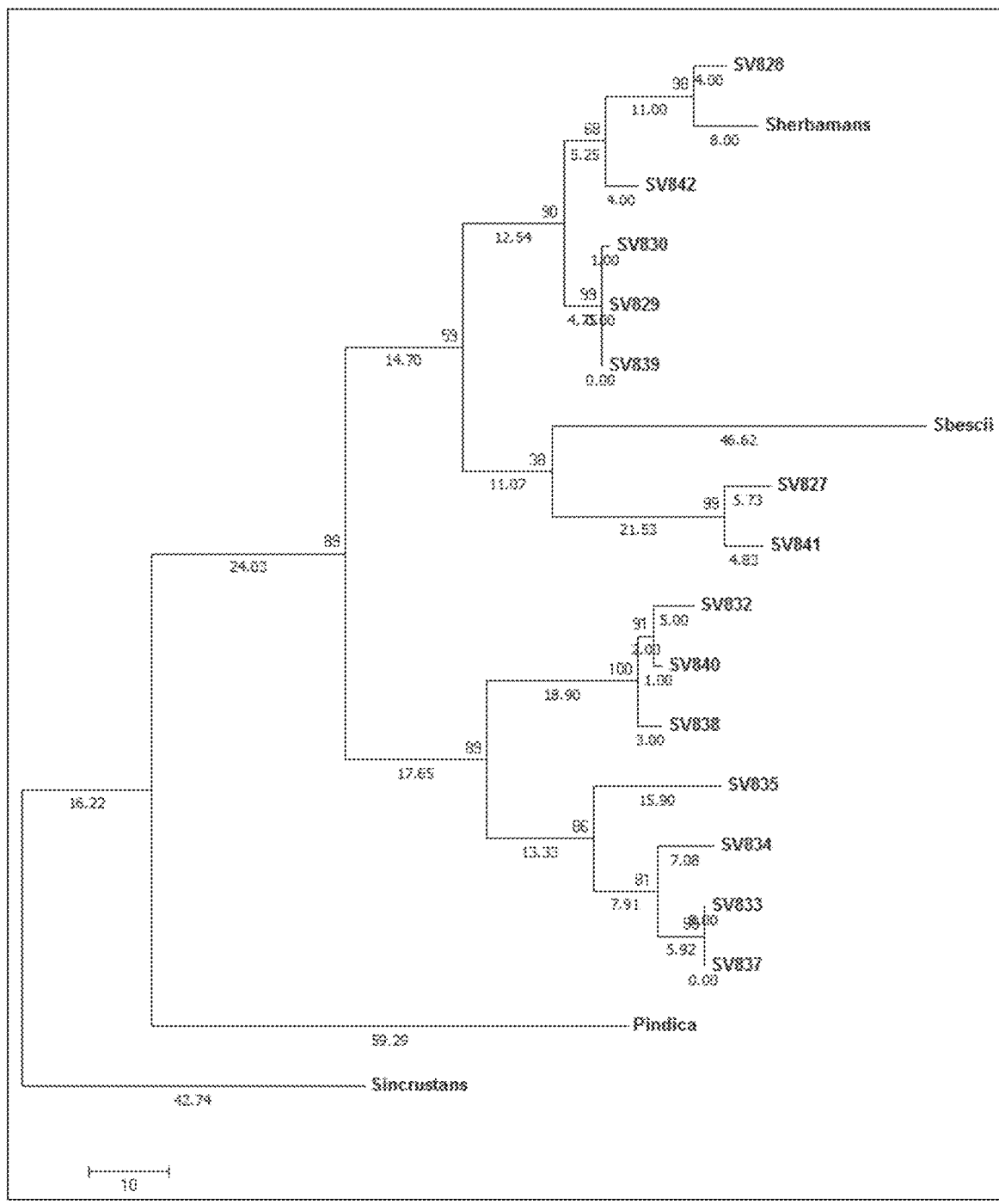
FIG. 6 depicts the phylogenetic relationship of *S. bescii* to *S. vermifera* strains using the Maximum Parsimony method. Tree #1 out of 3 most parsimonious trees (length=395) is shown. The percentage of replicate trees in which the associated taxa clustered together in the bootstrap test (500 replicates) are shown next to the branches. The MP tree was obtained using the Subtree-Pruning-Regrafting (SPR) algorithm. Branch lengths were calculated using the average pathway method and re in the units of the number of changes over the whole sequence. They are shown next to the branches. The tree is drawn to scale. All positions containing gaps and missing data were eliminated. There were a total of 499 positions in the final dataset. Evolutionary analyses were conducted in MEGA6.

DNA extraction and quantification was performed as described previously. Nested PCR based screening was performed using the same method as applied for the assessment of trap culture for Serendipita colonization using NSSeb1 (SEQ ID NO: 5) and NLSeb1.5R (SEQ ID NO: 6) primers for direct PCR, ITS3Seb (SEQ ID NO: 7) and NL4 (SEQ ID NO: 8) primers for one nested PCR (nPCR-I) and S. vermifera (MAFF305830) specific ITS3Seb-MS (SEQ ID NO: 10) and ITS3Seb-R (SEQ ID NO: 9) primers for other nested PCR (nPCR-II). The PCR products were submitted for sequencing with the same set of primers at Noble Foundation's genomics Core Facility. DNA sequences were manually inspected, edited using geneious version 6.1.2 (Biomatters Auckland, New Zealand). The sequences were then subjected to BLASTn searches against the NCBI nonredundant database (GenBank) for sequence identities with known *Serendipita* sequences. The axenic culture obtained was identified as a new strain, designated *Serendipita vermifera* ssp. *bescii* ("*S. bescii*"). In addition, a trap culture was set up in a rhizobox with two switchgrass plants having a *Serendipita* sequence of Trapculture-2 on either side of an orchid plant with membranes between the three plants. Invasion of the switchgrass roots into the orchid portion of the rhizobox was observed and samples of these roots were collected and DNA analysis performed as above. The sequence alignment of the D1/D2 rDNA sequences of the serendipitoid sequences detected in switchgrass roots from the field, trap culture and from the switchgrass roots in the rhizobox are compared with that from the *Serendipita* axenic culture, designated *Serendipita bescii*, are shown in FIG. 4. Phylogenetic maps relating the new strain to known *S. vermifera* strains are shown in FIGS. 5-6.

Figure 7A:
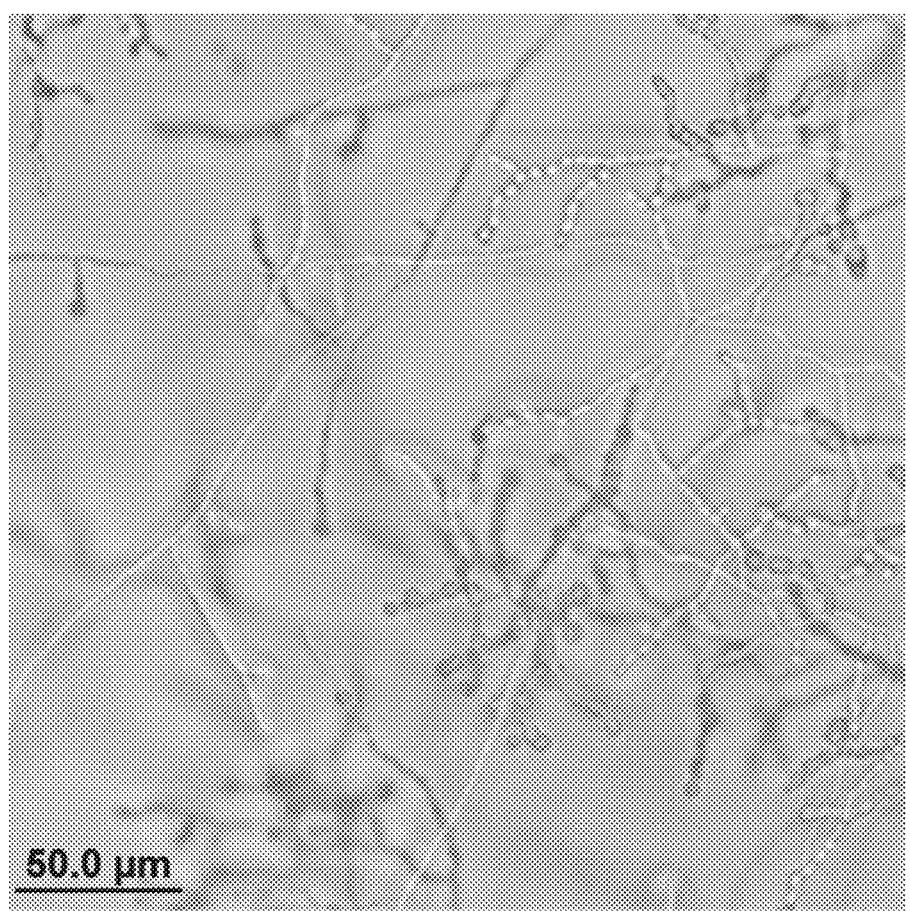
FIG. 7A shows a micrograph of the axenic culture of *S. bescii* using a light microscope. Scale bar=50.0 μm.
Figure 7B:
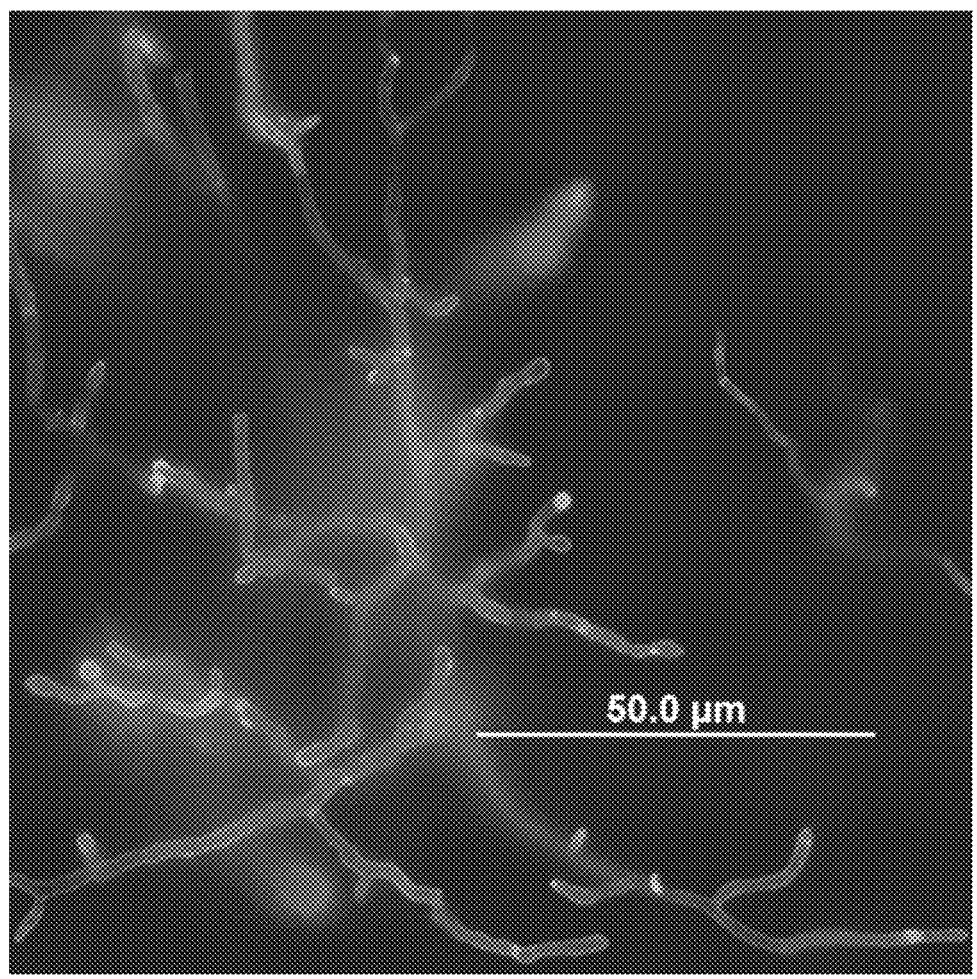
FIG. 7B shows a fluorescent micrograph of the axenic culture of *S. bescii*. Scale bar=50.0 μm.
Figure 7C:
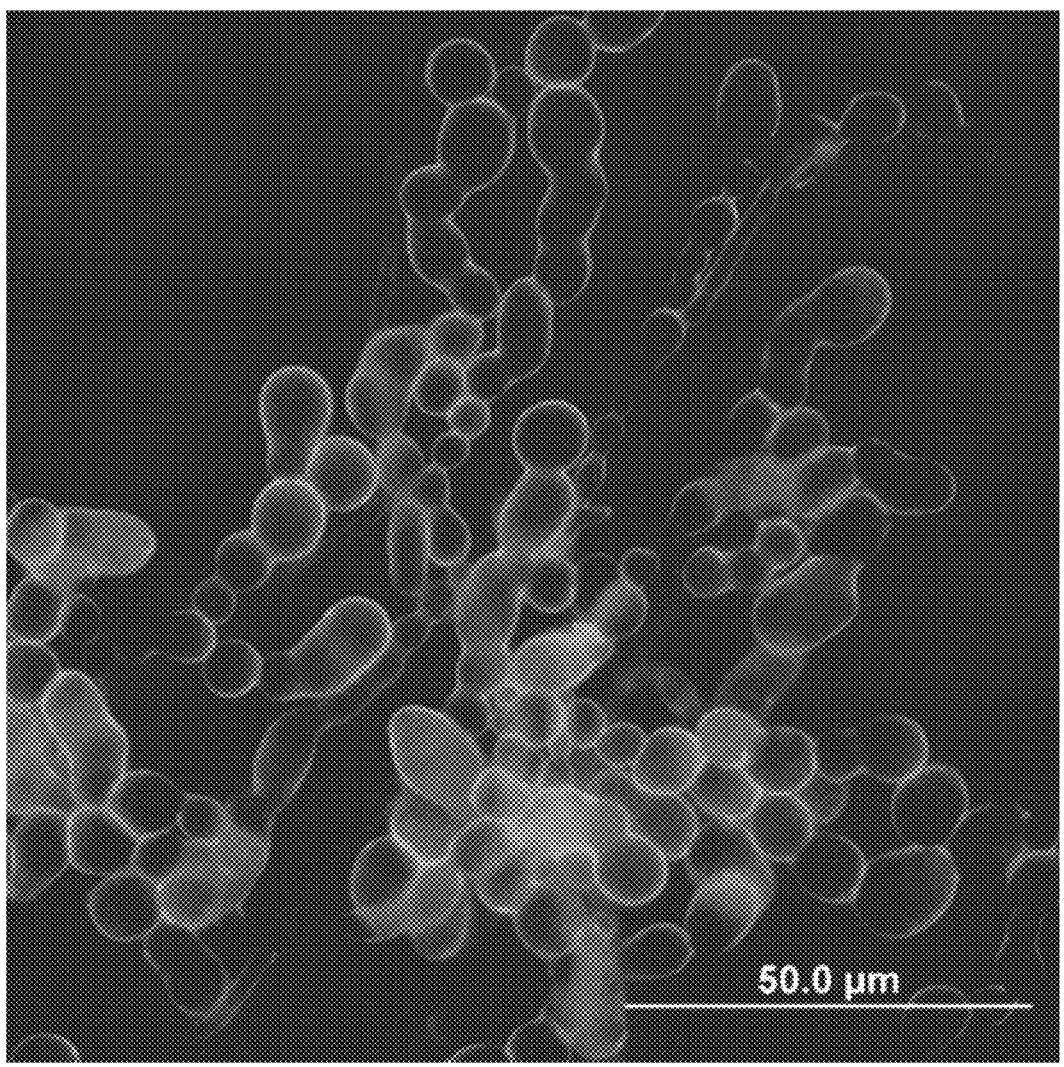
FIG. 7C shows a fluorescent micrograph of the axenic culture of *S. bescii*. Scale bar=50.0 μm.
Figure 7D:
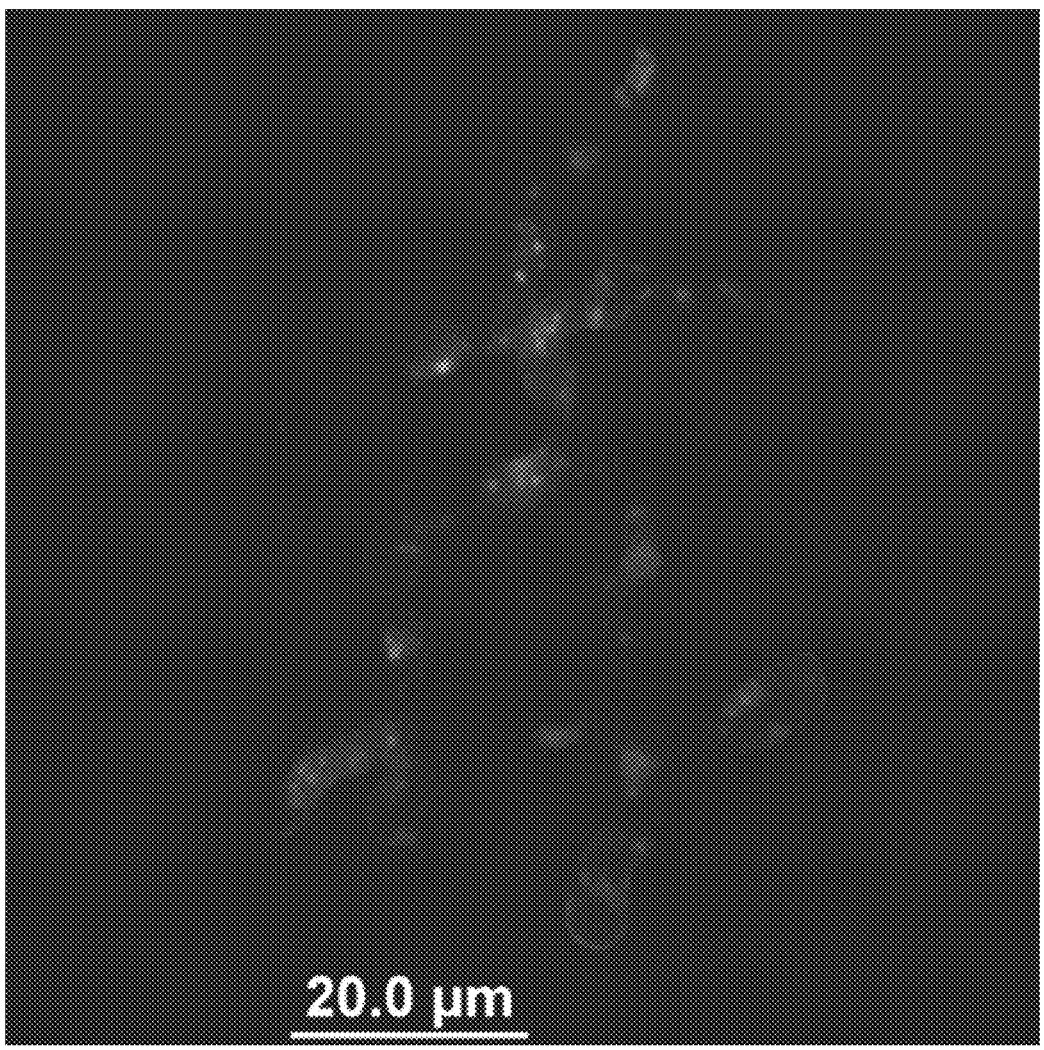
FIG. 7D shows a fluorescent micrograph of the axenic culture of *S. bescii* after DAPI staining. Scale bar=20.0 μm.

The axenic culture of the new isolate was viewed under a light microscope and imaged as shown in FIG. 7A. The axenic culture of the new isolate and an axenic culture of *S. vermifera* (MAFF305830), obtained by the trap culture methods discussed above, were also stained in a 10 µg/ml solution of WGA-AF® 488 (Life Technologies, Carlsbad, Calif., United States) in 1×PBS and visualized under an Olympus fluorescent compound microscope (Nikon, United States) as shown in FIGS. 7B-7D (*S. bescii* only) which show normal hyphae, monilioid hyphae and DAPI staining, respectively. FIGS. 8A-8B show light and fluorescent micrographs for comparison of the axenic cultures of *S. bescii* and *S. vermifera* (MAFF305830) stained using WGA-AF® 488. Similar staining and imaging was performed on switchgrass roots colonized with *S. bescii* or *S. vermifera* (MAFF305830) as shown in FIG. 8C.

Figure 9:
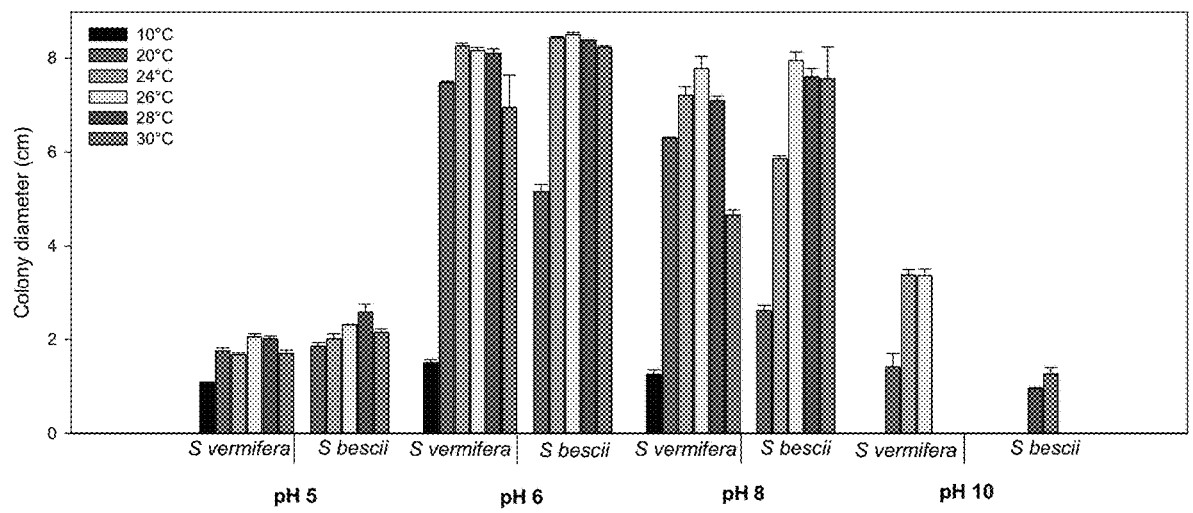
FIG. 9 depicts the colony diameter (cm) 14 days post-inoculation for axenic cultures of *S. vermifera* (MAFF305830) and *S. bescii* at various temperature and pH conditions on MMN agar. Each data point is the mean of three replicates with standard error of mean.

Growth, as measured by colony diameter 14 days after inoculation, of the *S. vermifera* (MAFF305830) and *S. bescii* isolates on MMN agar with varying temperature and pH was also assessed as shown in FIG. 9.

The axenic culture of the new isolate, designated *S. bescii*, is currently stored at the Noble Research Institute, LLC, 2510 Sam Noble Parkway, Ardmore, Okla., United States.

Example 2: Growth Promotion Studies Under Normal Watering Conditions

Figure 10:
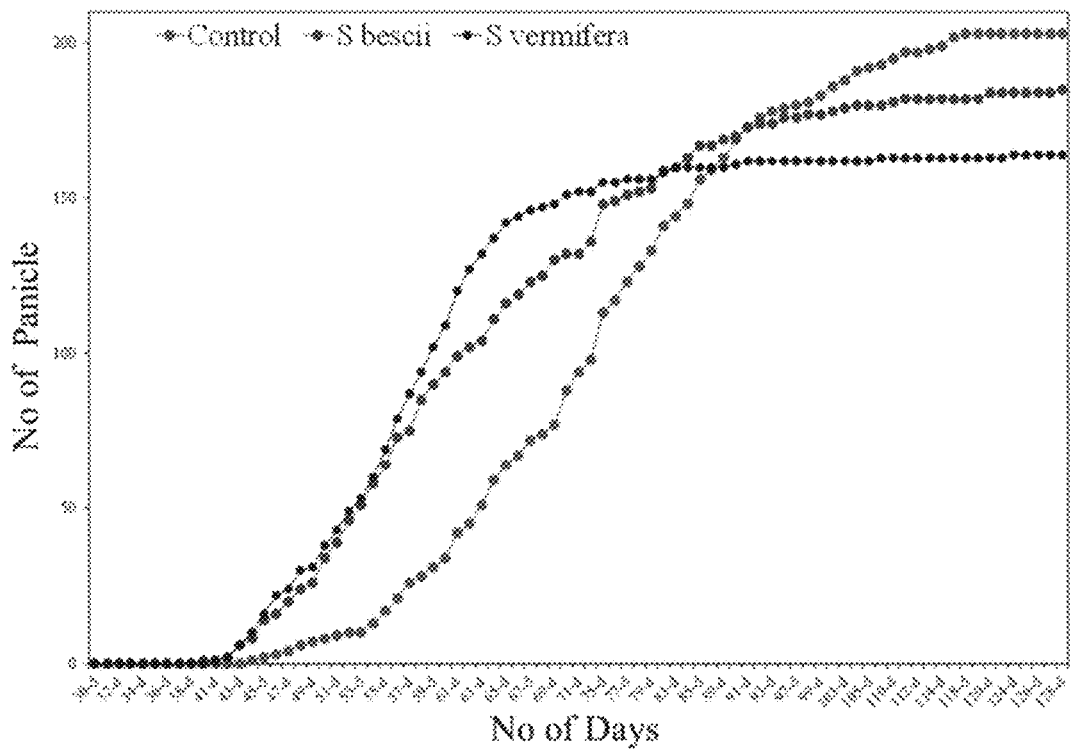
FIG. 10 depicts the grain yield in winter wheat inoculated with *S. bescii*, *S. vermifera* (MAFF305830) or un-inoculated over time. Each data point indicates the total number of panicles produced over time in eight replicate plants for each treatment.

A greenhouse trial was conducted to see the effect of *S. bescii* on grain yield of winter wheat (OK08328). Plants were colonized in vitro with *S. vermifera* (MAFF305830) and *S. bescii*, respectively. After two weeks, seedlings were vernalized for an additional six weeks before transplanting in Metromix and moving into a greenhouse. An un-inoculated set was maintained under the same conditions throughout for direct comparison. The experimental design consisted of a complete randomized block design with eight replicates per treatment. At maturity, plants were harvested and grain yield data was recorded as shown in Table 1 below and FIG. 10.

TABLE 1

Grain yield data for winter wheat treated with *S. vermifera* (MAFF305830) and *S. bescii*

|  | No. of Panicles | No. of Seeds | Seed weight (g) |
|---|---|---|---|
| Control | 25.38 +/− 0.91 a | 984.37 +/− 37.07 a | 33.90 +/− 1.31 a |
| *S. bescii* | 23.13 +/− 1.42 ab | 1026.00 +/− 37.21 a | 35.30 +/− 0.86 a |
| *S. vermifera* (MAFF305830) | 20.5 +/− 0.78 b | 960.75 +/− 30.57 a | 35.49 +/− 0.97 a |
| Statistical Significance | * | not significant | not significant |

(Different letters indicate a significant difference between treatments at $p \le 0.05$; * = statistically significant)

Example 3: Growth Promotion Studies Under Normal and Restricted Watering Conditions in Winter Wheat

Figure 11A:
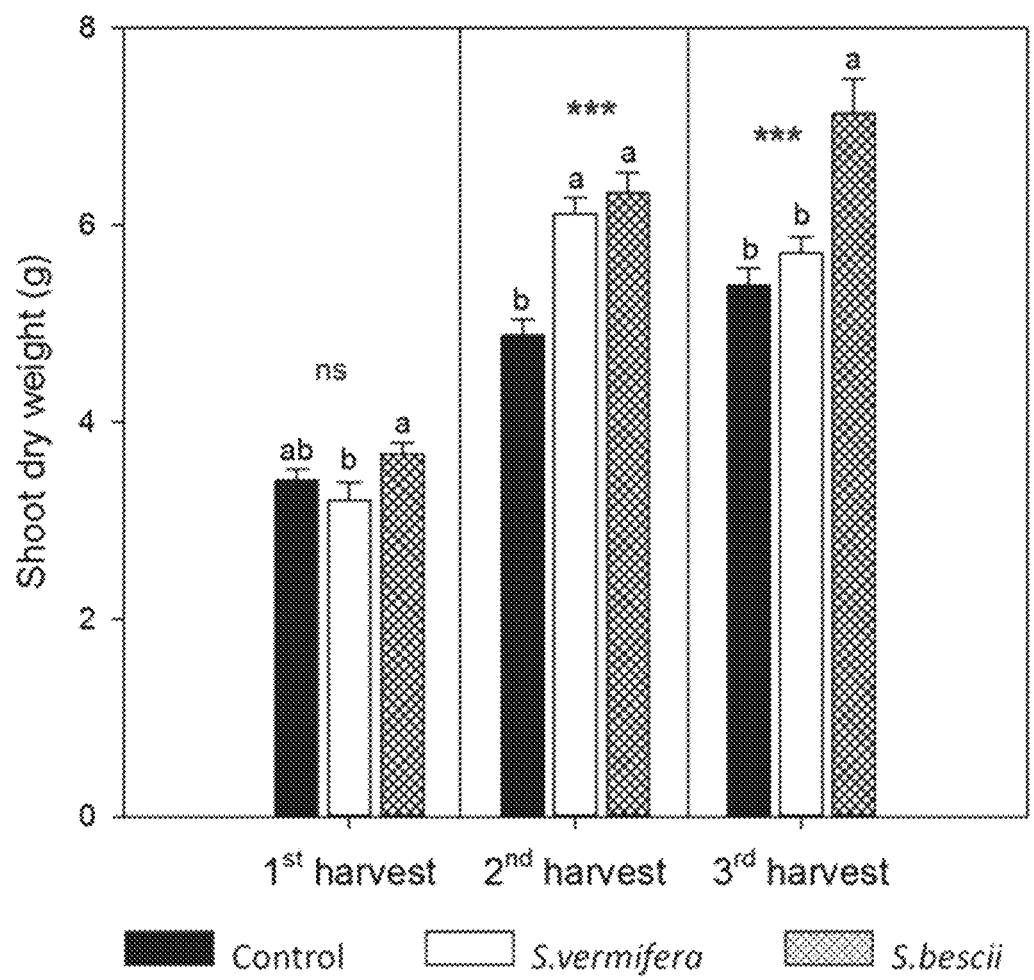
FIG. 11A depicts the forage dry weight under normal watering conditions for winter wheat inoculated with *S. bescii*, *S. vermifera* (MAFF305830) or un-inoculated over three harvests. Bars with different letters indicate a significant different between treatment at p≤0.05.
Figure 11B:
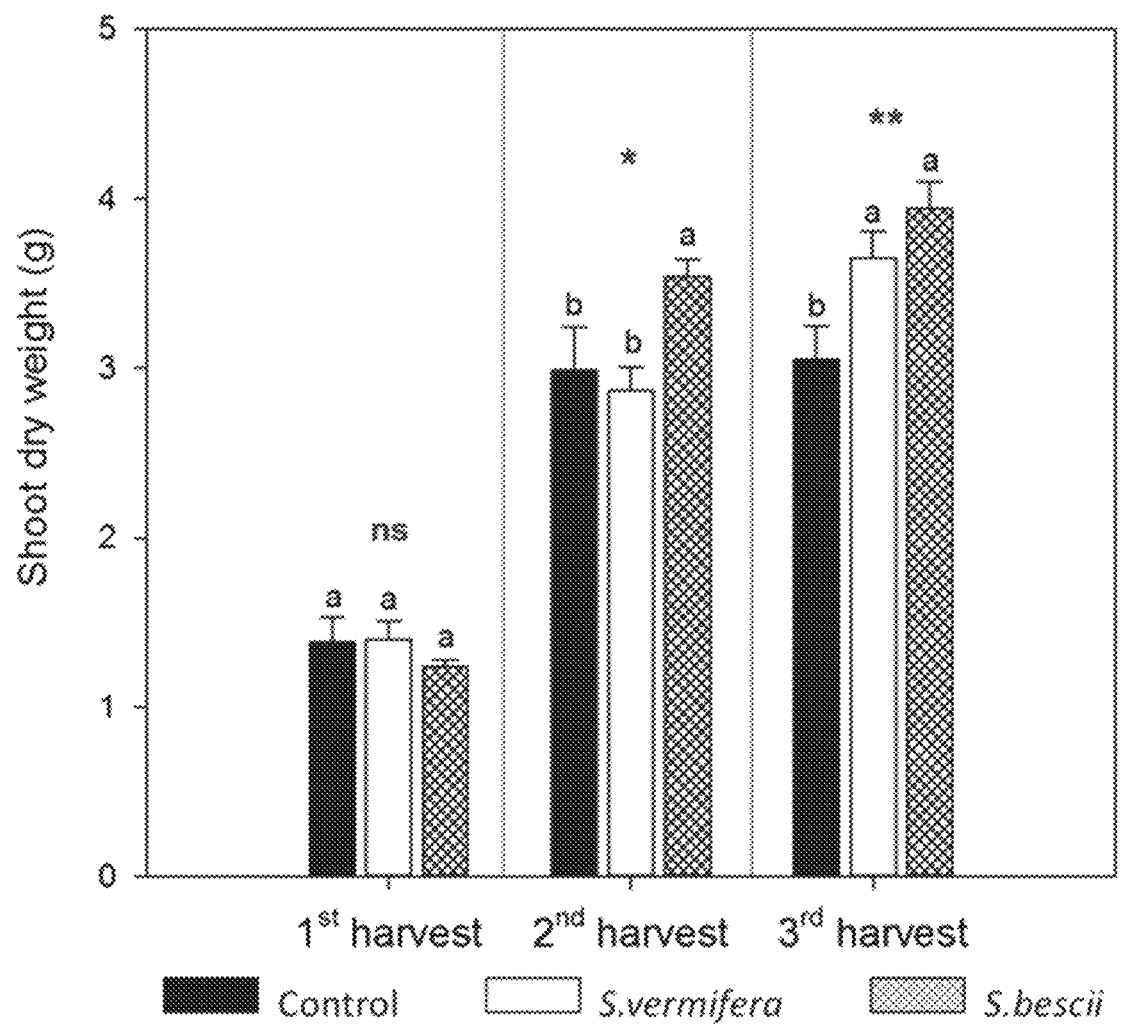
FIG. 11B depicts the forage dry weight under drought conditions for winter wheat inoculated with *S. bescii*, *S. vermifera* (MAFF305830) or un-inoculated over three harvests. Bars with different letters indicate a significant difference between treatment at p≤0.05.

*Triticum aestivum* (winter wheat—NF 101) was colonized in vitro with *S. vermifera* and *S. bescii* respectively. After 14 days post-inoculation, plants were transplanted in Metromix and maintained in a controlled greenhouse environment. Water restriction was set in effect two weeks after transplantation. The experimental design consisted of three treatments (*S. bescii*, *S. vermifera* and a control (un-inoculated) group) each within normal watering and restricted watering with ten replicates per treatment. Plants were arranged in a randomized complete block design. The data were analyzed using analysis of variance (ANOVA) method. Plants were harvested for forage biomass three times (i.e., once every four weeks). Subsequently, the dried forage were processed for forage quality analysis. An un-inoculated set was maintained under the same conditions throughout for direct comparison. The results of the study are shown in FIGS. 11A-11B which show the shoot dry weight for each treatment at the first, second and third harvests under normal watering (FIG. 11A) and drought (FIG. 11B) conditions.

Example 4: Growth Promotion Studies Under Normal and Restricted Watering Conditions in Alfalfa

Figure 12A:
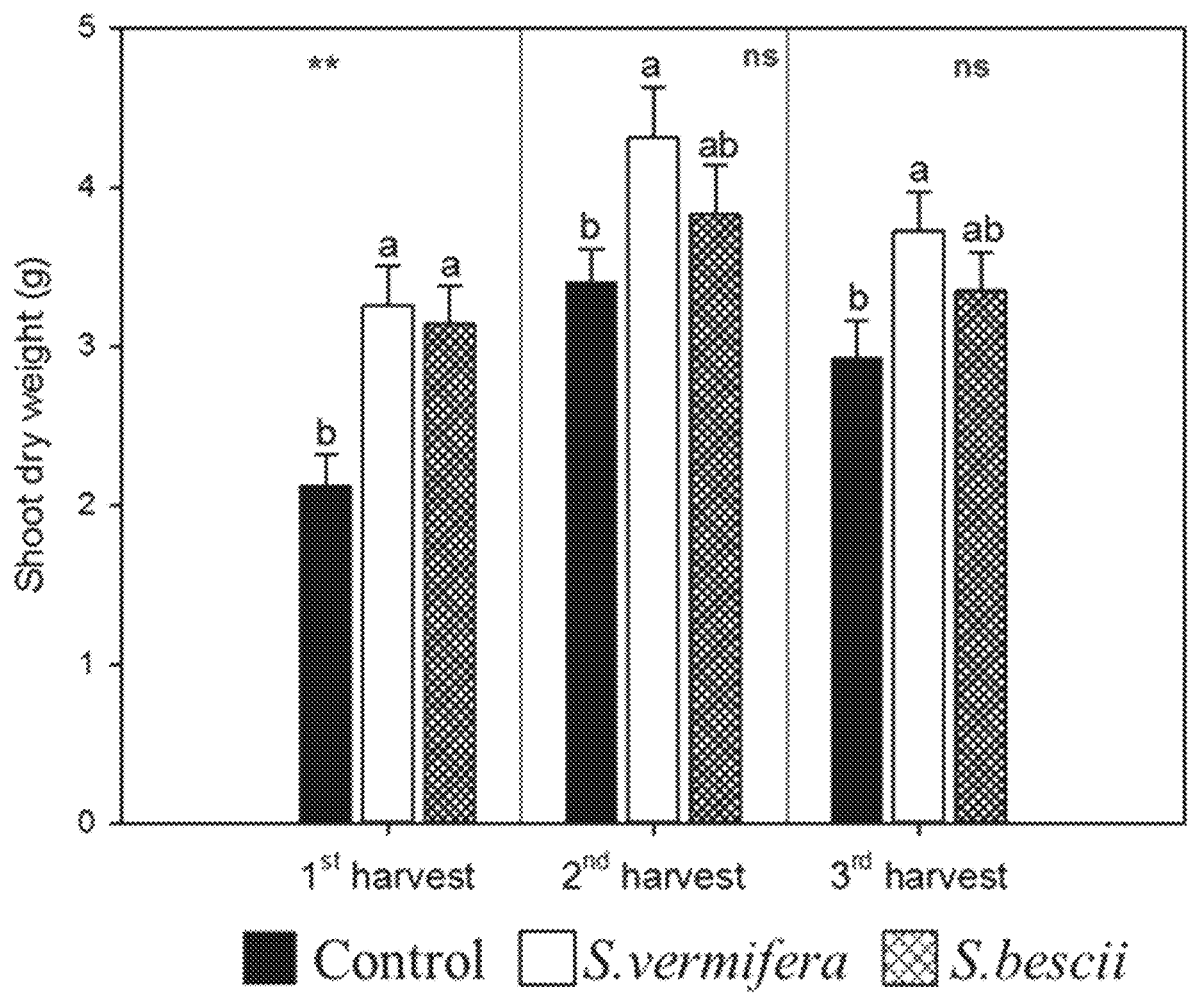
FIG. 12A depicts the forage dry weight under normal watering conditions for alfalfa inoculated with *S. bescii*, *S. vermifera* (MAFF305830) or un-inoculated over three harvests. Bars with different letters indicate a significant different between treatment at p≤0.05.
Figure 12B:
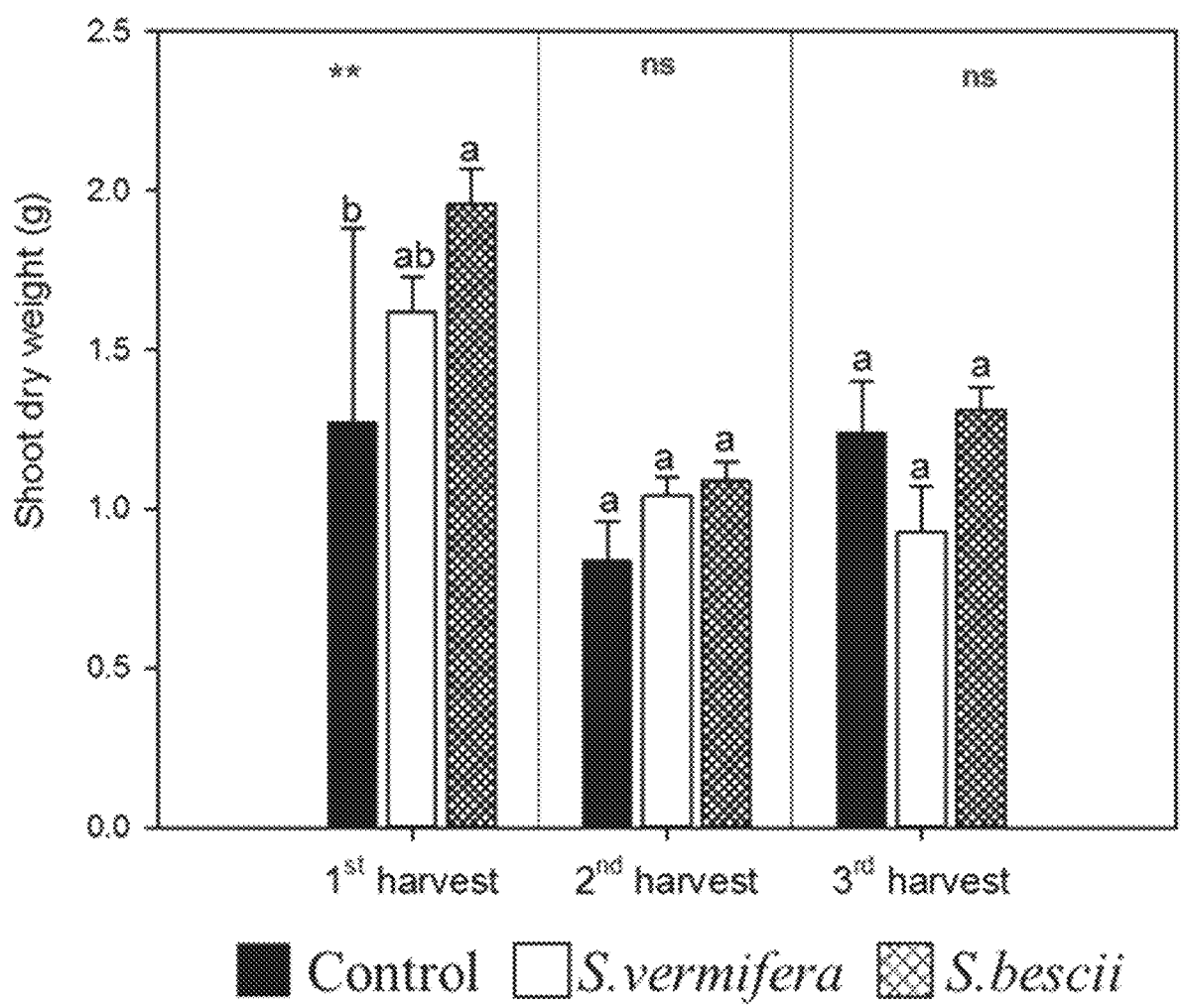
FIG. 12B depicts the forage dry weight under drought conditions for alfalfa inoculated with *S. bescii*, *S. vermifera* (MAFF305830) or un-inoculated over three harvests. Bars with different letters indicate a significant different between treatment at p≤0.05.

*Medicago sativa* (NECS-141) cuttings were colonized in vitro with *S. vermifera* and *S. bescii* respectively. After 14 days post-inoculation, plants were transplanted in Metromix and maintained in a controlled greenhouse environment. Water restriction was set in effect two weeks after transplantation. The experimental design consisted of three treatments (*S. bescii*, *S. vermifera* and a control (un-inoculated) group) each within normal watering and restricted watering with ten replicates per treatment. Plants were arranged in a randomized complete block design. The data were analyzed using analysis of variance (ANOVA) method. Plants were harvested three weeks after initiation of water limitation and estimated for forage biomass. Subsequently, the dried forage were processed for forage quality analysis. Samples for the second and third harvests were collected at 60 days and 90 days post-inoculation. An un-inoculated set was maintained under the same conditions throughout for direct comparison. The results of the study are shown in FIGS. 12A-12B which show the shoot dry weight for each treatment at the first, second and third harvests under normal watering (FIG. 12A) and drought (FIG. 12B) conditions.

Example 5: Colonization of Blueberry Plants by *S. bescii*

Blueberries are perennial flowering plants within the genus *Vaccinium* which also includes cranberries, bilberries and grouseberries. Colonization of blueberry roots is generally difficult and positive outcomes are not typical because blueberries, as members of the heath family, Ericaceae, must have symbiotic fungi to live properly, being so adapted to have mycorrhizae as to not have root hairs. Generally, plants of the family Ericaceae, and specifically blueberries, have a type of mycorrhizial association called ericoid mycorrhizae.

Blueberry seedlings were colonized using a bentonite clay-based inoculation method as described in Example 8 below. Plants were maintained in the greenhouse. Roots were collected one month post-colonization. Root samples were analyzed by fluorescent microscopy after staining with WGA-AF® 488 and by PCR using S. bescii specific primers (SEQ ID NOs: 11 and 12) and subsequent sequencing.

Figure 13A:
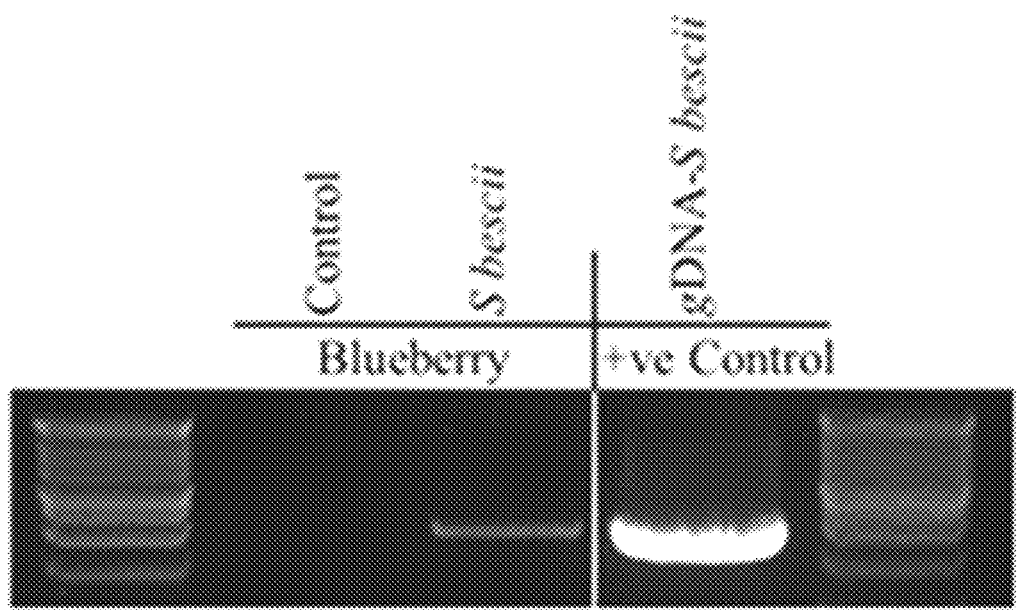
FIG. 13A shows an agarose gel electrophoresis of the PCR product of a blueberry root extract after inoculation with *S. bescii* and a positive control sample of *S. bescii*.
Figure 13B:
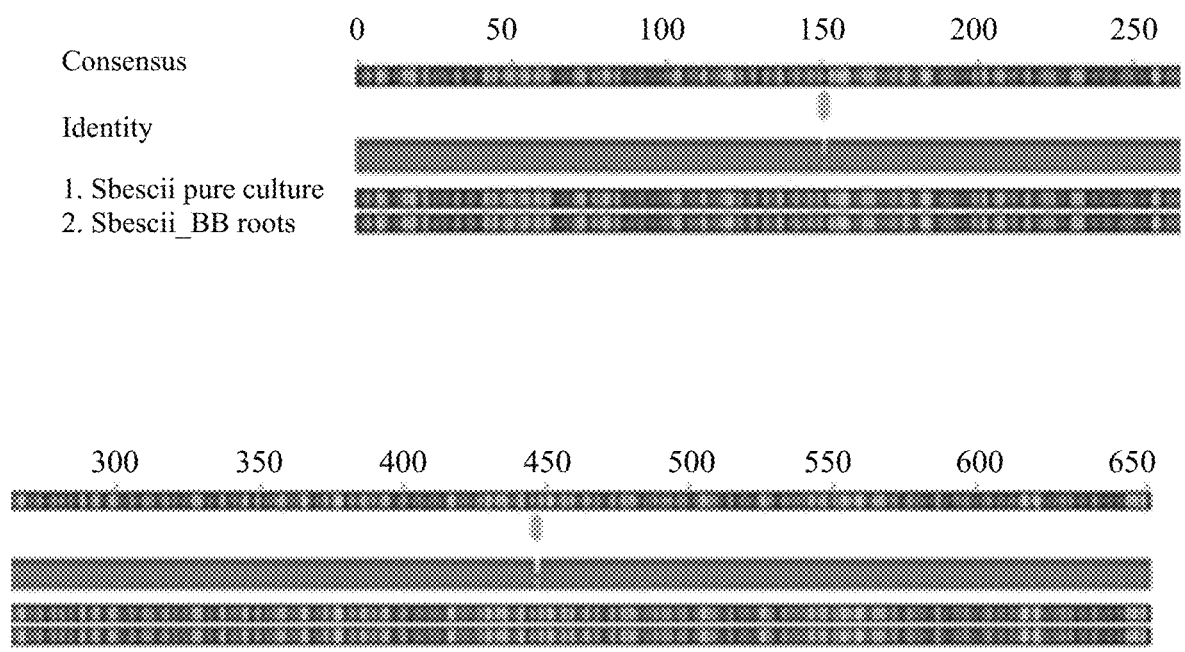
FIG. 13B shows the alignment of PCR sequencing results for a blueberry plant after inoculation with *S. bescii* compared with a pure culture of *S. bescii*.

As shown in FIG. 13A, blueberry roots were effectively colonized by S. bescii using a bentonite clay-based inoculation method in sterile Metromix. FIG. 13B shows confirmation of the colonization by sequencing.

Example 6: Effect of S. bescii Colonization on Switchgrass Height

Figure 14:
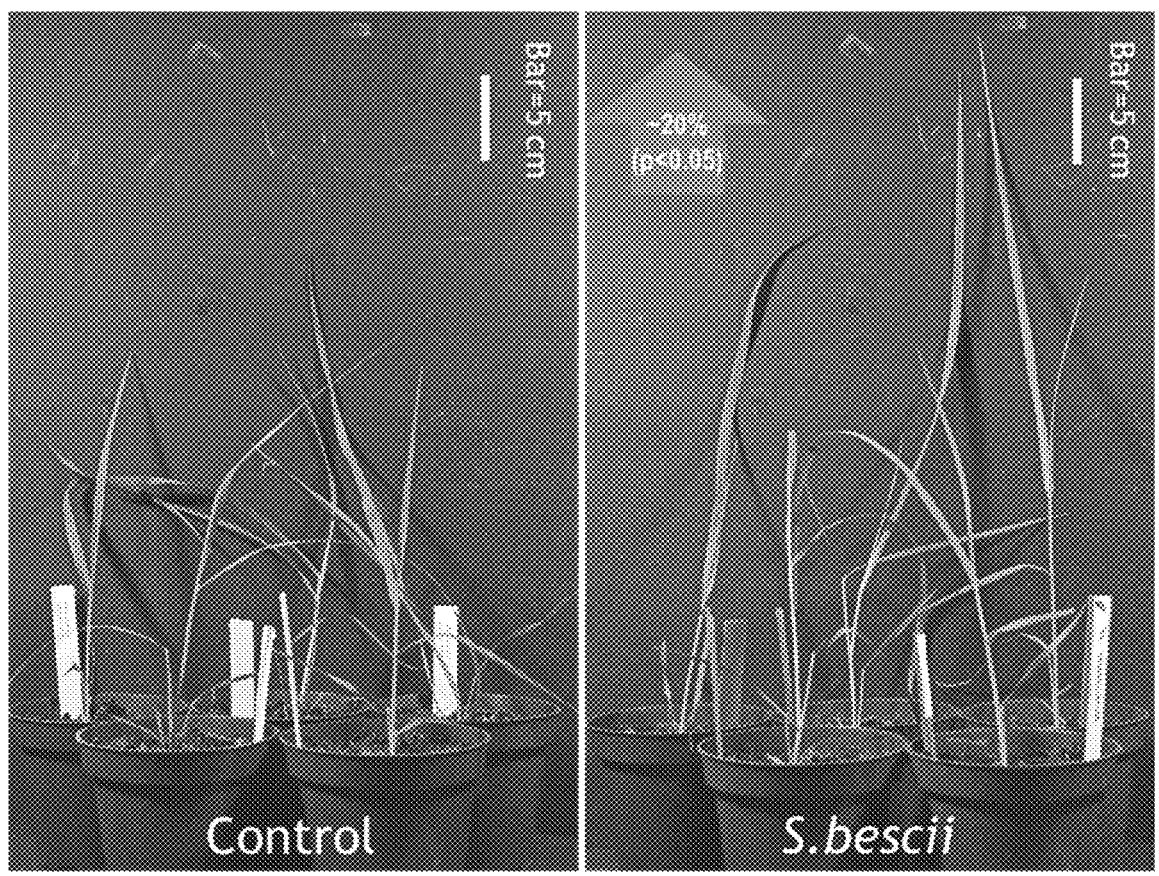
FIG. 14 depicts five replicate plants of a control group of switchgrass plants grown for 4 weeks in a greenhouse and five replicate plants colonized with *S. bescii* grown under the same greenhouse conditions. Scale bar=5 cm.
Figure 15A:
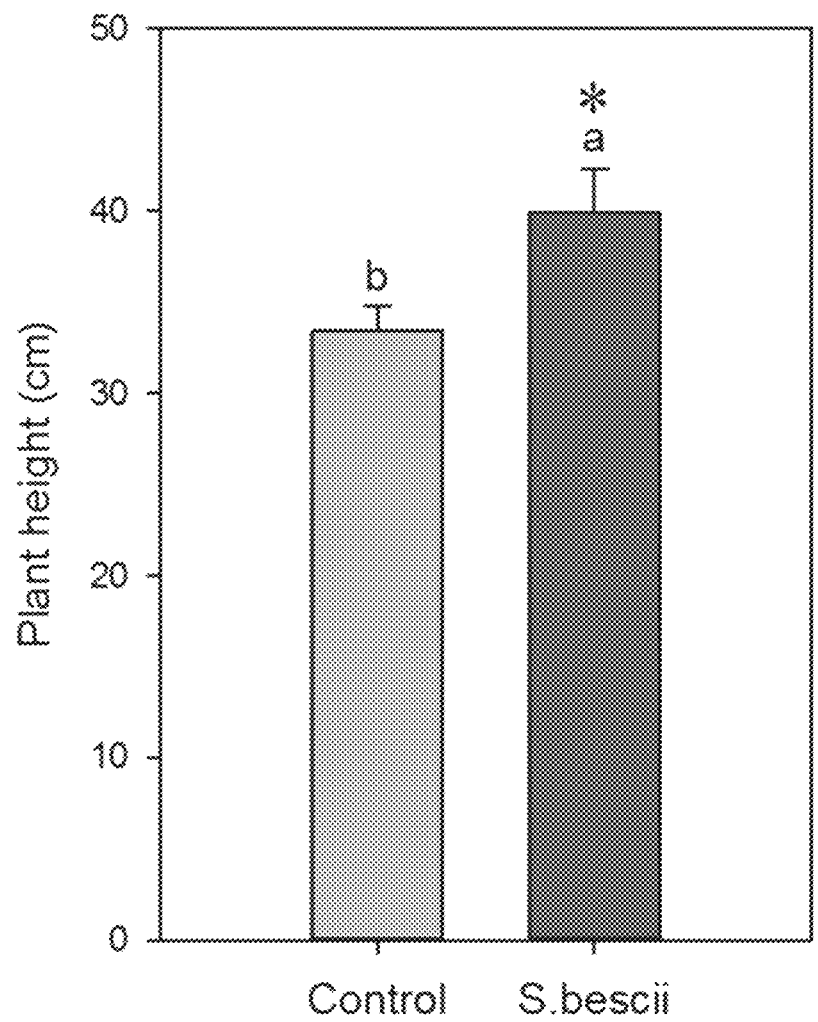
FIG. 15A shows the effect of *S. bescii* colonization on plant height in switchgrass as compared to an un-inoculated control group. Error bar denotes standard error of mean. Significant effects are marked as follows: $0.01 \leq p \leq 0.05$ (*); $0.001 \leq p \leq 0.01$ (); $p \leq 0.001$ (*); and $p > 0.05$ (ns).
Figure 15B:
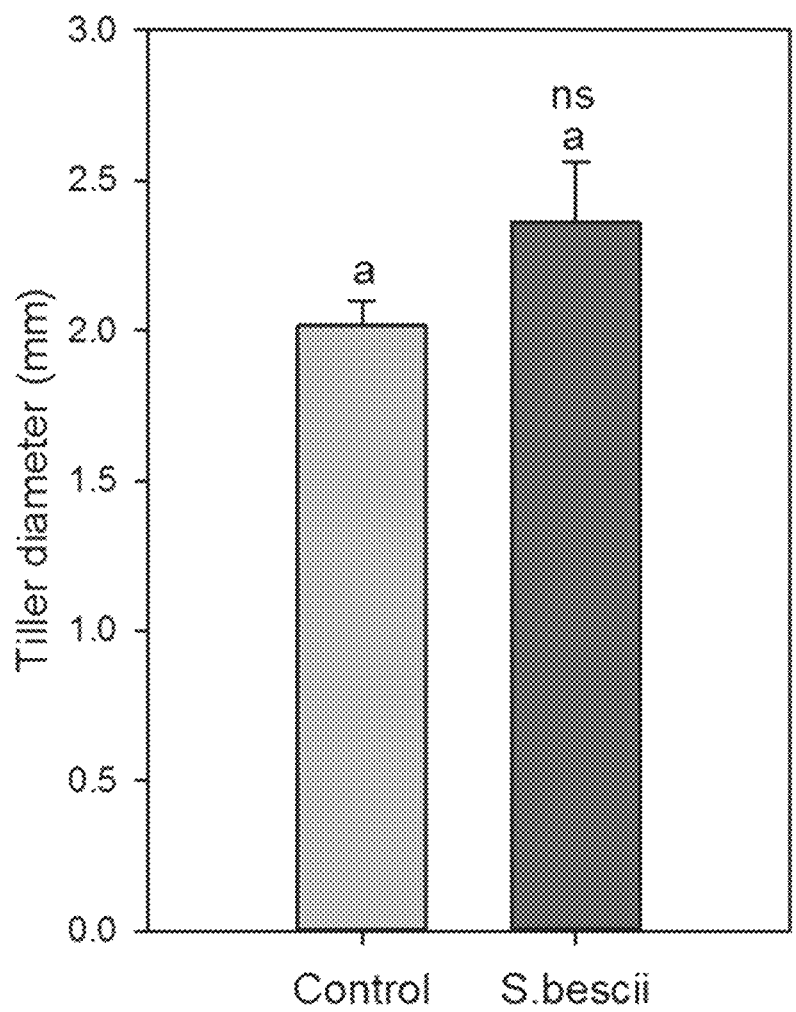
FIG. 15B shows the effect of *S. bescii* colonization on tiller diameter in switchgrass as compared to an un-inoculated control group. Error bar denotes standard error of mean. Significant effects are marked as follows: $0.01 \leq p \leq 0.05$ (*); $0.001 \leq p \leq 0.01$ (); $p \leq 0.001$ (*); and $p > 0.05$ (ns).

Switchgrass (Panicum virgatum L) seedlings were colonized in vitro in minimal (M) media with S. bescii. Colonization was performed using 175-ml plant containers (5 cm in diameter by 11 cm in height) with lids. The containers were filled with 50 ml of M (minimal) medium pH 5.5 containing 0.3% phytagel amended with 1% sucrose. Clonally propagated switchgrass plants were grown in this medium. For the purpose of in vitro colonization, a seed culture of S. bescii was prepared by grinding the mycelia in liquid M media. Individual plants were inoculated with 20 µl of liquid culture by injecting it into the media with a sterile pipette. To maintain uniformity, the media containing the control plants were injected with the same volume of liquid M media. Plants were maintained in a growth chamber at 26° C. under a 17:9 h photoperiod for 2 weeks. After 2 weeks, seedlings were transplanted in 12 gallon pots containing autoclaved Metromix as potting mix. Plants were maintained in the greenhouse for 4 weeks before collecting tiller height and tiller diameter data. The experiment was conducted in five replicates. Un-inoculated plants were maintained in the same way and were used as a control for data analysis. Photographs of five replicate plants for each treatment were taken and are shown in FIG. 14. Data were analyzed using the ANOVA method. When a significant F-test was observed, treatment means were compared using lest significant differences (LSD) at p<0.05 using Costat statistical software 6.4 (Cohort, Berkeley, Calif., United States). The results were plotted graphically using SigmaPlot 12.5 (Systat Software, San Jose, Calif., United States) as shown in FIGS. 15A-15B. As shown, S. bescii colonization significantly enhances height (~20%; p<0.05) of switchgrass compared to the control.

Figure 16A:
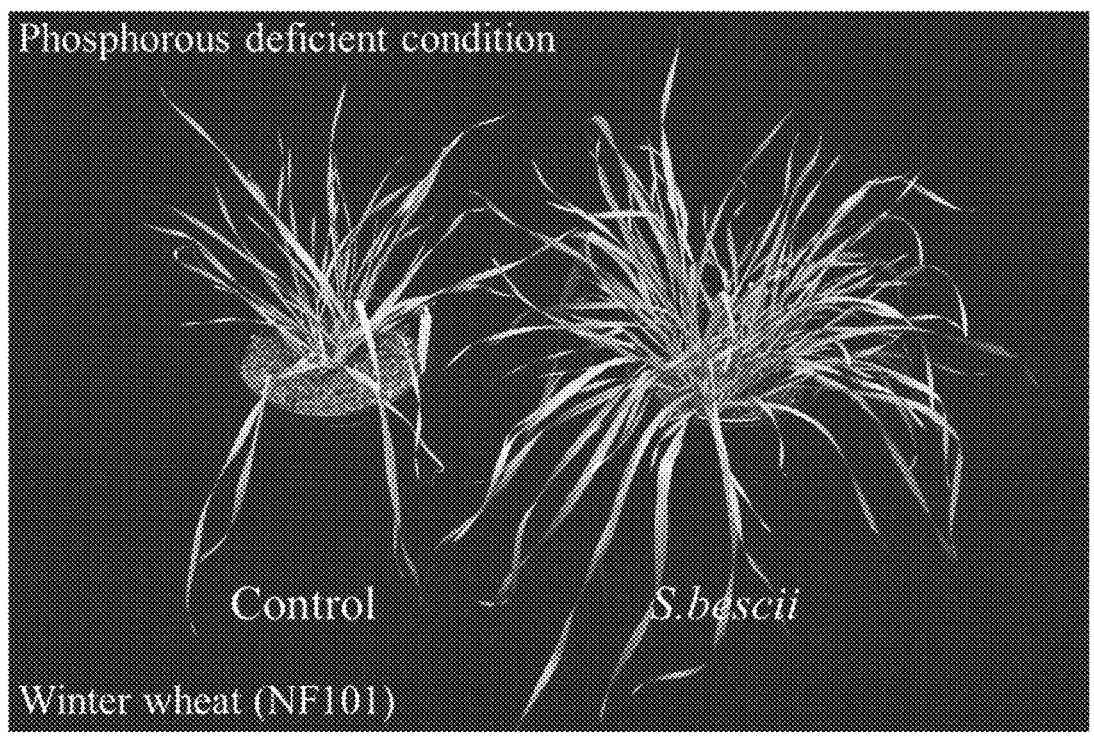
FIG. 16A shows a photograph of representative winter wheat plants grown under phosphorous-deficient conditions with *S. bescii* colonization and without (control).
Figure 16B:
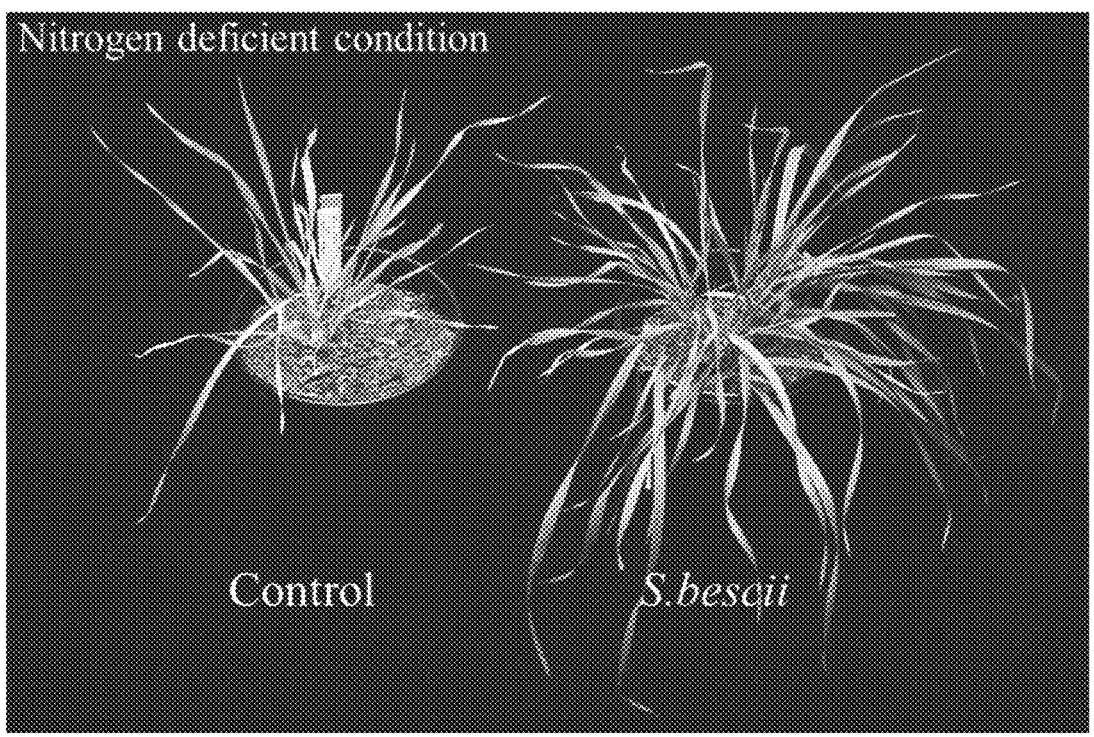
FIG. 16B shows a photograph of representative winter wheat plants grown under nitrogen-deficient conditions with *S. bescii* colonization and without (control).
Figure 17A:
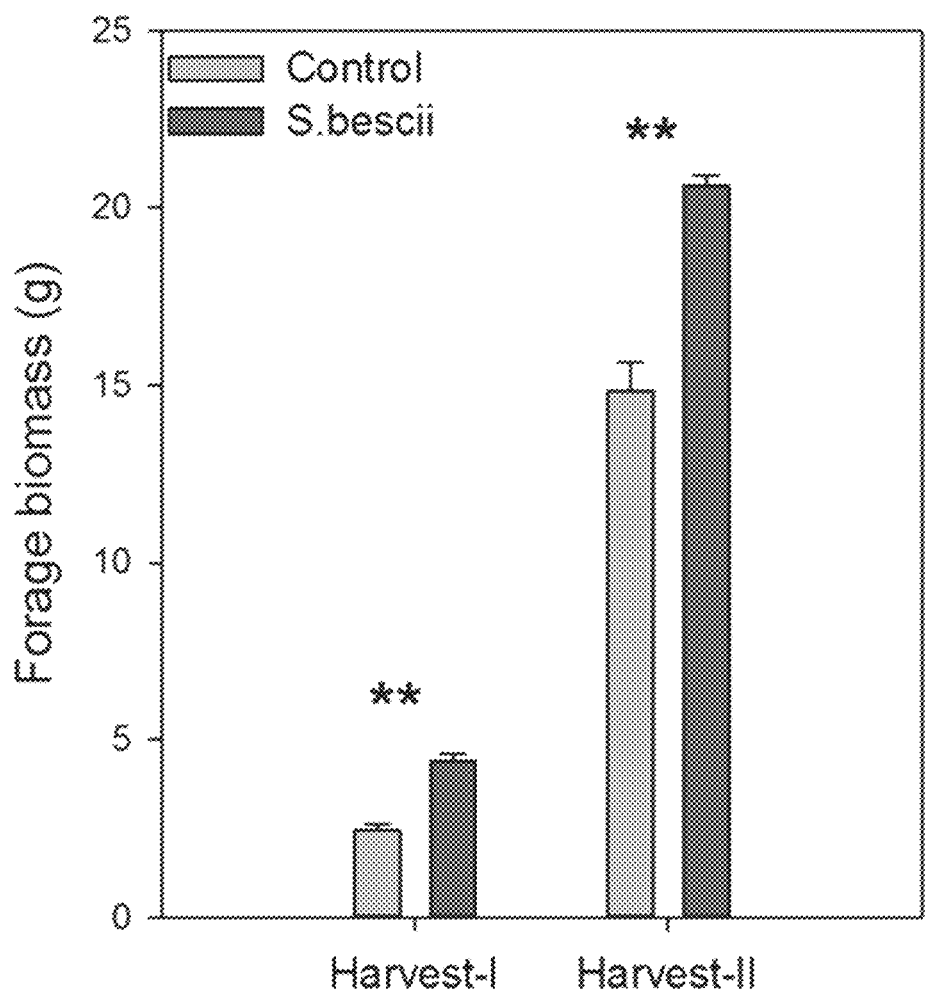
FIG. 17A shows the effect of *S. bescii* colonization on forage biomass in winter wheat under phosphorous-deficient conditions as compared to an un-inoculated control group with harvests at 30 days (Harvest-I) and 60 days (Harvest-II). Error bar denotes standard error of mean. Significant effects are marked as follows: $0.01 \leq p \leq 0.05$ (*); $0.001 \leq p \leq 0.01$ (); $p \leq 0.001$ (*); and $p > 0.05$ (ns).
Figure 17B:
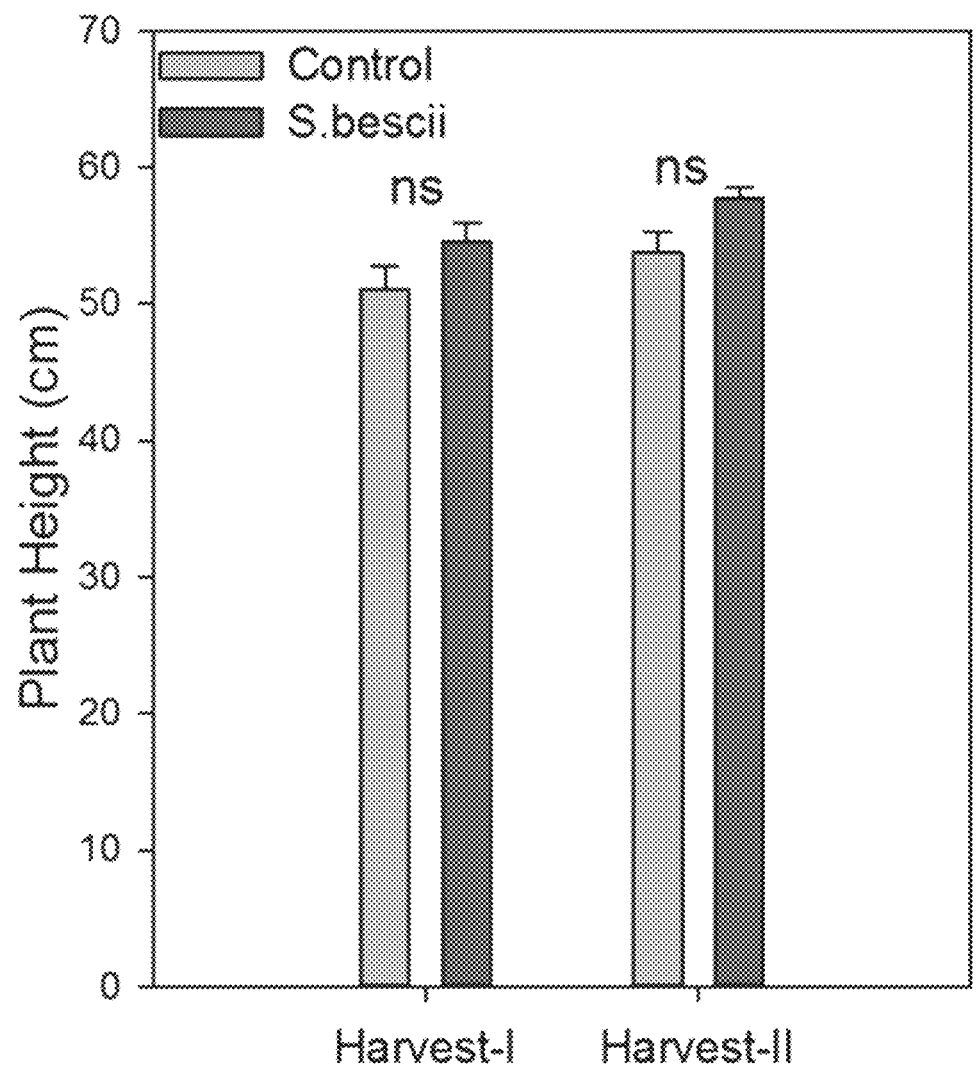
FIG. 17B shows the effect of *S. bescii* colonization on plant height in winter wheat under phosphorous-deficient conditions as compared to an un-inoculated control group with harvests at 30 days (Harvest-I) and 60 days (Harvest-II). Error bar denotes standard error of mean. Significant effects are marked as follows: $0.01 \leq p \leq 0.05$ (*); $0.001 \leq p \leq 0.01$ (); $p \leq 0.001$ (*); and $p > 0.05$ (ns).
Figure 17C:
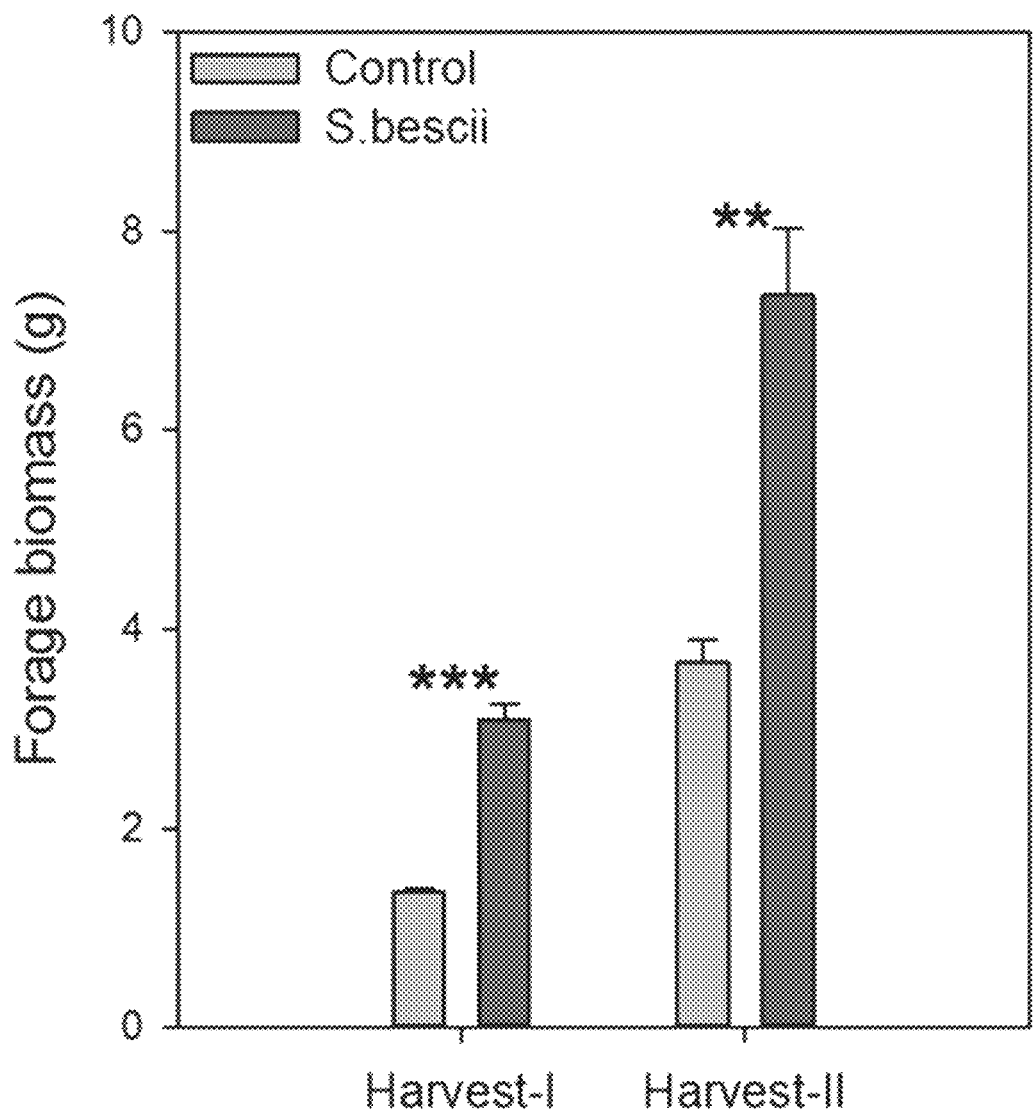
FIG. 17C shows the effect of *S. bescii* colonization on forage biomass in winter wheat under nitrogen-deficient conditions as compared to an un-inoculated control group with harvests at 30 days (Harvest-I) and 60 days (Harvest-II). Error bar denotes standard error of mean. Significant effects are marked as follows: $0.01 \leq p \leq 0.05$ (*); $0.001 \leq p \leq 0.01$ (); $p \leq 0.001$ (*); and $p > 0.05$ (ns).
Figure 17D:
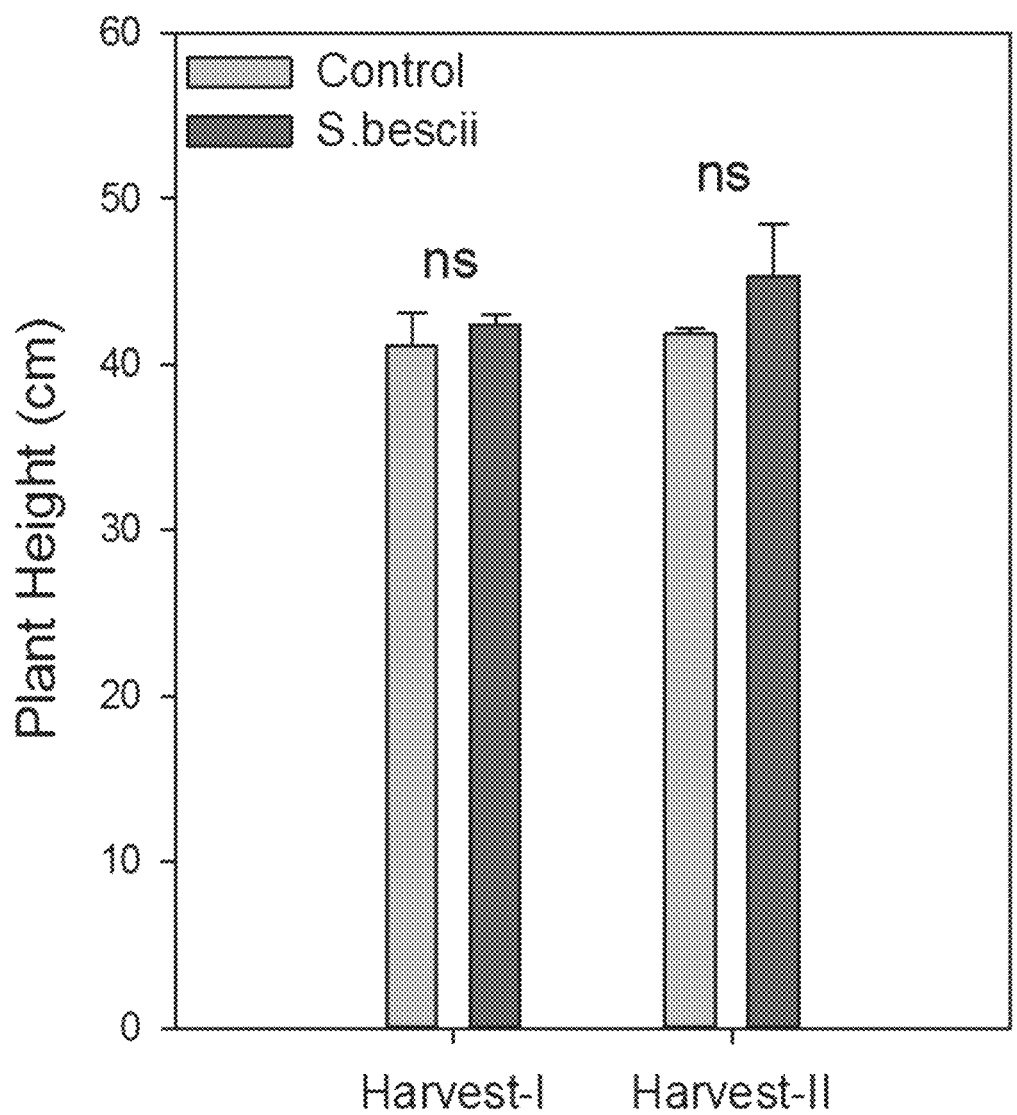
FIG. 17D shows the effect of *S. bescii* colonization on plant height in winter wheat under nitrogen-deficient conditions as compared to an un-inoculated control group with harvests at 30 days (Harvest-I) and 60 days (Harvest-II). Error bar denotes standard error of mean. Significant effects are marked as follows: $0.01 \leq p \leq 0.05$ (*); $0.001 \leq p \leq 0.01$ (); $p \leq 0.001$ (*); and $p > 0.05$ (ns).

Example 7: Effect of S. bescii Colonization on Biomass, Forage Biomass and Plant Height Under Phosphorous-Deficient and Nitrogen-Deficient Conditions in Winter Wheat Winter wheat, cultivar NF101 (Triticum aestivum L) seedlings were colonized in vitro in minimal (M) media with S. bescii following the same protocol as in Example 6. Two different types of M media, namely (a) without phosphorous and (b) without nitrogen were used in this example. After 2 weeks, colonized seedlings and un-inoculated control seedlings were transplanted in 1 gallon pots containing autoclaved Metromix as potting mix. Metromix was washed with clear water to get rid of any available traces of nitrogen and phosphorous. Two identical sets of plants for each treatment were maintained in the greenhouse for estimation of forage biomass four weeks (Harvest-I) and eight weeks (Harvest-II) after transferring into the greenhouse, respectively. Plants grown in M media without nitrogen or phosphorous were watered with ½ strength Hoagland's solution without nitrogen or phosphorous, respectively, to estimate the effect of nitrogen or phosphorous deficiency. The experiment was conducted in three replicates. Un-inoculated plants were maintained in the same way and were used as a control for data analysis. Photographs of five replicate plants for each treatment were taken and are shown in FIGS. 16A-16B. The data were analyzed using ANOVA. When a significant F-test was observed, treatment means were compared using lest significant differences (LSD) at p<0.05 using Costat statistical software 6.4 (Cohort, Berkeley, Calif., United States). The results were plotted graphically using SigmaPlot 12.5 (Systat Software, San Jose, Calif., United States) as shown in FIGS. 17A-17D. As shown, S. bescii colonization enhances biomass of winter wheat under both nitrogen-deficient and phosphorous deficient conditions (FIGS. 16A-16B) and significantly enhances forage biomass in winter wheat under both nitrogen-deficient and phosphorous-deficient conditions (FIGS. 17A, 17C) as compared to un-inoculated winter wheat.

Example 8: Effect of S. bescii Colonization on Grain Yield in Winter Wheat

Winter wheat, cultivar NF101 (Triticum aestivum L) seedlings were colonized in the greenhouse using a bentonite clay-based inoculation protocol. Bentonite clay particles were thoroughly sieved using mesh size 10 (2 mm) to get a uniform particle size. One-liter media bottles were filled with 400 ml of sterile clay particles by volume and subsequently sterilized by autoclave two times with a gap of 2 days. Thereafter, 150 ml of Modified Melin Norkan's broth pH 7 was added to each bottle and sterilized one more time by autoclave before inoculating with the seed culture. Each bottle was inoculated with 50 ml of a 4-week old S. bescii liquid culture (Modified Melin Norkan's broth) prepared in 250-ml Erlenmeyer flasks. An equivalent amount of Modified Melin Norkan's broth was added to a control set of bottles. Both the control and the inoculated bottles were incubated in a slanted, stationary position at 24° C. for 8 weeks. The bottles were shaken once per week for uniform distribution of the seed culture. After incubation, the clay particles coated with or without S. bescii were air dried overnight at room temperature under a laminar hood chamber.

For inoculation using bentonite clay, a uniform hole of 5 cm depth was made in the center of D25L single cell root trainers (5 cm in diameter by 25 cm in height; Stuewe & Sons, Inc., Oregon, United States) filled with non-sterile Metromix-350 medium (Scotts-Sierra Horticultural Products, Marysville, Ohio, United States) using a 14-ml propylene round bottom tube (BD Falcon, New Jersey, United States). Clonally propagated seedlings were directly transplanted into this hole. Thereafter, each hole was filled with one half tablespoon of bentonite clay coated with S. bescii or the control clay particles lacking the fungus.

Figure 18A:
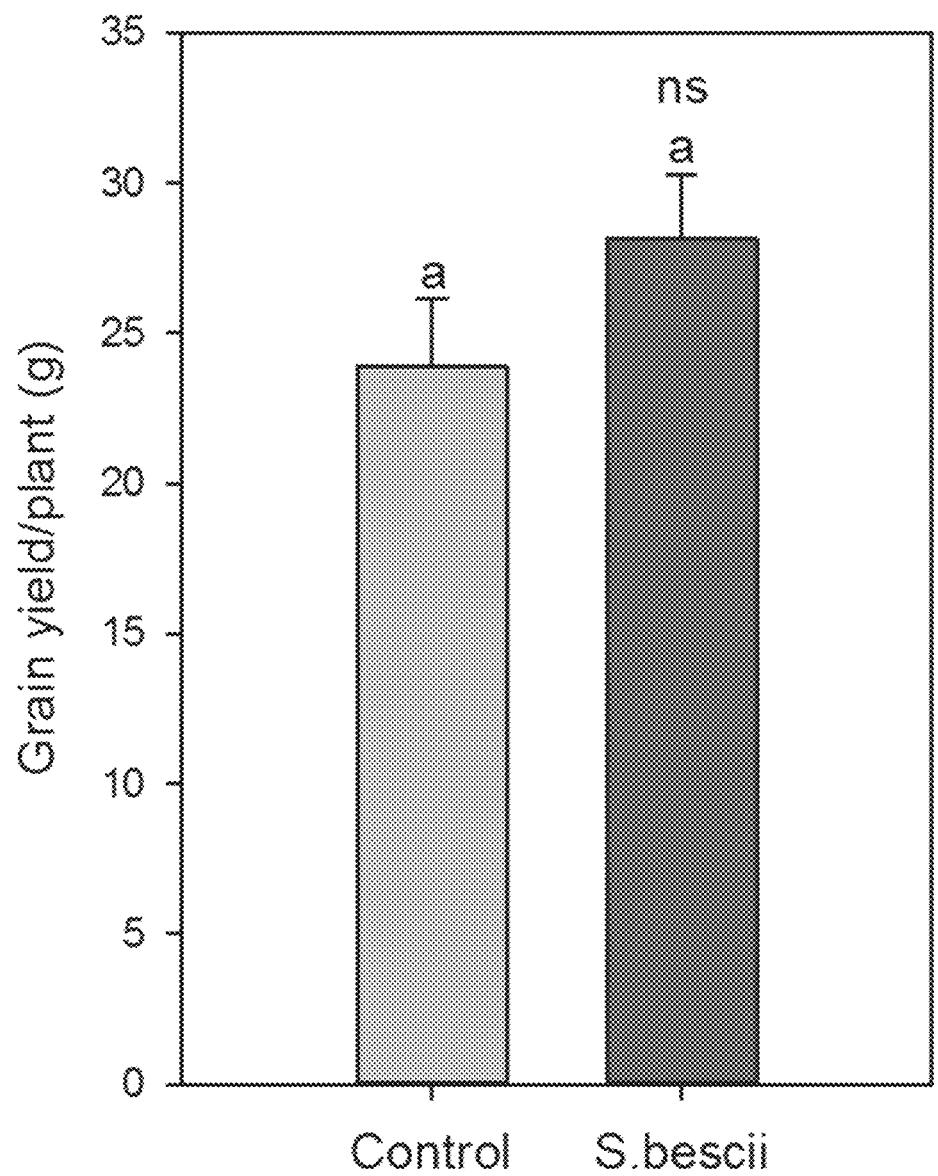
FIG. 18A shows the effect of *S. bescii* colonization on grain yield in grams of winter wheat in field conditions. Error bar denotes standard error of mean. Significant effects are marked as follows: $0.01 \leq p \leq 0.05$ (*); $0.001 \leq p \leq 0.01$ (); $p \leq 0.001$ (*); and $p > 0.05$ (ns).
Figure 18B:
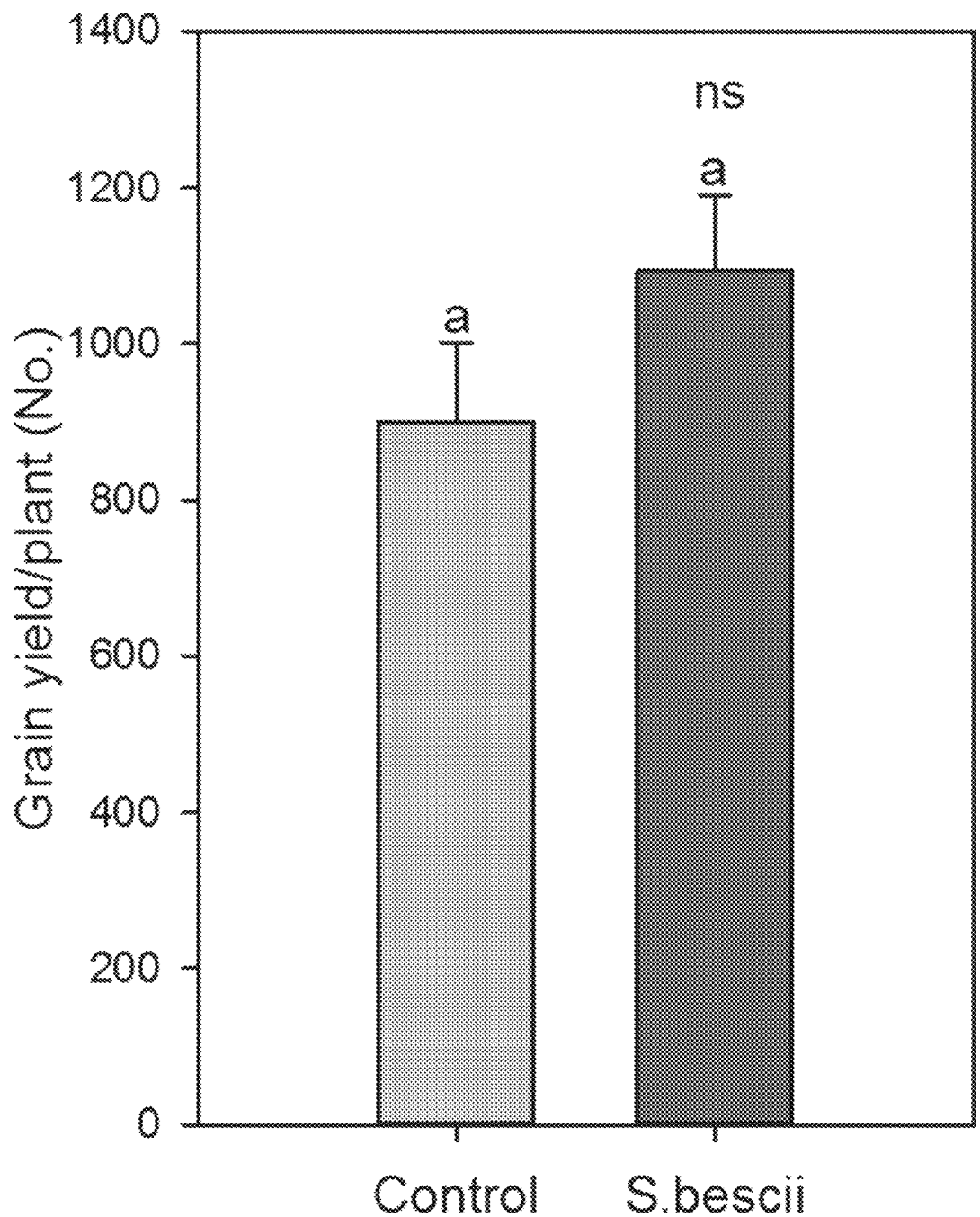
FIG. 18B shows the effect of *S. bescii* colonization on grain yield (number) of winter wheat in field conditions. Error bar denotes standard error of mean. Significant effects are marked as follows: $0.01 \leq p \leq 0.05$ (*); $0.001 \leq p \leq 0.01$ (); $p \leq 0.001$ (*); and $p > 0.05$ (ns).

After 2 weeks, colonized seedlings as well as mock inoculated seedlings were transplanted in the Noble Research Institute's field located in Ardmore, Okla. using a seedling planter. All the treatments were arranged in a randomized complete block design. At the end of the wheat growing season, the crop was harvested for the estimation of grain yield. The experiment was conducted in fifteen replicates. The data were analyzed using ANOVA. When a significant F-test was observed, treatment means were compared using lest significant differences (LSD) at p<0.05 using Costat statistical software 6.4 (Cohort, Berkeley, Calif., United States). The results were plotted graphically using SigmaPlot 12.5 (Systat Software, San Jose, Calif., United States) as shown in FIGS. 18A-18B which show an increase in grain yield with S. bescii of approximately 20%.

Example 9: Colonization of Rice by S. bescii

Figure 19A:
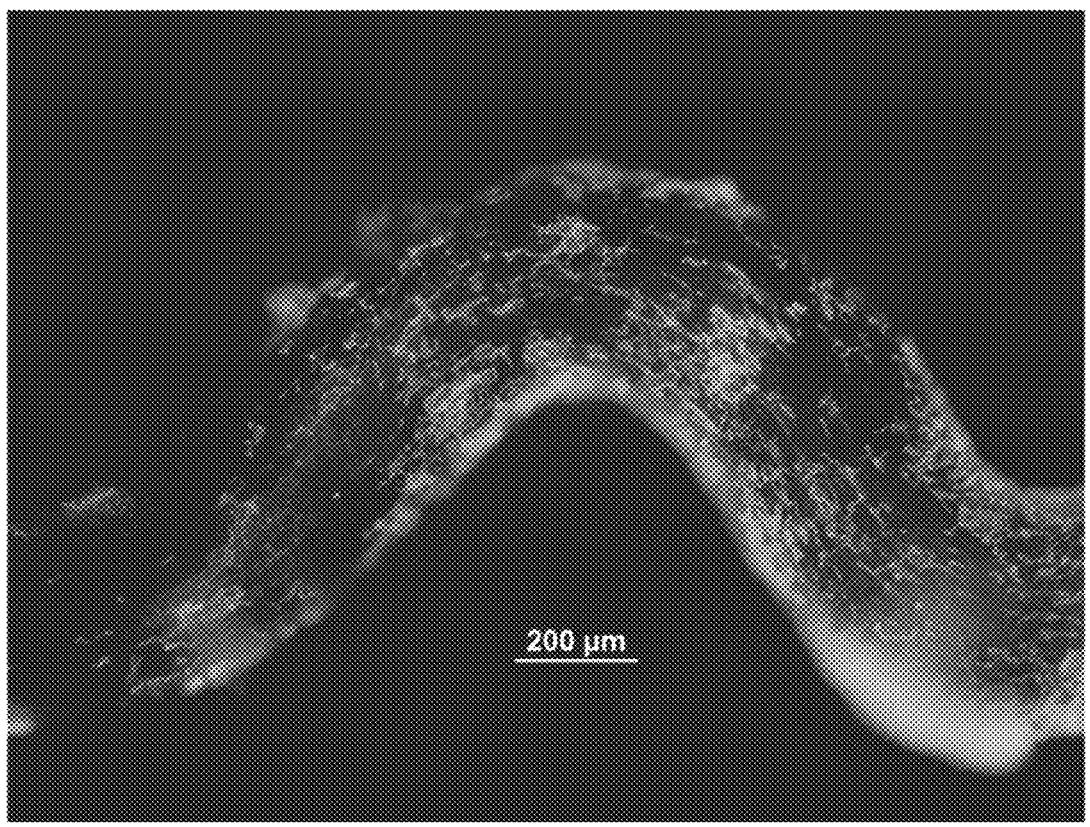
FIG. 19A shows a fluorescence micrograph of colonization of a rice root colonized with *S. bescii*. Scale bar=200 μm.
Figure 19B:
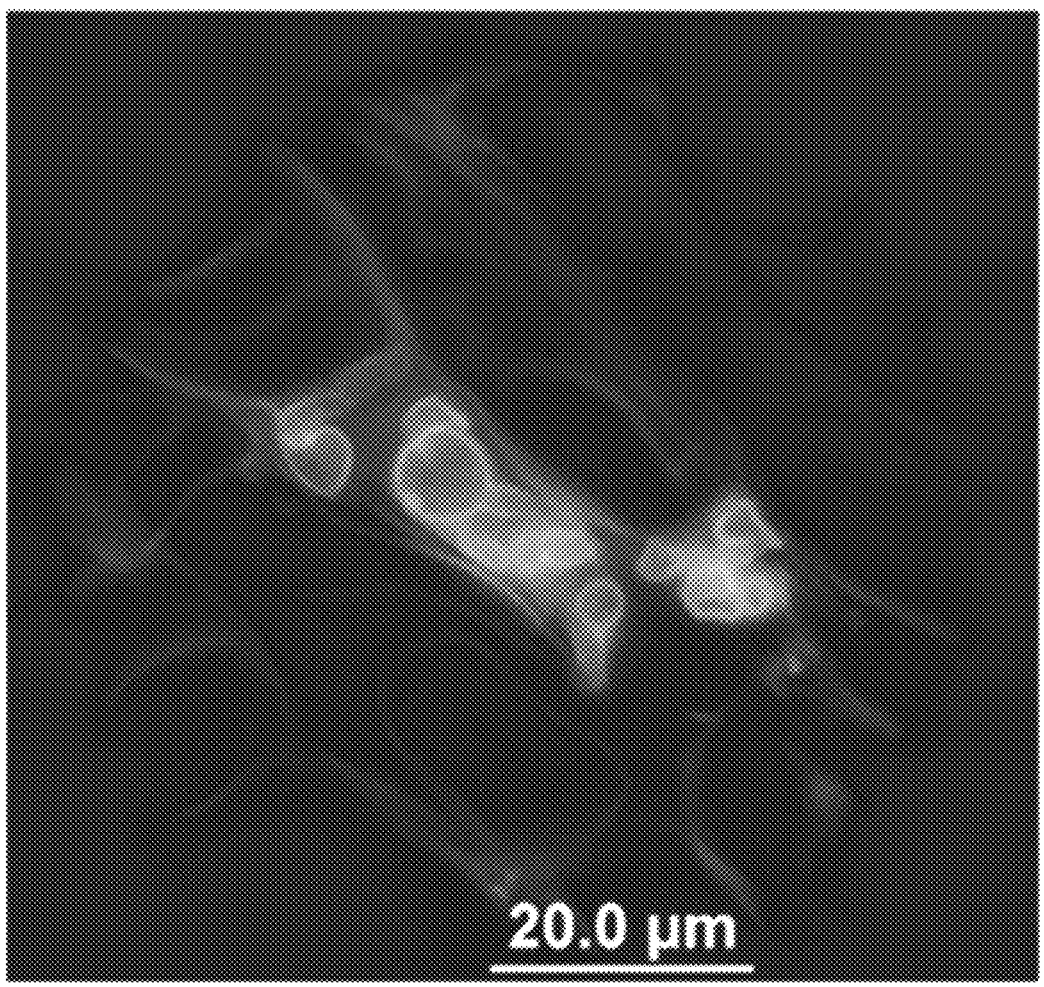
FIG. 19B shows a fluorescence micrograph of a magnified image of a colonized single root cell of rice. Scale bar=20.0 μm.
Figure 19C:
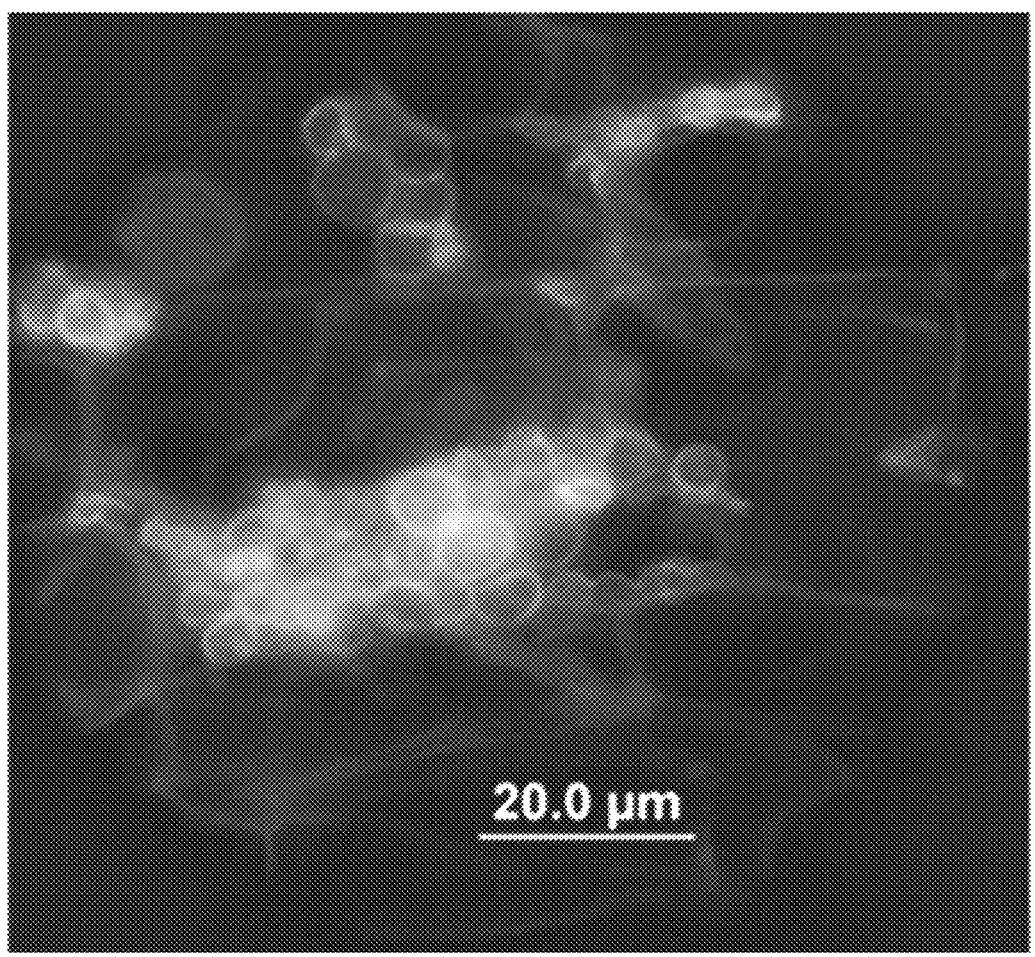
FIG. 19C shows a fluorescence micrograph of a magnified image of a colonized single root cell of rice. Scale bar=20.0 μm.

Rice (Oryza sativa L.) seeds were surface sterilized following standard protocol and germinated in vitro in M media. Seedlings were colonized in vitro with S. bescii. 2 weeks post colonization, plants were harvested and roots and shoots were segregated. Roots were immediately fixed in 50% ethanol. Fixed roots were cut into 1 cm long pieces and stained with WGA-AF® dye (green) for visualization of fungus and counter stained with propidium iodide (red) for visualization of root cells by fluorescence microscopy. An image of a rice root fragment colonized by S. bescii and magnified images of colonized single root cells are shown in FIGS. 19A and 19B-19C, respectively. These results demonstrate colonization of rice roots with S. bescii.

Example 10: Colonization of Cotton by S. bescii

Figure 20A:
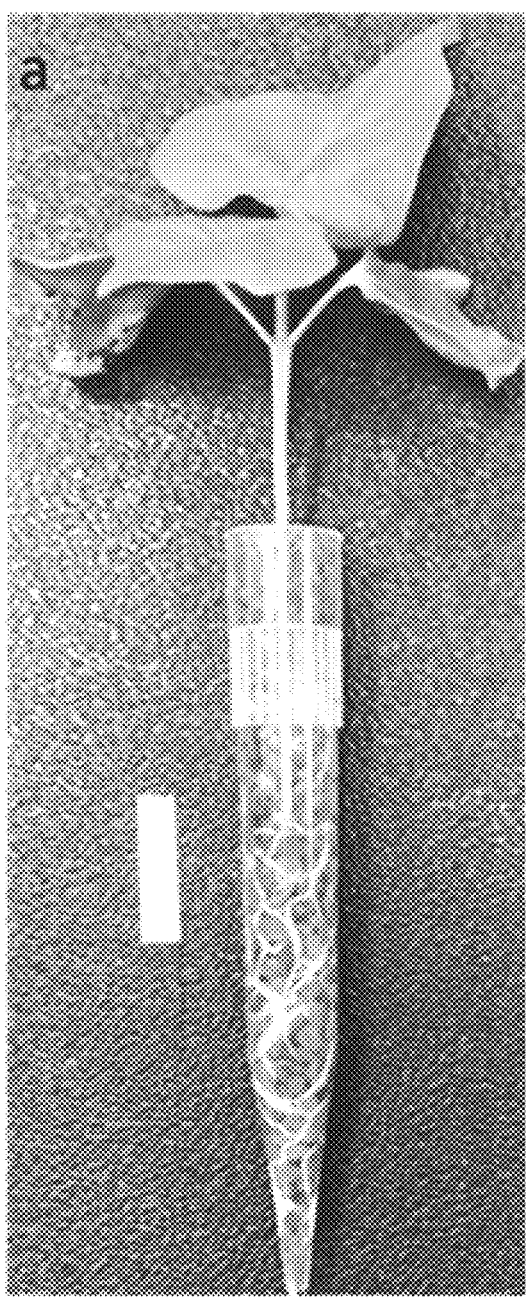
FIG. 20A shows a photograph of a cotton seedling colonized with *S. bescii*.
Figure 20B:
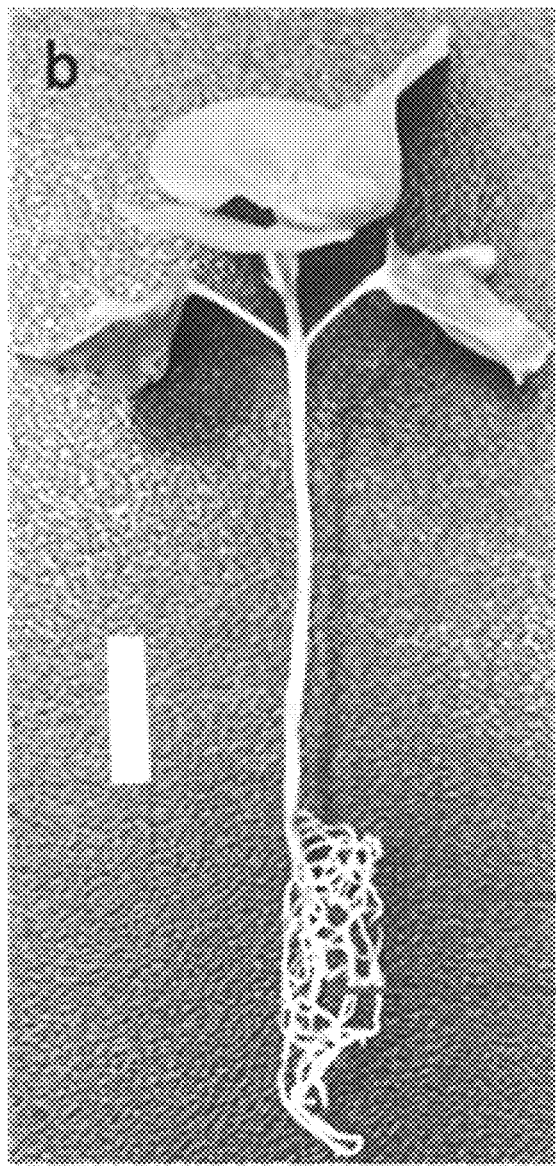
FIG. 20B shows a photograph of a cotton seedling colonized with *S. bescii* showing lateral and primary roots.
Figure 20C:
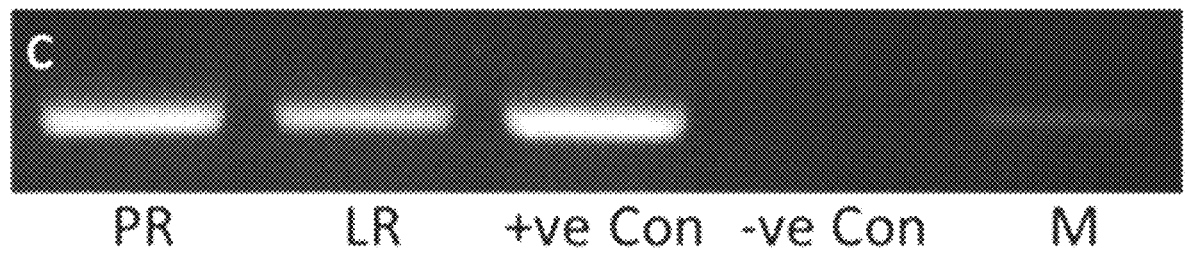
FIG. 20C shows an agarose gel electrophoresis of an amplicons from PCR of primary root (PR), lateral root (LR), positive control (+ve Con), negative control (−ve Con) using *S. bescii* specific primers and a molecular weight marker (M).
Figure 20D:
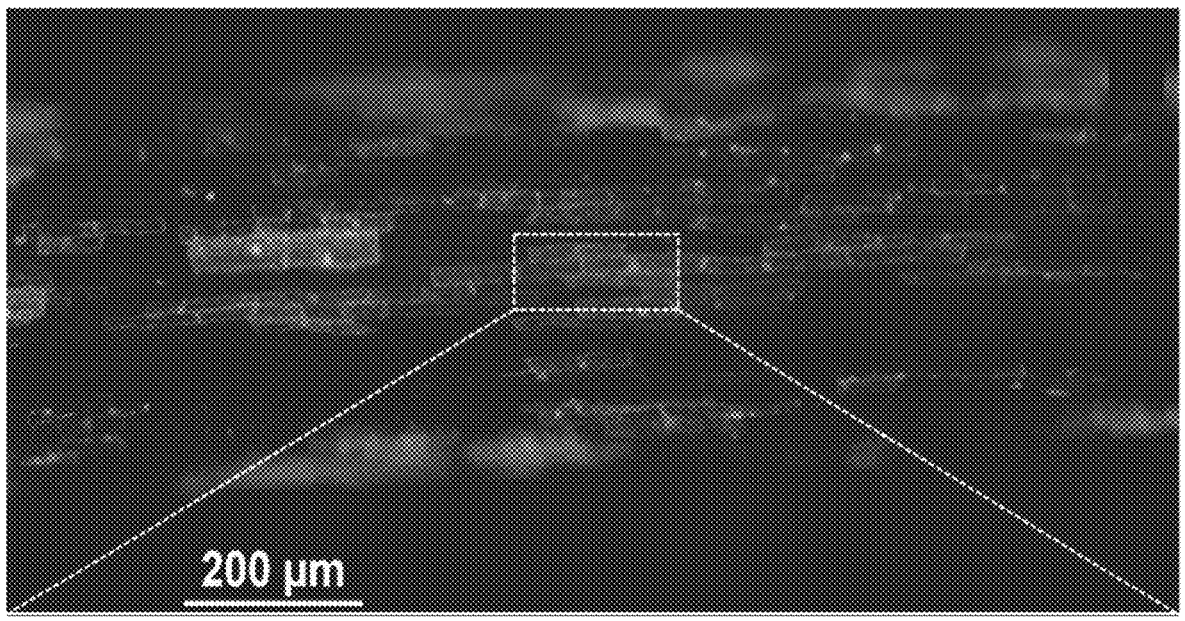
FIG. 20D shows a fluorescence micrograph of a cotton root colonized with *S. bescii*. Scale bar=200 µm.
Figure 20E:
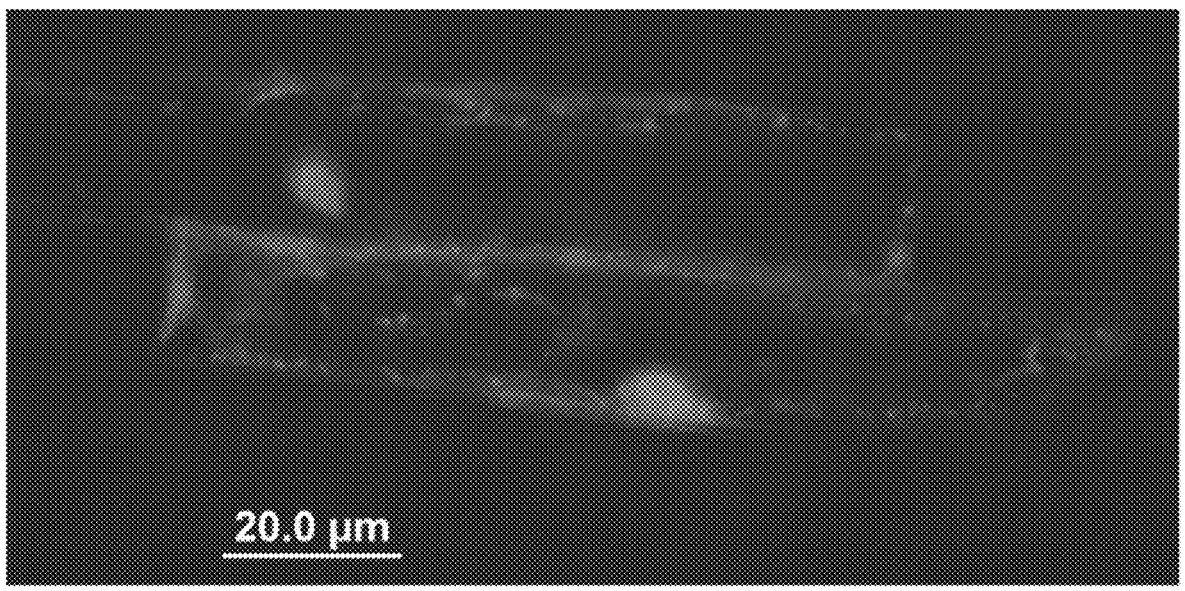
FIG. 20E shows a fluorescence micrograph of a cotton root colonized with *S. bescii*. Scale bar=20.0 µm.

Cotton (Gossypium hirsutum L.) seeds were surface sterilized following standard protocol and germinated in moist sterile filter paper. Seedlings were colonized using the bentonite clay-based method of Example 8. 2 weeks post-colonization, plants were harvested and primary root (PR) and lateral roots (LR) were segregated as shown in FIGS. 20A-20B and PCR done using S. bescii primers (SEQ ID NO: 11 and SEQ ID NO: 12). A positive PCR result indicates successful colonization as shown in FIG. 20C. Colonized root samples were also microscopically observed for more direct evidence of colonization. Colonized roots were fixed in 50% ethanol, then cut into 1 cm long pieces and stained with WGA-AF® dye (green) for visualization of fungus and counterstained with propidium iodide (red) for visualization of root cells by fluorescence microscopy as shown in FIGS. 20D-20E. The results demonstrate successful colonization of cotton by both PCR and microscopy.

Example 11: Estimation of Growth of S. bescii in Agar Plates

S. bescii were inoculated in M (minimal) media containing phosphate or phosphite as the sole source of P. Plates were incubated in the dark at 24° C. for 14 days. After 14 days, images of fungal colonies were captured using a scanner (as shown in FIG. 21) and colony diameter was measured using software Image J. As shown in FIG. 21, radial growth of S. bescii is greater when all P is supplied as Phi which suggests that S. bescii has little or no sensitivity to Phi and may actually be stimulated by the presence of Phi.

Example 12: Phosphite Utilization by S. bescii

Figure 22:
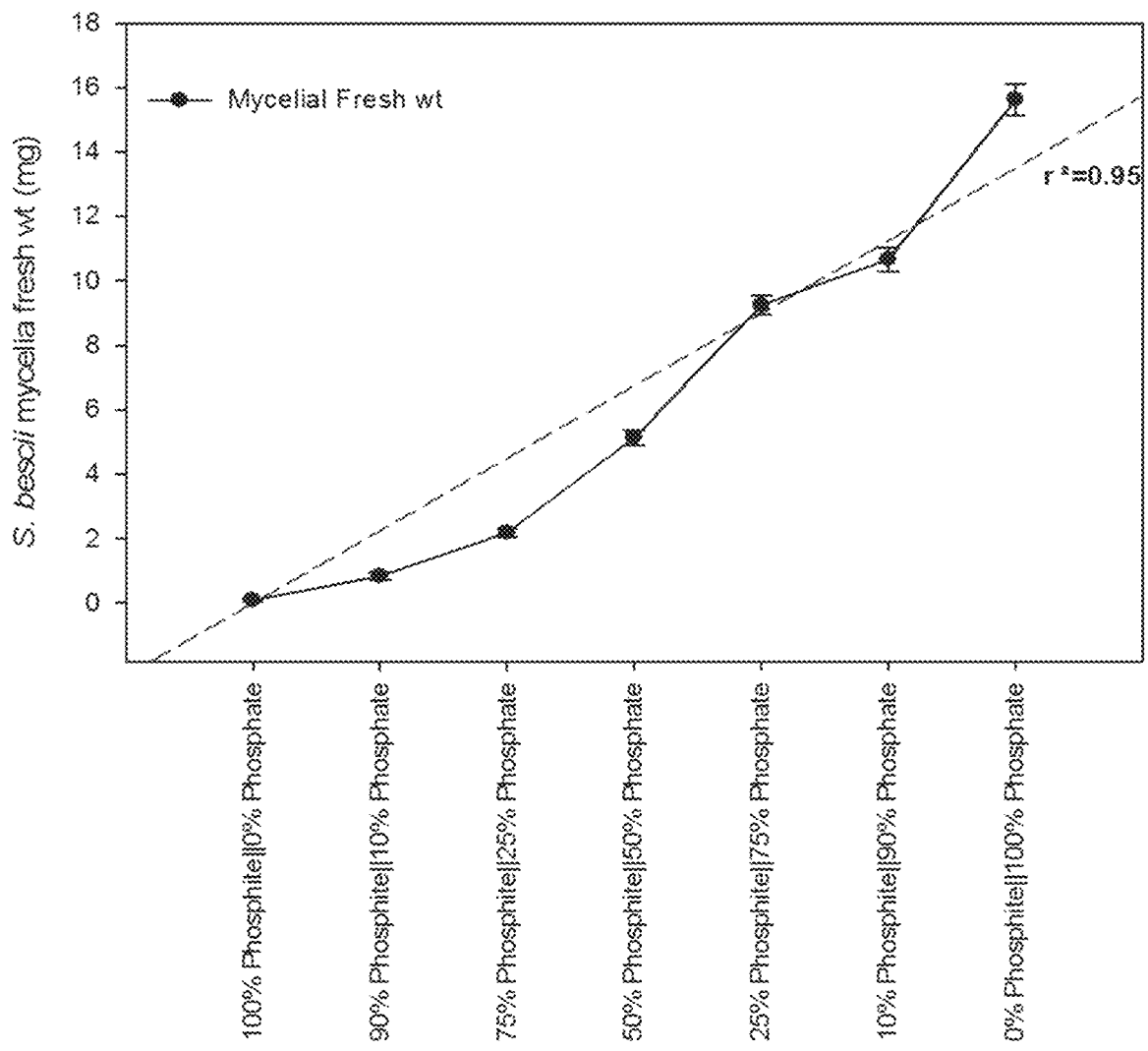
FIG. 22 shows a graph of fresh weight of *S. bescii* mycelia grown in liquid media containing Phi and or Pi as the phosphorus source with 100% phosphite/0% phosphate, 90% phosphite/10% phosphate, 75% phosphite/25% phosphate, 50% phosphite/50% phosphate, 25% phosphite/75% phosphate, 10% phosphite/90% phosphate or 0% phosphite/100% phosphate. Error bars denote standard error of mean.

S. bescii was inoculated in 5 mL of M (minimal) media broth with varying concentrations between 0% and 100% of Phi (out of the total Phi and Pi) contained in a 50 mL Falcon tube. Tubes were incubated in the dark at 24° C. for 14 days. Uninoculated ("mock inoculation") control tubes were also incubated in the same manner. After 14 days, fungal growth was estimated in terms of biomass of fresh tissue as shown in FIG. 22. Phosphate and phosphite content of the M media after 14 days was estimated by ion chromatography.

As shown in FIG. 22, the data suggests a positive relationship between S. bescii biomass and Pi concentration, where almost no growth is observed when all P in the media is in the Phi form with maximal growth observed when all P in the media is in the Pi form. Without being bound to theory, it is believed that in a liquid medium each growing hyphal tip or apex is constantly exposed to the full strength Phi, while solid media allows the absorptive digestive machinery of S. bescii to function more efficiently to create a small zone or film around individual hyphal strands where it may be able to convert Phi to Pi. In fact, as shown in FIG. 21, the presence of 100% Phi in solid media appears to stimulate growth which, without being bound to theory, suggests a "foraging" behavior by S. bescii.

Figure 23:
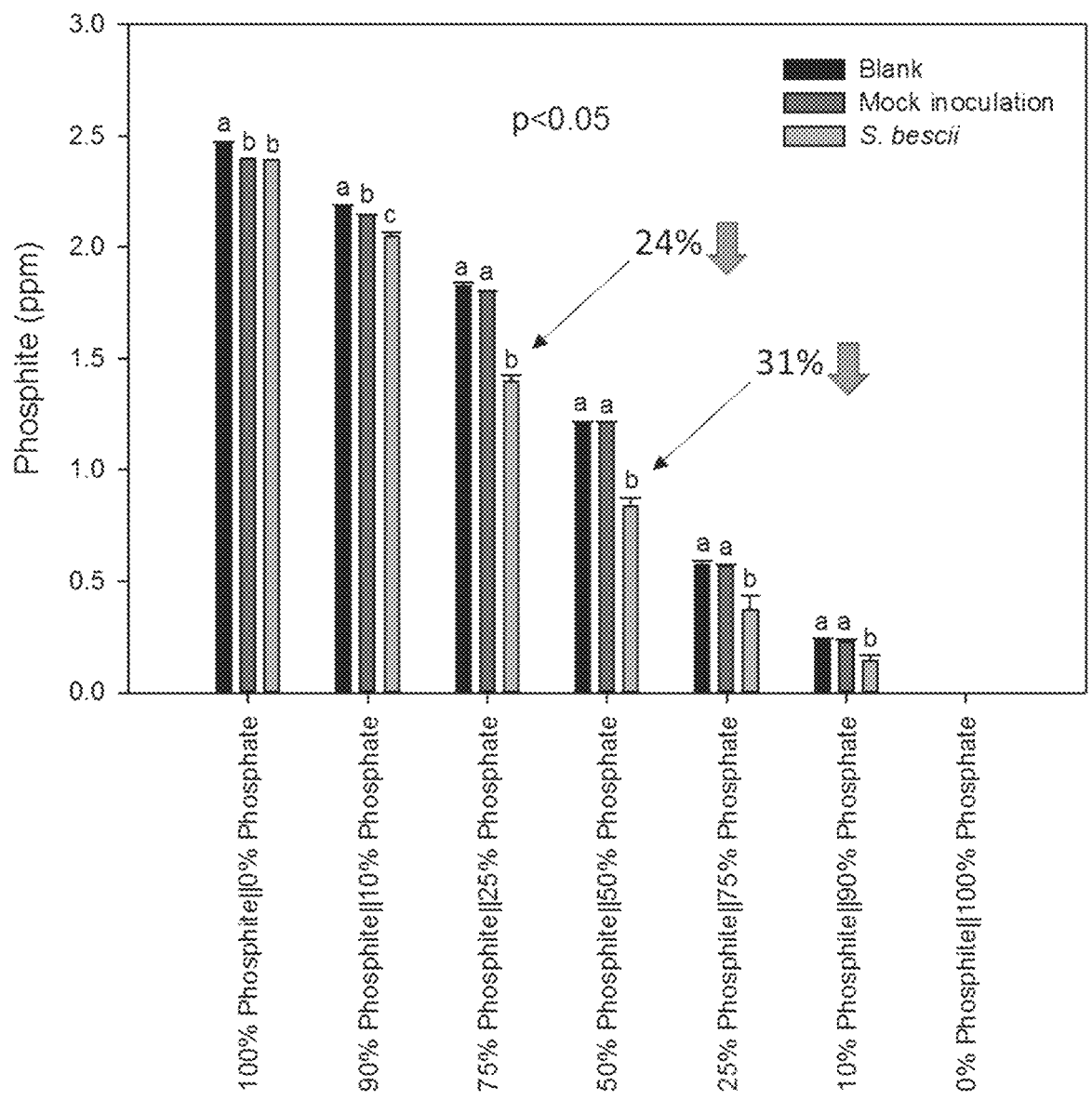
FIG. 23 shows phosphite uptake by *S. bescii* grown in liquid media containing Phi and or Pi as the phosphorous source based on phosphite (in ppm) remaining in the culture medium. Liquid media was supplemented with 100% phosphite/0% phosphate, 90% phosphite/10% phosphate, 75% phosphite/25% phosphate, 50% phosphite/50% phosphate, 25% phosphite/75% phosphate, 10% phosphite/90% phosphate or 0% phosphite/100% phosphate. Error bars denote standard error of mean.

As shown in FIG. 23, chemical analysis of the phosphite (in ppm) remaining in the M medium shows that presence of S. bescii in the liquid media is accompanied by Phi loss from the liquid, suggesting uptake by S. bescii. The "blank" group represents the starting concentration of Phi. Black arrows denote when Phi concentration starts at 50% to 75% of the total, where S. bescii appears to remove the greatest amount of phosphite from the media.

Table 2 below shows the uptake of phosphite and phosphate for S. bescii based on the amount of phosphite or phosphate remaining in the medium (Each data point is the mean concentration of phosphite or phosphate in ppm. Error bar denotes standard of mean) As shown in Table 2, S. bescii uses all of the Pi that is available in the solution (note zero values for phosphate of each concentration).

TABLE 2

Phosphite and phosphate uptake based on phosphite and phosphate remaining in culture medium incubated with or without S. bescii

| | | Phosphite (ppm) | | | | Phosphate (ppm) | |
| --- | --- | --- | --- | --- | --- | --- | --- |
| Treatment | Blank | Mock Inoculation | S. bescii | Difference | Blank | Mock Inoculation | S. bescii |
| 100% Phosphite ‖ 0% Phosphate | 2.469 ± 0.004 | 2.394 ± 0.004 | 2.392 ± 0.007 | 0.002 | 0.00 ± 0.00 | 0.00 ± 0.00 | 0.00 ± 0.00 |
| 90% Phosphite ‖ 10% Phosphate | 2.181 ± 0.009 | 2.143 ± 0.005 | 2.049 ± 0.016 | 0.094 | 0.357 ± 0.03 | 0.251 ± 0.004 | 0.00 ± 0.00 |

TABLE 2-continued

Phosphite and phosphate uptake based on phosphite and phosphate remaining in culture medium incubated with or without S. bescii

| Treatment | Phosphite (ppm) | | | | Phosphate (ppm) | | |
|---|---|---|---|---|---|---|---|
| | Blank | Mock Inoculation | S. bescii | Difference | Blank | Mock Inoculation | S. bescii |
| 75% Phosphite ∥ 25% Phosphate | 1.826 ± 0.013 | 1.801 ± 0.004 | 1.395 ± 0.028 | 0.406 | 0.794 ± 0.033 | 0.724 ± 0.015 | 0.00 ± 0.00 |
| 50% Phosphite ∥ 50% Phosphate | 1.203 ± 0.012 | 1.213 ± 0.004 | 0.837 ± 0.037 | 0.376 | 1.668 ± 0.045 | 1.624 ± 0.008 | 0.00 ± 0.00 |
| 25% Phosphite ∥ 75% Phosphate | 0.574 ± 0.017 | 0.57 ± 0.006 | 0.372 ± 0.063 | 0.202 | 2.396 ± 0.11 | 2.466 ± 0.013 | 0.00 ± 0.00 |
| 10% Phosphite ∥ 90% Phosphate | 0.23 ± 0.012 | 0.228 ± 0.011 | 0.144 ± 0.023 | 0.084 | 2.903 ± 0.068 | 2.802 ± 0.005 | 0.00 ± 0.00 |
| 0% Phosphite ∥ 100% Phosphate | 0.00 ± 0.00 | 0.00 ± 0.00 | 0.00 ± 0.00 | — | 3.335 ± 0.128 | 3.123 ± 0.018 | 0.00 ± 0.00 |

Example 13: Assessment of Phosphite Utilization by S. bescii Using Winter Wheat (NF101) as a Model Crop Wheat seedlings will be colonized in situ with S. bescii using the clay particle method in ½-gallon pots and maintained in green house for 30 days. Triple washed metromix will be used as potting mix to ensure that potting mix was free of any inorganic phosphite or phosphate respectively. Control (optimum phosphate) plants will be treated with ½ strength Hoagland's solution containing the optimum phosphate concentration. Phosphite treatment will be treated with ½ strength Hoagland's solution where phosphate will be substituted with equimolar concentration of phosphite. Phosphate and phosphite treatment will be added 1-2 times per week. Control plants that are not colonized with *S. bescii* will be treated with phosphate or phosphite in the same manner. All treatment groups will be performed in triplicate. Plants will be harvested and assessed for plant biomass, phosphate and phosphite content in planta and leaf chlorophyll content.

It is predicted that the root tissues and, to a lesser extent, the shoot tissues of plants treated solely with Phi as the P source accumulate Phi and demonstrate a loss of biomass compared to Pi-treated plants. However, it is expected that when *S. bescii* is present, the Phi-treated plants will contain significant levels of Pi in their roots, suggesting that *S. bescii* may have converted the Phi to Pi as it passed through the hyphal matrix enveloping the roots.

Example 14: Estimation of Growth Rate of *S. bescii* in Agar Plates

*S. bescii* will be inoculated in M (minimal) media containing phosphate or phosphite as sole source of P. Plates will be incubated in the dark at 24° C. Colony diameter will be recorded after 5 days of inoculation and thereafter every two days to estimate radial growth rate. After 13 days, images of fungal colonies will captured using a scanner and colony diameter will be measured using software Image J.

Example 15: Colonization of Peat by *S. bescii*

Different sizes of peat will be inoculated with *S. bescii*. Colonization of peat will be visualized by electron microscopy. It is expected that *S. bescii* will colonize peat and will be able to derive N, P and C nutrition (as well as macro and micronutrients) from the peat.

The foregoing description of specific embodiments of the present disclosure has been presented for purpose of illustration and description. The exemplary embodiments were chosen and described in order to best explain the principles of the disclosure and its practical application, to thereby enable others skilled in the art to best utilize the subject matter and various embodiments with various modifications are suited to the particular use contemplated.

Example 16: Winter Wheat Field Trial

Inoculum was prepared following the method described by Ray et al. (2015). Bentonite clay particles were thoroughly sieved using mesh size 10 (2 mm) to get a uniform particle size. One-liter media bottles were filled with 400 ml of sterile clay particles by volume and subsequently sterilized by autoclave two times with a gap of 2 days. Thereafter, 150 ml of Modified Melin Norkan's (MMN) broth pH 7 was added to each bottle and sterilized one more time by autoclave before inoculating with the seed culture. Each bottle was inoculated with 50 ml of a 4-week-old *S. bescii* liquid culture (MMN) prepared in 250-ml Erlenmeyer flasks. An equivalent amount of MMN broth was added to a control set of bottles. Both the control and the inoculated bottles were incubated in a slanted, stationary position at 24° C. for 8 weeks. The bottles were shaken once per week for uniform distribution of the seed culture.

For inoculation using bentonite clay, a uniform hole of was made in the center of 48 well standard insert trays (American Plant Products, Oklahoma City, Okla.) filled with non-sterile Metromix-350 medium (Scotts-Sierra Horticultural Products, Marysville, Ohio). Seedlings of winter wheat (NF101) were directly transplanted into this hole. Thereafter, each hole was filled with one half tablespoon of bentonite clay coated with S. bescii. For direct comparison, seedlings were treated with un-coated clay particle (mock inoculation) and without any clay particle (control) respectively.

One-month-old seedlings were transplanted into the field located in Gene Autry, Okla., using Hatfield seedling Transplanter Model 2.0 (Johnny's selected seeds, ME, USA). Treatment plots were designed in a randomized block design with 16 replicates for each treatment (FIGS. 1 and 2). At the end of the growing season, plants were harvested manually, and threshed using the Wintersteiger LD 350 laboratory thresher (Wintersteiger Inc. Salt Lake City, Utah). Total grain yield (grain wt. basis) was estimated for each of the three treatment.

Figure 24:
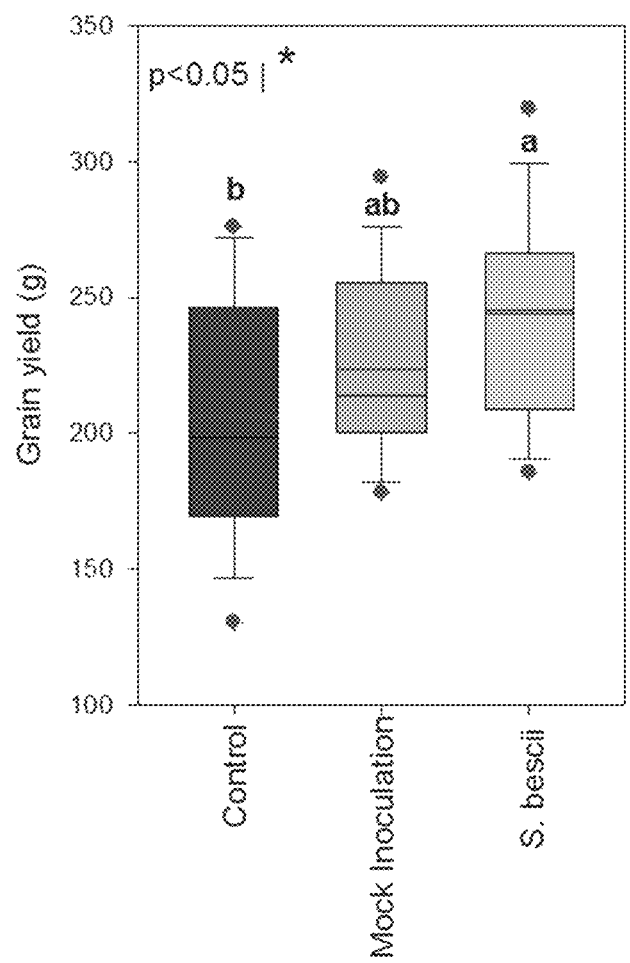
FIG. 24 shows the grain yield from a field trial of winter wheat.

The effect of S. bescii colonization on total grain yield (grain wt. basis) is depicted in FIG. 24. The data were analyzed using one-way analysis of variance (ANOVA) with a single factor, i.e. S. bescii colonization using CoStat statistical software 6.4 (Cohort Berkeley, Calif.). The data was plotted graphically using SigmaPlot 12.5 (Systat Software, San Jose, Calif.).

The results shown in FIG. 24 demonstrate an increase in grain yield with colonization by S. bescii compared to the control which indicates that S. bescii can have a beneficial effect on grain yield.

Example 17: Coating of Winter Wheat Seeds with S. bescii

S. bescii was grown in 50 ml of Modified Melin Norkan's (MMN) broth in 250 ml Erlenmeyer's flask for 8 weeks in stationary condition at 24° C. in dark. 8 g of mycelia (fresh weight basis) was harvested by filtration. The mycelial pellet was washed in sterile MilliQ water two times by vortexing in 250 ml Erlenmeyer's flask for 8 weeks in stationary condition at 24° C. in dark. 400 g of mycelia (fresh weight basis) was harvested by filtration. The mycelial pellet was washed in sterile MilliQ water two times by vortexing and centrifugation. The washed mycelia was suspended in 10 ml 0.2% Xanthan gum to make S. bescii mycelial suspension. 5 ml of S. bescii mycelial suspension was used to coat 50 grams of winter wheat seeds. Seed coating was done by spraying S. bescii mycelial suspension onto wheat seeds taken in a concrete cement mixer under rotatory condition. Following coating, seeds were air dried at room temperature for 30-40 minutes. For mock inoculation treatment, seeds were coated with 50 ml of 0.2% Xanthan gum solution in a similar manner.

For both the S. bescii-coated treatment group and the mock inoculation group ("Control"), both were grown in the greenhouse in 2½ gallon pots. In the early stage (~30 days), plants were fertilized with 500 ml of fertilizer solution twice a week. Between 30-45 days, plants were fertilized with 1 liter of fertilizer solution twice a week. Between 45-90 days, plants were fertilized with 1 liter of fertilizer solution thrice a week. Five different fertilizer solutions were used and a control group received no fertilizer. The five fertilizer solutions were: 1—Phosphate (½ strength Hoagland's solution); 2—No phosphate (½ strength Hoagland's without ammonium phosphate); 3—Phosphite (½ strength Hoagland's solution without ammonium phosphate but with potassium phosphite ($K_2HPO_3$)); 4—ALIETTE® (½ strength Hoagland's solution without ammonium phosphate+ALIETTE®); and 5—Phosphate+Phosphite (combination of "Phosphate" and "Phosphite" fertilizer solutions).

The content of each fertilizer solution was measured as shown in Table 3 below:

TABLE 3

Content of Fertilizer Solutions

| Sample Description | Nitrite | Nitrate | Phosphite | Phosphate | Ammonium | Potassium |
|---|---|---|---|---|---|---|
| | | | mg/L (ppm) | | | |
| Phosphate Fertilizer | n.a. | 372.52 | n.a. | 31.54 | 14.25 | 81.71 |
| No Phosphate Fertilizer | n.a. | 325.92 | n.a. | n.a. | 0.43 | 85.4 |
| Phosphite Fertilizer | n.a. | 330.35 | 23.24 | n.a. | 0.51 | 114.61 |
| Aliette ® | n.a. | 322.49 | 48.17 | n.a. | 4.04 | 85.3 |
| Phosphate + Phosphite | n.a. | 373.02 | 27.03 | 31.99 | 14.32 | 114.61 | and centrifugation. The washed mycelia was suspended in 400 ml 0.2% Xanthan gum to make S. bescii mycelial suspension. 150 ml of S. bescii mycelial suspension was used to coat 6 lbs. of winter wheat seeds. Seed coating was done by spraying S. bescii mycelial suspension onto wheat seeds taken in a concrete cement mixer under rotatory condition. Following coating, seeds were air dried at room temperature for 30-40 minutes. Spraying and air drying were repeated for more efficient seed coating. For mock inoculation treatment, seeds were coated with 150 ml of 0.2% Xanthan gum solution in a similar manner.

Example 18: Coating of Winter Wheat Seeds with S. bescii

To evaluate the effect of S. bescii colonization and the use of phosphate-based and phosphite-based fertilizers, a greenhouse experiment using winter wheat was conducted.

To prepare the coated winter wheat seeds S. bescii was grown in 50 ml of Modified Melin Norkan's (MMN) broth As shown in Table 3, the phosphite fertilizer and ALIETTE® do not contain measurable phosphate content.

Cumulative forage biomass, shoot phosphate uptake, and shoot phosphite uptake were measured at 30, 60 and 90 days post inoculation. Shoot phosphate uptake and shoot phosphite uptake were measured as follows. 10 mg of dry tissue was extracted in 1 ml of MilliQ water. The extract was diluted 1:10 in MilliQ water and filtered with a 0.22 μm filter. The filtrate was analyzed for phosphate and phosphite anions using ion chromatography. Chromatographic separation was achieved on a Dionex ICS-5000 IC system (Thermo Fisher Scientific, USA) using a. Dionex AS11, Ion Pac (2×250 mm) analytical column. Ions were eluted using gradient elution at a flow rate of 0.3 ml/min and detected by suppressed conductivity. Column temperature was maintained at 30° C. and injection volume was 25 μl.

Figure 25:
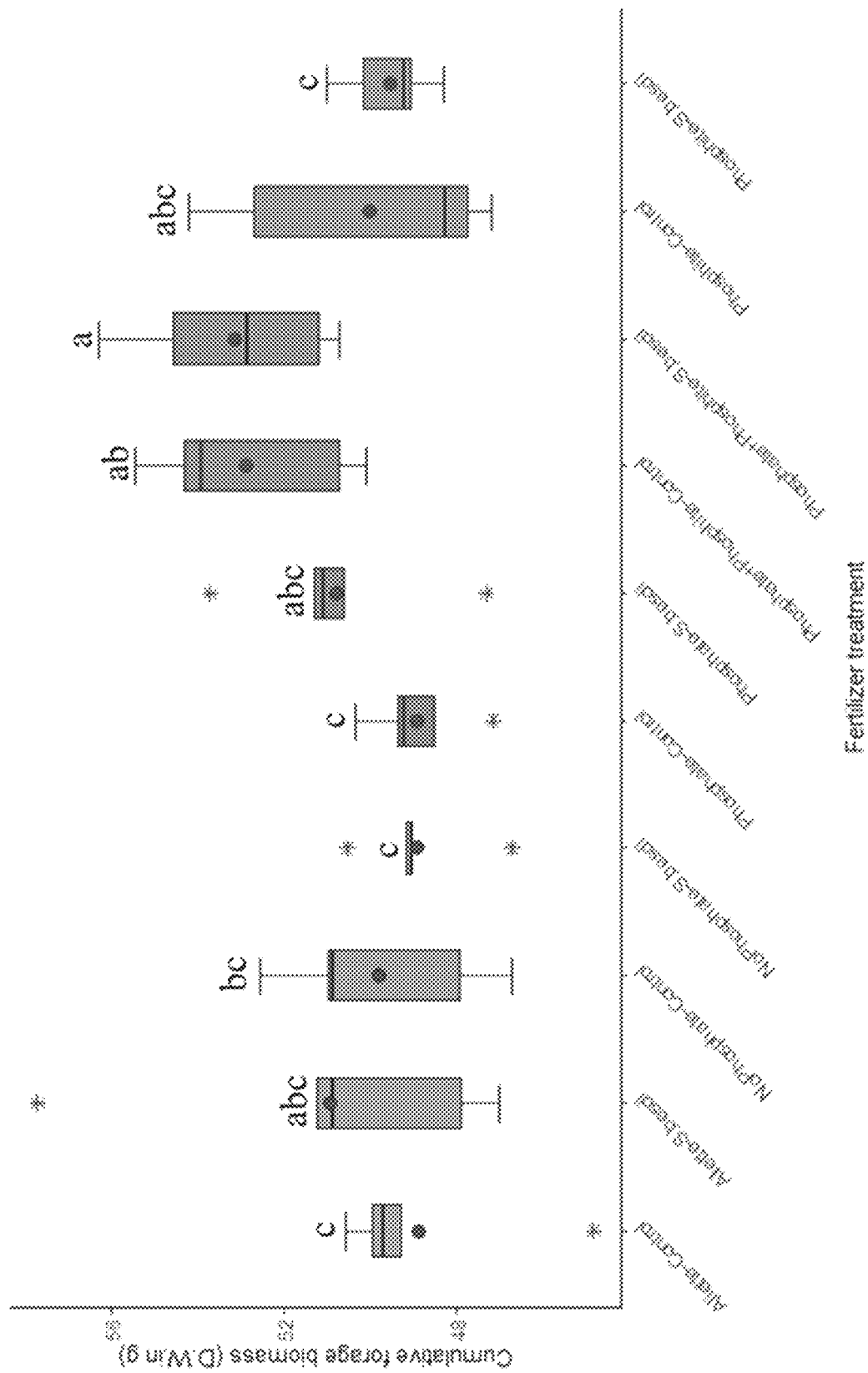
FIG. 25 shows the cumulative forage biomass for winter wheat grown using various fertilizers without and without *S. bescii* colonization. Each box represents cumulative forage dry biomass in g collected after 30, 60 and 90 days post inoculation (dpi) respectively. Bars with different letters indicate significant differences between treatment groups at p≤0.05. Blue dots denote mean, red stars denote outliers.
Figure 26:
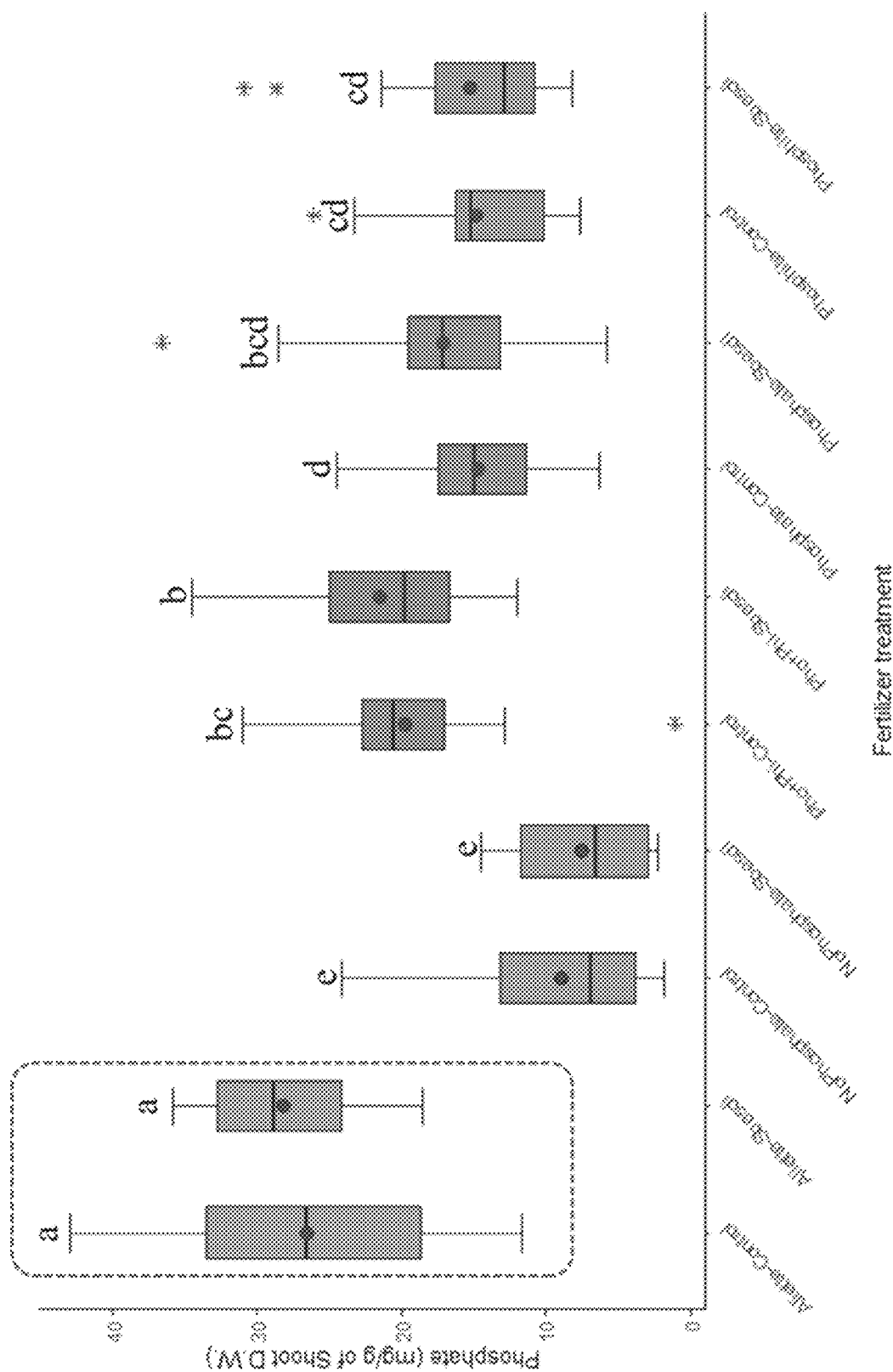
FIG. 26 shows the shoot phosphate uptake for winter wheat grown using various fertilizers without and without *S. bescii* colonization. Each box represents shoot phosphate uptake as mg/g of shoot dry weight after 30, 60 and 90 days post inoculation (dpi) respectively. Bars with different letters indicate significant differences between treatment groups at p≤0.05. Blue dots denote mean, red stars denote outliers.
Figure 27:
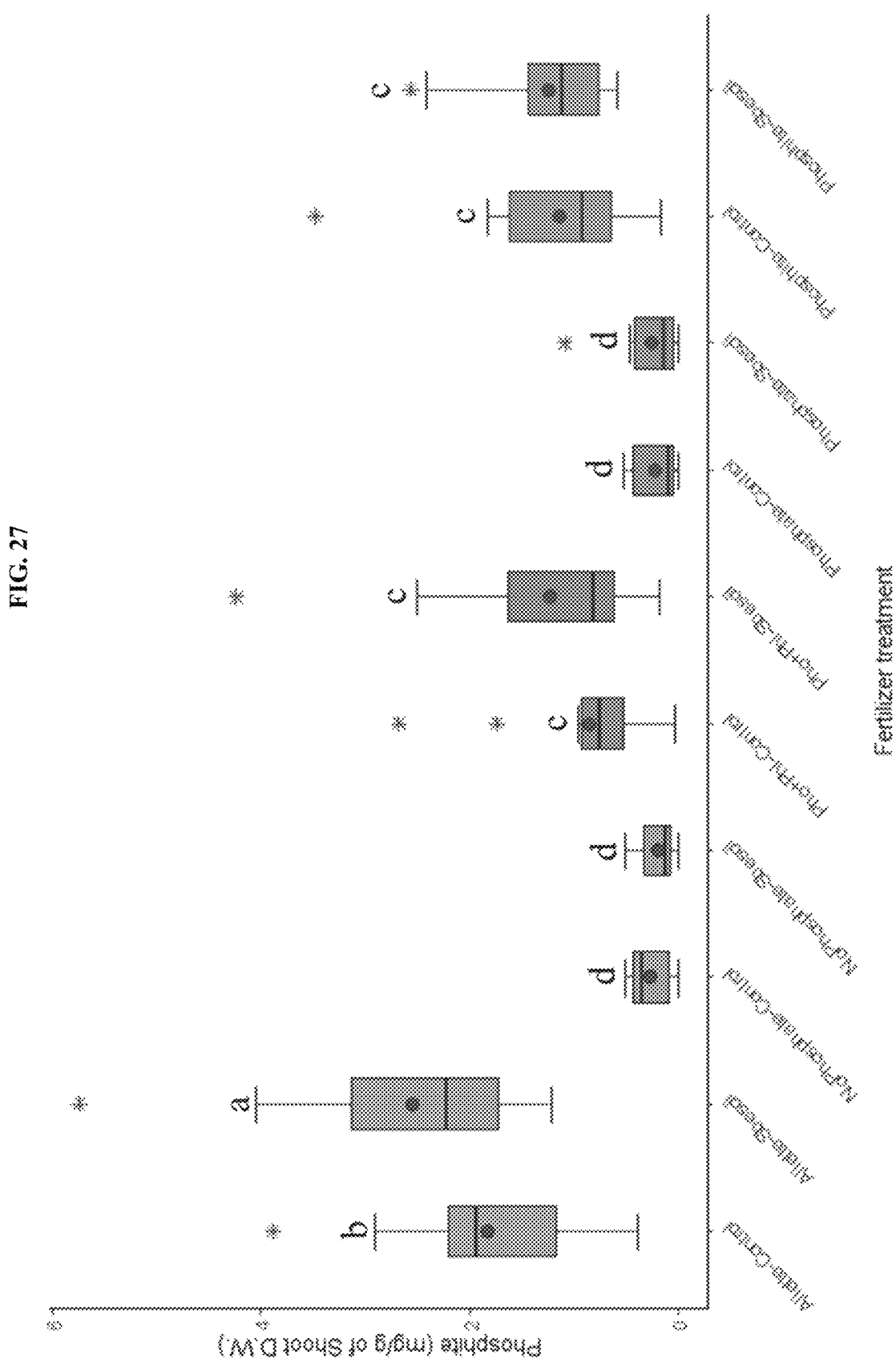
FIG. 27 shows the shoot phosphite uptake for winter wheat grown using various fertilizers without and without *S. bescii* colonization. Each box represents shoot phosphite uptake as mg/g of shoot dry weight after 30, 60 and 90 days post inoculation (dpi) respectively. Bars with different letters indicate significant differences between treatment groups at p≤0.05. Blue dots denote mean, red stars denote outliers.

The effect of S. bescii colonization on cumulative forage biomass of winter wheat (NF101) treated with five different fertilizers, shoot phosphate and phosphite uptake are depicted in FIGS. 25, 26 and 27, respectively. The data were analyzed using analysis of variance (ANOVA) under a two-factor, factorial design with two main factors namely, (a) fertilizer and (b) S. bescii colonization. When a significant F test was observed, treatment means were compared using least significant difference (LSD) value by Duncan's multiple range test (DMRT) at p≤0.05 using CoStat statistical software 6.4 (Cohort Berkeley, Calif.). The significant main effects, and the interactions (at p≤0.05), were plotted graphically using R studio (R studio, Boston, Mass.) using R package ggplot2.

It was found that fertilizer treatment has significant impact on forage biomass (FIG. 25). Although, S. bescii colonization improved forage biomass (~4%) of winter wheat when treated with ALIETTE® or optimum level of phosphate, impact was not statistically significant.

It was also found that fertilizer treatment has significant impact on shoot phosphate uptake (FIG. 26). Interestingly, although ALIETTE® does not have any significant source of phosphate (Table 3), phosphate content was found to significantly more in plants treated with ALIETTE® compared to plants treated with optimum level of phosphate. These results also indicate that even where phosphite is provided as the fertilizer without phosphate, Contrary to phosphate uptake, it was found that both fertilizer treatment and S. bescii colonization has significant impact on shoot phosphite uptake (FIG. 27). S. bescii colonization significantly increased phosphite uptake (~40%) in winter wheat treated with ALIETTE®.

These results indicate that, even when no phosphate is provided to the plant by the fertilizer, the S. bescii endophyte is able to convert phosphite to phosphate in the plant and that phosphite uptake can be increased, for example, as shown by the ALIETTE® treatment group colonized with S. bescii as shown in FIG. 27.

What is claimed is:

1. A composition comprising a synthetic combination of a *Serendipita bescii* endophyte, an inorganic matrix material and a source of phosphite, wherein the *Serendipita bescii* endophyte comprises a nucleotide sequence of SEQ ID NO: 1 or SEQ ID NO: 2, wherein the inorganic matrix material is impregnated or coated with the *Serendipita bescii* endophyte.

2. The composition of claim 1, wherein the inorganic matrix material is bentonite clay.

3. A plant seed coated with a composition, the composition comprising a synthetic combination of a *Serendipita bescii* endophyte, an inorganic matrix material and a source of phosphite, wherein the *Serendipita bescii* endophyte comprises a nucleotide sequence of SEQ ID NO: 1 or SEQ ID NO: 2 wherein the inorganic matrix material is impregnated or coated with the *Serendipita bescii* endophyte.

4. The plant seed of claim 3, wherein said plant seed is a plant seed for a monocot.

5. The plant seed of claim 4, wherein said monocot is selected from the group consisting of wheat (*Triticum aestivum*), durum wheat (*Triticum turgidum* ssp. *durum*), tall wheatgrass (*Thinopyrum ponticum*), western wheatgrass (*Pascopyrum smithii*), maize (*Zea mays*), rice (*Oryza sativa*), sorghum (*Sorghum bicolor*), onion (*Allium cepa*), asparagus (*Asparagus officinalis*), miller (*Gramene* spp.), meadow fescue (*Festuca pratensis*), tall fescue (*Festuca arundinacea*), cereal rye (*Secale cereal*) Russian wild rye (*Psathyrostachys juncea*), oats (*Avena sativa*), bermudagrass (*Cynodon dactylon*), Kentucky bluegrass (*Poa pratensis*), big bluestem (*Andropogon gerardii*), little bluestem (*Schizachyrium scoparium*), blue grama (*Bouteloua gracilis*), black grama (*Bouteloua eriopoda*), side-oat grama (*Bouteloua curipendula*), johnsongrass (*Sorghum halepense*), buffalograss (*Buchloe dactyloides*), and creeping bentgrass (*Agrostis stolonifera*).

6. The plant seed of claim 3, wherein said plant seed is plant seed for a dicot.

7. The plant seed of claim 6, wherein said dicot is selected from the group consisting of alfalfa (*Medicago sativa*), rose (*Rosa* spp.), tomato (*Solanum lycopersicum*), blueberry (*Vaccinium* spp.), cotton (*Gossypium hirsutum*), pepper (*Capsicum* spp.), common bean (*Phaseolus vulgaris*), lentil (*Lens culinaris*), peas (*Pisum sativum*), eggplant (*Solanum melongena*), watermelon (*Citrullus lanatus*), coffee (*Coffea* spp.), apples (*Malus domestica*), plums (*Prunus domestica*), sweet cherry (*Prunus avium*), squash (*Cucurbita pepo* L.), broccoli (*Brassica oleracea*), turnips (*Brassica rapa*), geraniums (*Geranium* spp.), strawberry (*Fragaria×ananassa*), soybean (*Glycine max*), and pecan (*Carya illinoinensis*).

8. The composition of claim 1, wherein the source of phosphite is a phosphonate compound.

9. The composition of claim 1, wherein the composition is substantially free of phosphate.

10. The plant seed of claim 3, wherein said source of phosphite is a phosphonate compound.

* * * * *